(12) United States Patent  
Whitman et al.

(10) Patent No.: US 9,033,868 B2  
(45) Date of Patent: May 19, 2015

(54) COUPLINGS FOR INTERCONNECTING COMPONENTS OF AN ELECTRO-MECHANICAL SURGICAL DEVICE

(75) Inventors: Michael P. Whitman, New Hope, PA (US); John E. Burbank, Ridgefield, CT (US); David A. Zeichner, Oxford, CT (US)

(73) Assignee: Covidien LP, Mansfield, MA (US)

( * ) Notice: Subject to any disclaimer, the term of this patent is extended or adjusted under 35 U.S.C. 154(b) by 97 days.

(21) Appl. No.: 13/093,237

(22) Filed: Apr. 25, 2011

(65) Prior Publication Data

US 2011/0257636 A1    Oct. 20, 2011

Related U.S. Application Data

(60) Division of application No. 10/099,634, filed on Mar. 15, 2002, now Pat. No. 7,951,071, which is a (Continued)

(51) Int. Cl.  
*A61B 1/00* (2006.01)  
*A61B 17/072* (2006.01)  
(Continued)

(52) U.S. Cl.  
CPC ........... *A61B 17/072* (2013.01); *A61B 10/0233* (2013.01); *A61B 17/00* (2013.01);  
(Continued)

(58) Field of Classification Search  
USPC .......... 600/101, 103, 104, 117–118, 137, 154  
See application file for complete search history.

(56) References Cited

U.S. PATENT DOCUMENTS 1,798,902 A    3/1931    Raney  
1,831,250 A    10/1932    Tomlinson (Continued)

FOREIGN PATENT DOCUMENTS

DE    4213426    10/1972  
DE    2330182    1/1975

(Continued)

OTHER PUBLICATIONS

European Search Report for corresponding EP11190714 date of mailing is Feb. 9, 2012 (3 pgs).

(Continued)

*Primary Examiner* — Anhtuan T Nguyen  
*Assistant Examiner* — Jae Woo

(57) ABSTRACT

A flexible shaft includes a flexible, elongated outer sheath, at least one drive shaft disposed within the outer sheath and a moisture sensor disposed within the outer sheath configured to detect moisture within the outer sheath. Another flexible shaft includes a flexible, elongated outer sheath, at least one flexible drive shaft disposed within the outer sheath and a coupling connected to a distal end of the outer sheath configured to couple to a surgical attachment.

A sleeve includes an elongated shaft configured to receive a flexible shaft therein and a securing arrangement configured to selectively and variably retain the elongated shaft in any one of a number of longitudinal positions along the flexible shaft.

A surgical system includes an electro-mechanical driver, an elongated, flexible sheath, at least one drive shaft disposed within the flexible sheath, a surgical attachment coupled to the at least one drive shaft, the electro-mechanical driver configured to drive the surgical attachment, a shape-retaining sleeve, at least a portion of the flexible sleeve being disposed in the shape-retaining sleeve, the shape-retaining sleeve configured to maintain the at least portion of the flexible sheath in a predetermined shape, and an arrangement variably securing the shape-retaining member to the flexible sheath in any one of a number of longitudinal positions along the flexible sheath.

7 Claims, 59 Drawing Sheets

Related U.S. Application Data continuation-in-part of application No. 09/887,789, filed on Jun. 22, 2001, now Pat. No. 7,032,798, which is a continuation-in-part of application No. 09/836,781, filed on Apr. 17, 2001, now Pat. No. 6,981,941, which is a continuation-in-part of application No. 09/723,715, filed on Nov. 28, 2000, now Pat. No. 6,793,652, which is a continuation-in-part of application No. 09/324,451, filed on Jun. 2, 1999, now Pat. No. 6,315,184, and a continuation-in-part of application No. 09/324,452, filed on Jun. 2, 1999, now Pat. No. 6,443,973, and a continuation-in-part of application No. 09/351,534, filed on Jul. 12, 1999, now Pat. No. 6,264,087, and a continuation-in-part of application No. 09/510,923, filed on Feb. 22, 2000, now Pat. No. 6,517,565, which is a continuation-in-part of application No. 09/324,452, filed on Jun. 2, 1999, now Pat. No. 6,443,973, and a continuation-in-part of application No. 09/510,927, filed on Feb. 22, 2000, now Pat. No. 6,716,233, which is a continuation-in-part of application No. 09/324,452, filed on Jun. 2, 1999, now Pat. No. 6,443,973, and a continuation-in-part of application No. 09/510,932, filed on Feb. 22, 2000, now Pat. No. 6,491,201.

(51) Int. Cl.

| | | |
|---|---|---|
| *A61B 10/02* | (2006.01) | |
| *A61B 17/00* | (2006.01) | |
| *A61B 17/115* | (2006.01) | |
| *A61B 17/11* | (2006.01) | |
| *A61B 17/16* | (2006.01) | |
| *A61B 17/32* | (2006.01) | |
| *A61B 17/3207* | (2006.01) | |
| *A61B 19/00* | (2006.01) | |
| *A61B 17/29* | (2006.01) | |
| *A61B 17/3211* | (2006.01) | |

(52) U.S. Cl.
CPC ..... *A61B17/00491* (2013.01); *A61B 17/07207* (2013.01); *A61B 17/11* (2013.01); *A61B 17/1114* (2013.01); *A61B 17/115* (2013.01); *A61B 17/1631* (2013.01); *A61B 17/32002* (2013.01); *A61B 17/320758* (2013.01); *A61B 19/2203* (2013.01); *A61B 19/46* (2013.01); *A61B 2010/0208* (2013.01); *A61B 2017/00022* (2013.01); *A61B 2017/00039* (2013.01); *A61B 2017/00199* (2013.01); *A61B 2017/003* (2013.01); *A61B 2017/00323* (2013.01); *A61B 2017/00398* (2013.01); *A61B 2017/00464* (2013.01); *A61B 2017/00473* (2013.01); *A61B 2017/00477* (2013.01); *A61B 2017/00482* (2013.01); *A61B 2017/00734* (2013.01); *A61B 2017/00831* (2013.01); *A61B 2017/07214* (2013.01); *A61B 2017/2905* (2013.01); *A61B 2017/2943* (2013.01); *A61B 2017/320052* (2013.01); *A61B 2017/32113* (2013.01); *A61B 2019/2242* (2013.01)

(56) References Cited

U.S. PATENT DOCUMENTS

| | | | |
|---|---|---|---|
| 2,031,682 | A | 2/1936 | Wappler et al. |
| 2,174,219 | A | 9/1939 | Balma |
| 2,246,647 | A | 6/1941 | Vancura |
| 2,419,045 | A | 4/1947 | Whittaker |
| 2,725,628 | A | 12/1955 | O'Neilly et al. |
| 3,079,606 | A | 3/1963 | Bobrov et al. |
| 3,120,845 | A | 2/1964 | Horner |
| 3,193,165 | A | 7/1965 | Akhalaya et al. |
| 3,252,643 | A | 5/1966 | Stekopytov et al. |
| 3,253,643 | A | 5/1966 | Gudheim |
| 3,256,875 | A | 6/1966 | Tsepelev et al. |
| 3,275,211 | A | 9/1966 | Hirsch et al. |
| 3,315,863 | A | 4/1967 | O'Dea |
| 3,317,105 | A | 5/1967 | Astefiev et al. |
| 3,388,847 | A | 6/1968 | Kasulin et al. |
| 3,490,576 | A | 1/1970 | Alessi et al. |
| 3,490,675 | A | 1/1970 | Green et al. |
| 3,494,533 | A | 2/1970 | Green et al. |
| 3,499,591 | A | 3/1970 | Green |
| 3,552,626 | A | 1/1971 | Astafiev et al. |
| 3,568,659 | A | 3/1971 | Karnegis |
| 3,589,589 | A | 6/1971 | Akopov |
| 3,593,903 | A | 7/1971 | Astafiev et al. |
| 3,618,842 | A | 11/1971 | Bryan |
| 3,638,652 | A | 2/1972 | Kelley |
| 3,643,851 | A | 2/1972 | Green |
| 3,662,939 | A | 5/1972 | Bryan |
| 3,675,688 | A | 7/1972 | Bryan et al. |
| 3,692,224 | A | 9/1972 | Astafiev et al. |
| 3,717,294 | A | 2/1973 | Green |
| 3,735,762 | A | 5/1973 | Bryan et al. |
| 3,777,538 | A | 12/1973 | Weatherly et al. |
| 3,788,303 | A | 1/1974 | Hall |
| 3,795,034 | A | 3/1974 | Strekopytov et al. |
| 3,815,476 | A | 6/1974 | Green et al. |
| 3,819,100 | A | 6/1974 | Noiles et al. |
| 3,837,555 | A | 9/1974 | Green |
| 3,844,289 | A | 10/1974 | Noiles et al. |
| 3,858,577 | A | 1/1975 | Bass et al. |
| 3,859,986 | A | 1/1975 | Okada et al. |
| 3,882,854 | A | 5/1975 | Hulka et al. |
| 3,892,228 | A | 7/1975 | Mitsui |
| 3,935,981 | A | 2/1976 | Akopov et al. |
| 3,949,924 | A | 4/1976 | Green |
| 3,952,748 | A | 4/1976 | Kaliher et al. |
| RE28,932 | E | 8/1976 | Noiles et al. |
| 4,014,492 | A | 3/1977 | Rothfuss |
| 4,027,510 | A | 6/1977 | Hiltebrandt |
| 4,060,089 | A | 11/1977 | Noiles |
| 4,064,881 | A | 12/1977 | Meredith |
| 4,071,029 | A | 1/1978 | Richmond et al. |
| 4,085,756 | A | 4/1978 | Weaver |
| 4,086,926 | A | 5/1978 | Green et al. |
| 4,092,986 | A | 6/1978 | Schneiderman |
| 4,111,206 | A | 9/1978 | Vishnevsky et al. |
| 4,169,476 | A | 10/1979 | Hiltebrandt |
| 4,198,959 | A * | 4/1980 | Otani ........................ 600/106 |
| 4,198,960 | A | 4/1980 | Utsugi |
| 4,198,982 | A | 4/1980 | Fortner et al. |
| 4,202,479 | A | 5/1980 | Razgulov et al. |
| 4,202,480 | A | 5/1980 | Annett |
| 4,207,873 | A | 6/1980 | Kruy |
| 4,207,898 | A | 6/1980 | Becht |
| 4,244,372 | A | 1/1981 | Kapitanov et al. |
| 4,250,873 | A | 2/1981 | Bonnet |
| 4,261,244 | A | 4/1981 | Becht et al. |
| 4,273,109 | A | 6/1981 | Enderby |
| 4,273,111 | A | 6/1981 | Tsukaya |
| 4,273,129 | A | 6/1981 | Boebel |
| 4,286,585 | A | 9/1981 | Ogawa |
| 4,289,131 | A | 9/1981 | Mueller |
| 4,289,133 | A | 9/1981 | Rothfuss |
| 4,296,881 | A | 10/1981 | Lee |
| 4,304,236 | A | 12/1981 | Conta et al. |
| 4,310,115 | A | 1/1982 | Inoue |
| 4,319,576 | A | 3/1982 | Rothfuss |
| 4,325,377 | A | 4/1982 | Boebel |
| 4,334,539 | A | 6/1982 | Childs et al. |
| 4,349,028 | A | 9/1982 | Green |
| 4,351,466 | A | 9/1982 | Noiles |
| 4,354,628 | A | 10/1982 | Green |
| 4,367,729 | A | 1/1983 | Ogiu |
| 4,379,457 | A | 4/1983 | Gravener et al. |
| 4,383,634 | A | 5/1983 | Green |

(56) References Cited

U.S. PATENT DOCUMENTS

| | | | |
|---|---|---|---|
| 4,391,401 A | 7/1983 | Moshofsky | |
| 4,402,311 A | 9/1983 | Hattori | |
| 4,402,445 A | 9/1983 | Green | |
| 4,419,987 A * | 12/1983 | Ogiu | 600/108 |
| 4,423,730 A | 1/1984 | Gabbay | |
| 4,429,695 A | 2/1984 | Green | |
| 4,442,964 A | 4/1984 | Becht | |
| 4,445,509 A | 5/1984 | Auth | |
| 4,445,892 A | 5/1984 | Hussein et al. | |
| 4,448,188 A | 5/1984 | Loeb | |
| 4,461,305 A | 7/1984 | Cibley | |
| 4,473,077 A | 9/1984 | Noiles et al. | |
| 4,476,863 A | 10/1984 | Kanshin et al. | |
| 4,485,817 A | 12/1984 | Swiggett | |
| 4,487,270 A | 12/1984 | Huber | |
| 4,488,523 A | 12/1984 | Shichman | |
| 4,489,724 A | 12/1984 | Arnegger | |
| 4,489,875 A | 12/1984 | Crawford et al. | |
| 4,494,057 A | 1/1985 | Hotta | |
| 4,494,549 A * | 1/1985 | Namba et al. | 600/109 |
| 4,499,895 A | 2/1985 | Takayama | |
| 4,505,272 A | 3/1985 | Utyamyshev et al. | |
| 4,505,414 A | 3/1985 | Filipi | |
| 4,506,670 A | 3/1985 | Crossley | |
| 4,506,671 A | 3/1985 | Green | |
| 4,513,746 A | 4/1985 | Aranyi et al. | |
| 4,519,532 A | 5/1985 | Foslien | |
| 4,520,817 A | 6/1985 | Green | |
| 4,534,352 A | 8/1985 | Korthoff | |
| 4,534,420 A | 8/1985 | Goldelius | |
| 4,535,773 A | 8/1985 | Yoon | |
| 4,559,928 A | 12/1985 | Takayama | |
| 4,566,620 A | 1/1986 | Green et al. | |
| 4,573,468 A | 3/1986 | Conta et al. | |
| 4,573,622 A | 3/1986 | Green et al. | |
| 4,574,806 A | 3/1986 | McCarthy | |
| 4,576,167 A | 3/1986 | Noiles | |
| 4,589,412 A | 5/1986 | Kensey | |
| 4,589,416 A | 5/1986 | Green | |
| 4,589,582 A | 5/1986 | Bilotti | |
| 4,591,085 A | 5/1986 | Di Giovanni | |
| 4,592,354 A | 6/1986 | Rothfuss | |
| 4,593,679 A | 6/1986 | Collins | |
| 4,603,693 A | 8/1986 | Conta et al. | |
| 4,605,001 A | 8/1986 | Rothfuss et al. | |
| 4,606,343 A | 8/1986 | Conta et al. | |
| 4,607,638 A | 8/1986 | Crainich | |
| 4,610,383 A | 9/1986 | Rothfuss et al. | |
| 4,615,330 A * | 10/1986 | Nagasaki et al. | 600/104 |
| D286,567 S | 11/1986 | Lichtman et al. | |
| 4,631,052 A | 12/1986 | Kensey | |
| 4,633,861 A | 1/1987 | Chow et al. | |
| 4,633,874 A | 1/1987 | Chow et al. | |
| 4,643,190 A | 2/1987 | Heimberger | |
| 4,644,952 A | 2/1987 | Patipa et al. | |
| 4,646,745 A | 3/1987 | Noiles | |
| 4,654,701 A | 3/1987 | Yabe | |
| 4,655,673 A | 4/1987 | Hawkes | |
| 4,657,017 A | 4/1987 | Sorochenko | |
| 4,664,305 A | 5/1987 | Blake, III et al. | |
| 4,667,673 A | 5/1987 | Li | |
| 4,669,471 A | 6/1987 | Hayashi | |
| 4,671,445 A | 6/1987 | Barker et al. | |
| 4,672,961 A | 6/1987 | Davies | |
| 4,674,515 A | 6/1987 | Andou et al. | |
| 4,682,596 A | 7/1987 | Bales et al. | |
| 4,688,555 A | 8/1987 | Wardle | |
| 4,696,667 A | 9/1987 | Masch | |
| 4,700,703 A | 10/1987 | Resnick et al. | |
| 4,703,887 A | 11/1987 | Clanton et al. | |
| 4,705,038 A | 11/1987 | Sjostrom et al. | |
| 4,708,141 A | 11/1987 | Inoue et al. | |
| 4,714,187 A | 12/1987 | Green | |
| 4,715,502 A | 12/1987 | Salmon | |
| 4,728,020 A | 3/1988 | Green et al. | |
| 4,729,763 A | 3/1988 | Henrie | |
| 4,732,156 A | 3/1988 | Nakamura | |
| 4,733,118 A | 3/1988 | Mihalko | |
| 4,742,815 A | 5/1988 | Ninan et al. | |
| 4,752,024 A | 6/1988 | Green et al. | |
| 4,754,909 A | 7/1988 | Barker et al. | |
| 4,756,309 A | 7/1988 | Sachse et al. | |
| 4,760,840 A | 8/1988 | Fournier, Jr. et al. | |
| 4,763,669 A | 8/1988 | Jaeger | |
| 4,767,044 A | 8/1988 | Green | |
| 4,771,774 A | 9/1988 | Simpson et al. | |
| 4,776,506 A | 10/1988 | Green | |
| 4,781,186 A | 11/1988 | Simpson et al. | |
| 4,784,137 A | 11/1988 | Kulik et al. | |
| 4,805,823 A | 2/1989 | Rothfuss | |
| 4,813,928 A | 3/1989 | Abe et al. | |
| 4,815,469 A | 3/1989 | Cohen et al. | |
| 4,817,847 A | 4/1989 | Redtenbacher et al. | |
| 4,819,632 A | 4/1989 | Davies | |
| 4,819,853 A | 4/1989 | Green | |
| 4,841,888 A | 6/1989 | Mills et al. | |
| 4,848,637 A | 7/1989 | Pruitt | |
| 4,858,608 A | 8/1989 | McQuilkin | |
| 4,863,088 A | 9/1989 | Redmond et al. | |
| 4,867,158 A | 9/1989 | Sugg | |
| 4,869,415 A | 9/1989 | Fox | |
| 4,873,977 A | 10/1989 | Avant et al. | |
| 4,887,612 A | 12/1989 | Esser et al. | |
| 4,890,602 A | 1/1990 | Hake | |
| 4,892,244 A | 1/1990 | Fox et al. | |
| 4,893,613 A | 1/1990 | Hake | |
| 4,893,622 A | 1/1990 | Green et al. | |
| 4,903,697 A | 2/1990 | Resnick et al. | |
| 4,907,591 A | 3/1990 | Vasconcellos et al. | |
| 4,907,973 A | 3/1990 | Hon | |
| 4,917,114 A | 4/1990 | Green et al. | |
| 4,919,152 A | 4/1990 | Ger | |
| 4,928,699 A | 5/1990 | Sasai | |
| 4,930,494 A | 6/1990 | Takehana et al. | |
| 4,932,960 A | 6/1990 | Green et al. | |
| 4,936,845 A | 6/1990 | Stevens | |
| 4,941,454 A | 7/1990 | Wood et al. | |
| 4,941,623 A | 7/1990 | Pruitt | |
| 4,943,277 A | 7/1990 | Bolling | |
| 4,944,093 A | 7/1990 | Falk | |
| 4,944,443 A | 7/1990 | Oddsen et al. | |
| 4,955,882 A | 9/1990 | Hakky | |
| 4,955,959 A | 9/1990 | Tompkins et al. | |
| 4,957,499 A | 9/1990 | Lipatov et al. | |
| 4,962,877 A | 10/1990 | Hervas | |
| 4,976,688 A | 12/1990 | Rosenblum | |
| 4,976,710 A | 12/1990 | Mackin | |
| 4,977,900 A | 12/1990 | Fehling et al. | |
| 4,978,049 A | 12/1990 | Green | |
| 4,982,726 A | 1/1991 | Taira | |
| 4,991,764 A | 2/1991 | Mericle | |
| 4,994,060 A | 2/1991 | Rink et al. | |
| 4,995,877 A | 2/1991 | Ams et al. | |
| 5,005,749 A | 4/1991 | Aranyi | |
| 5,018,657 A | 5/1991 | Pedlick et al. | |
| 5,031,814 A | 7/1991 | Tompkins et al. | |
| 5,037,379 A | 8/1991 | Clayman et al. | |
| 5,040,715 A | 8/1991 | Green et al. | |
| 5,059,203 A | 10/1991 | Husted | |
| 5,065,929 A | 11/1991 | Schulze et al. | |
| D322,143 S | 12/1991 | Spreckelmeier | |
| 5,071,430 A | 12/1991 | de Salis et al. | |
| 5,077,506 A | 12/1991 | Krause | |
| 5,084,045 A | 1/1992 | Helenowski | |
| 5,088,819 A * | 2/1992 | Storz | 356/241.1 |
| 5,104,025 A | 4/1992 | Main et al. | |
| 5,108,391 A | 4/1992 | Flachenecker et al. | |
| 5,119,983 A | 6/1992 | Green et al. | |
| 5,129,570 A | 7/1992 | Schulze et al. | |
| 5,133,359 A | 7/1992 | Kedem | |
| 5,133,360 A | 7/1992 | Spears | |
| 5,133,713 A | 7/1992 | Huang et al. | |
| 5,133,729 A | 7/1992 | Sjostrom | |
| 5,139,513 A | 8/1992 | Segato | |

(56) References Cited

U.S. PATENT DOCUMENTS

| | | | |
|---|---|---|---|
| 5,143,082 A | 9/1992 | Kindberg et al. | |
| 5,156,315 A | 10/1992 | Green et al. | |
| 5,157,837 A | 10/1992 | Rose | |
| 5,158,222 A | 10/1992 | Green | |
| 5,170,925 A | 12/1992 | Madden et al. | |
| 5,171,247 A | 12/1992 | Hughett et al. | |
| 5,171,251 A | 12/1992 | Bregen et al. | |
| 5,173,133 A | 12/1992 | Morin et al. | |
| 5,176,687 A | 1/1993 | Hasson et al. | |
| 5,184,602 A * | 2/1993 | Anapliotis et al. | 600/137 |
| 5,186,714 A | 2/1993 | Boudreault et al. | |
| 5,190,542 A | 3/1993 | Nakao et al. | |
| 5,192,292 A | 3/1993 | Cezana et al. | |
| 5,197,649 A | 3/1993 | Bessler et al. | |
| 5,197,968 A | 3/1993 | Clement | |
| 5,201,325 A | 4/1993 | McEwen et al. | |
| 5,201,750 A | 4/1993 | Höcherl et al. | |
| 5,205,459 A | 4/1993 | Brinkerhoff et al. | |
| 5,207,684 A | 5/1993 | Nobles | |
| 5,207,691 A | 5/1993 | Nardella | |
| 5,207,697 A | 5/1993 | Carusillo et al. | |
| 5,215,521 A | 6/1993 | Cochran et al. | |
| 5,217,003 A | 6/1993 | Wilk | |
| 5,217,030 A | 6/1993 | Yoon | |
| 5,217,460 A | 6/1993 | Knoepfler | |
| 5,221,279 A | 6/1993 | Cook et al. | |
| 5,224,951 A | 7/1993 | Freitas | |
| 5,226,426 A | 7/1993 | Yoon | |
| 5,234,439 A | 8/1993 | Wilk et al. | |
| 5,237,884 A | 8/1993 | Seto | |
| 5,249,583 A | 10/1993 | Mallaby | |
| 5,253,793 A | 10/1993 | Green | |
| 5,254,117 A | 10/1993 | Rigby et al. | |
| 5,258,004 A | 11/1993 | Bales et al. | |
| 5,258,007 A | 11/1993 | Spetzler et al. | |
| 5,258,008 A | 11/1993 | Wilk | |
| 5,261,877 A | 11/1993 | Fine et al. | |
| 5,267,997 A | 12/1993 | Farin et al. | |
| 5,268,622 A | 12/1993 | Philipp | |
| 5,271,543 A | 12/1993 | Grant et al. | |
| 5,271,544 A | 12/1993 | Fox et al. | |
| RE34,519 E | 1/1994 | Fox et al. | |
| 5,275,322 A | 1/1994 | Brinkerhoff et al. | |
| 5,275,323 A | 1/1994 | Schulze et al. | |
| 5,275,609 A | 1/1994 | Pingleton et al. | |
| 5,279,565 A | 1/1994 | Klein et al. | |
| 5,285,945 A | 2/1994 | Brinkerhoff et al. | |
| 5,289,963 A | 3/1994 | McGarry et al. | |
| 5,290,299 A | 3/1994 | Fain et al. | |
| 5,290,303 A | 3/1994 | Pingleton et al. | |
| 5,292,053 A | 3/1994 | Bilotti et al. | |
| 5,295,990 A | 3/1994 | Levin | |
| 5,300,087 A | 4/1994 | Knoepfler | |
| 5,307,976 A | 5/1994 | Olson et al. | |
| 5,312,023 A | 5/1994 | Green et al. | |
| 5,312,416 A | 5/1994 | Spaeth et al. | |
| 5,312,434 A | 5/1994 | Crainich | |
| 5,318,221 A | 6/1994 | Green et al. | |
| 5,320,627 A | 6/1994 | Sorensen et al. | |
| 5,322,055 A | 6/1994 | Davison et al. | |
| 5,324,288 A | 6/1994 | Billings et al. | |
| 5,324,300 A | 6/1994 | Elias et al. | |
| 5,326,013 A | 7/1994 | Green et al. | |
| 5,330,471 A | 7/1994 | Eggers | |
| 5,330,483 A | 7/1994 | Heaven et al. | |
| 5,330,486 A | 7/1994 | Wilk | |
| 5,333,773 A | 8/1994 | Main et al. | |
| 5,336,229 A | 8/1994 | Noda | |
| 5,336,237 A | 8/1994 | Chin et al. | |
| 5,342,299 A | 8/1994 | Snoke et al. | |
| 5,342,381 A | 8/1994 | Tidemand | |
| 5,342,382 A | 8/1994 | Brinkerhoff et al. | |
| 5,344,420 A | 9/1994 | Hilal et al. | |
| 5,346,497 A | 9/1994 | Simon et al. | |
| 5,350,104 A | 9/1994 | Main et al. | |
| 5,352,222 A | 10/1994 | Rydell | |
| 5,352,223 A | 10/1994 | McBrayer et al. | |
| 5,352,235 A | 10/1994 | Koros et al. | |
| 5,354,266 A | 10/1994 | Snoke | |
| 5,354,303 A | 10/1994 | Spaeth et al. | |
| 5,356,408 A | 10/1994 | Rydell | |
| 5,358,496 A | 10/1994 | Ortiz et al. | |
| 5,358,506 A | 10/1994 | Green et al. | |
| 5,364,001 A | 11/1994 | Bryan | |
| 5,364,409 A | 11/1994 | Kuwabara et al. | |
| 5,366,133 A | 11/1994 | Geiste | |
| 5,366,476 A | 11/1994 | Noda | |
| 5,368,015 A | 11/1994 | Wilk | |
| 5,368,607 A | 11/1994 | Freitas | |
| 5,380,321 A | 1/1995 | Yoon | |
| 5,383,880 A | 1/1995 | Hooven | |
| 5,387,196 A | 2/1995 | Green et al. | |
| 5,391,156 A | 2/1995 | Hildwein et al. | |
| 5,395,030 A | 3/1995 | Kuramoto et al. | |
| 5,395,033 A | 3/1995 | Byrne et al. | |
| 5,395,369 A | 3/1995 | McBrayer et al. | |
| 5,396,900 A | 3/1995 | Slater et al. | |
| 5,397,046 A | 3/1995 | Savage et al. | |
| 5,400,267 A | 3/1995 | Denen et al. | |
| D357,535 S | 4/1995 | Grant et al. | |
| 5,402,769 A * | 4/1995 | Tsuji | 600/109 |
| 5,403,312 A | 4/1995 | Yates et al. | |
| 5,403,326 A | 4/1995 | Harrison et al. | |
| 5,403,327 A | 4/1995 | Thornton et al. | |
| 5,409,487 A | 4/1995 | Jalbert et al. | |
| 5,411,508 A | 5/1995 | Bessler et al. | |
| 5,413,267 A | 5/1995 | Solyntjes | |
| 5,413,268 A | 5/1995 | Green et al. | |
| 5,415,334 A | 5/1995 | Williamson et al. | |
| 5,425,705 A | 6/1995 | Evard et al. | |
| 5,425,738 A | 6/1995 | Gustafson et al. | |
| 5,425,745 A | 6/1995 | Green et al. | |
| 5,431,322 A | 7/1995 | Green et al. | |
| 5,431,645 A | 7/1995 | Smith et al. | |
| 5,433,721 A | 7/1995 | Hooven et al. | |
| 5,437,636 A | 8/1995 | Snoke et al. | |
| 5,437,684 A | 8/1995 | Calabrese et al. | |
| 5,441,507 A | 8/1995 | Wilk | |
| 5,443,198 A | 8/1995 | Viola et al. | |
| 5,454,825 A | 10/1995 | Van Leeuwen et al. | |
| 5,456,684 A | 10/1995 | Schmidt et al. | |
| 5,460,182 A | 10/1995 | Goodman et al. | |
| 5,464,404 A | 11/1995 | Abela et al. | |
| 5,465,894 A | 11/1995 | Clark et al. | |
| 5,467,911 A | 11/1995 | Tsuruta et al. | |
| 5,472,132 A | 12/1995 | Savage et al. | |
| 5,474,223 A | 12/1995 | Viola et al. | |
| 5,476,206 A | 12/1995 | Green et al. | |
| 5,482,054 A | 1/1996 | Slater et al. | |
| 5,482,197 A | 1/1996 | Green et al. | |
| 5,485,947 A | 1/1996 | Olson et al. | |
| 5,487,499 A | 1/1996 | Sorrentino et al. | |
| 5,487,500 A | 1/1996 | Knodel et al. | |
| 5,496,269 A | 3/1996 | Snoke | |
| 5,496,317 A | 3/1996 | Goble et al. | |
| 5,514,134 A | 5/1996 | Rydell et al. | |
| 5,518,163 A | 5/1996 | Hooven | |
| 5,518,164 A * | 5/1996 | Hooven | 227/5 |
| 5,520,634 A | 5/1996 | Fox et al. | |
| 5,524,180 A | 6/1996 | Wang et al. | |
| 5,527,313 A | 6/1996 | Scott et al. | |
| 5,529,235 A | 6/1996 | Boiarski et al. | |
| 5,531,687 A | 7/1996 | Snoke et al. | |
| 5,533,661 A | 7/1996 | Main et al. | |
| 5,535,937 A | 7/1996 | Boiarski et al. | |
| 5,549,565 A | 8/1996 | Ryan et al. | |
| 5,553,765 A | 9/1996 | Knodel et al. | |
| 5,554,169 A | 9/1996 | Green et al. | |
| RE35,352 E | 10/1996 | Peters | |
| 5,562,677 A | 10/1996 | Hildwein et al. | |
| 5,562,702 A | 10/1996 | Huitema et al. | |
| 5,569,274 A | 10/1996 | Rapacki et al. | |
| 5,571,116 A | 11/1996 | Bolanos et al. | |
| 5,573,543 A | 11/1996 | Akopov et al. | |

(56) References Cited

U.S. PATENT DOCUMENTS

| | | |
|---|---|---|
| 5,578,052 A | 11/1996 | Koros et al. |
| 5,580,067 A | 12/1996 | Hamblin et al. |
| 5,582,611 A | 12/1996 | Tsuruta et al. |
| 5,584,425 A | 12/1996 | Savage et al. |
| 5,584,848 A | 12/1996 | Yoon |
| 5,588,579 A | 12/1996 | Schnut et al. |
| 5,591,186 A | 1/1997 | Wurster et al. |
| 5,597,107 A | 1/1997 | Knodel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,618,303 A | 4/1997 | Marlow et al. |
| 5,618,307 A | 4/1997 | Donlon et al. |
| 5,626,607 A | 5/1997 | Malecki et al. |
| 5,639,008 A | 6/1997 | Gallagher et al. |
| 5,651,780 A | 7/1997 | Jackson et al. |
| 5,653,374 A | 8/1997 | Young et al. |
| 5,653,692 A | 8/1997 | Masterson et al. |
| 5,662,673 A | 9/1997 | Kieturakis |
| 5,665,100 A | 9/1997 | Yoon |
| 5,667,517 A | 9/1997 | Hooven |
| 5,667,526 A | 9/1997 | Levin |
| 5,676,674 A | 10/1997 | Bolanos et al. |
| 5,688,269 A | 11/1997 | Newton et al. |
| 5,693,031 A | 12/1997 | Ryan et al. |
| 5,709,335 A | 1/1998 | Heck |
| 5,713,870 A | 2/1998 | Yoon |
| 5,732,871 A | 3/1998 | Clark et al. |
| 5,732,872 A | 3/1998 | Bolduc et al. |
| 5,735,289 A | 4/1998 | Pfeffer et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,893 A | 5/1998 | Vidal et al. |
| 5,758,814 A | 6/1998 | Gallagher et al. |
| 5,762,458 A | 6/1998 | Wang et al. |
| 5,779,130 A | 7/1998 | Alesi et al. |
| 5,782,396 A | 7/1998 | Mastri et al. |
| 5,782,397 A | 7/1998 | Koukline |
| 5,782,752 A * | 7/1998 | Lichtman et al. ............. 600/137 |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,318 A | 9/1998 | St. Goar et al. |
| 5,807,377 A | 9/1998 | Madhani et al. |
| 5,814,044 A | 9/1998 | Hooven |
| 5,815,640 A | 9/1998 | Wang et al. |
| 5,817,113 A | 10/1998 | Gifford, III et al. |
| 5,823,956 A | 10/1998 | Roth et al. |
| 5,830,191 A | 11/1998 | Hildwein et al. |
| 5,836,503 A | 11/1998 | Ehrenfels et al. |
| 5,846,221 A | 12/1998 | Snoke et al. |
| 5,851,208 A | 12/1998 | Trott |
| 5,855,583 A | 1/1999 | Wang et al. |
| 5,855,590 A | 1/1999 | Malecki et al. |
| 5,857,996 A | 1/1999 | Snoke |
| 5,860,953 A | 1/1999 | Snoke et al. |
| 5,863,366 A | 1/1999 | Snow |
| 5,868,760 A | 2/1999 | McGuckin, Jr. |
| 5,868,779 A | 2/1999 | Ruiz |
| 5,871,471 A | 2/1999 | Ryan et al. |
| 5,878,193 A | 3/1999 | Wang et al. |
| 5,881,943 A | 3/1999 | Heck et al. |
| 5,893,875 A | 4/1999 | O'Connor et al. |
| 5,897,562 A | 4/1999 | Bolanos et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,928,261 A | 7/1999 | Ruiz |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,957,363 A | 9/1999 | Heck |
| 5,957,882 A | 9/1999 | Nita et al. |
| 5,957,884 A | 9/1999 | Hooven |
| 5,976,122 A | 11/1999 | Madhani et al. |
| 5,976,159 A | 11/1999 | Bolduc et al. |
| 5,984,919 A | 11/1999 | Hilal et al. |
| 5,989,274 A | 11/1999 | Davison et al. |
| 5,993,378 A | 11/1999 | Lemelson |
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,493 A | 1/2000 | Snoke |
| 6,017,322 A | 1/2000 | Snoke et al. |
| 6,017,354 A | 1/2000 | Culp et al. |
| 6,059,719 A * | 5/2000 | Yamamoto et al. ............. 600/127 |
| 6,063,095 A | 5/2000 | Wang et al. |
| 6,068,627 A | 5/2000 | Orzulak et al. |
| 6,071,233 A | 6/2000 | Ishikawa et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,464 A | 8/2000 | Shimizu et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |
| 6,159,196 A | 12/2000 | Ruiz |
| 6,171,282 B1 | 1/2001 | Ragsdale |
| 6,174,324 B1 | 1/2001 | Egan et al. |
| 6,179,837 B1 | 1/2001 | Hooven |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| D441,862 S | 5/2001 | Cooper et al. |
| 6,237,605 B1 | 5/2001 | Vaska et al. |
| 6,244,809 B1 | 6/2001 | Wang et al. |
| 6,246,200 B1 | 6/2001 | Blumenkranz et al. |
| 6,251,093 B1 | 6/2001 | Valley et al. |
| D444,555 S | 7/2001 | Cooper et al. |
| 6,261,273 B1 | 7/2001 | Ruiz |
| 6,280,415 B1 | 8/2001 | Johnson |
| 6,309,397 B1 | 10/2001 | Julian et al. |
| 6,312,435 B1 | 11/2001 | Wallace et al. |
| 6,313,868 B1 * | 11/2001 | D'Alfonso et al. ............. 348/72 |
| 6,331,181 B1 | 12/2001 | Tierney et al. |
| 6,346,072 B1 | 2/2002 | Cooper |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,547,721 B1 | 4/2003 | Higuma et al. |
| 6,669,628 B2 | 12/2003 | Abe |
| 6,790,217 B2 | 9/2004 | Schulze et al. |
| 7,252,660 B2 | 8/2007 | Kunz |
| 2001/0001812 A1 | 5/2001 | Valley et al. |
| 2001/0010247 A1 | 8/2001 | Snow |
| 2001/0016725 A1 | 8/2001 | Valley et al. |
| 2001/0016750 A1 | 8/2001 | Malecki et al. |
| 2001/0023334 A1 | 9/2001 | St. Goar et al. |
| 2001/0031975 A1 | 10/2001 | Whitman |
| 2001/0044591 A1 | 11/2001 | Stevens et al. |
| 2002/0013569 A1 | 1/2002 | Sterman et al. |
| 2002/0026094 A1 | 2/2002 | Roth |
| 2002/0029783 A1 | 3/2002 | Stevens et al. |
| 2002/0032451 A1 | 3/2002 | Tierney |
| 2002/0032452 A1 | 3/2002 | Tierney |
| 2002/0042620 A1 | 4/2002 | Julian |
| 2002/0045888 A1 | 4/2002 | Ramans |
| 2002/0055795 A1 | 5/2002 | Niemeyer |

(56) References Cited

U.S. PATENT DOCUMENTS

| | | | |
|---|---|---|---|
| 2002/0068922 A1 | 6/2002 | Peters | |
| 2002/0072736 A1 | 6/2002 | Tierney | |
| 2002/0072741 A1 | 6/2002 | Sliwa et al. | |
| 2002/0087157 A1 | 7/2002 | Sliwa et al. | |
| 2002/0104400 A1 | 8/2002 | Hillgaertner et al. | |
| 2006/0167342 A1* | 7/2006 | Bob et al. | 600/137 |
| 2007/0265499 A1* | 11/2007 | Wood et al. | 600/137 |

FOREIGN PATENT DOCUMENTS

| | | |
|---|---|---|
| DE | 29 03 159 | 7/1980 |
| DE | 3114135 | 10/1982 |
| DE | 33 00 768 | 7/1984 |
| DE | 4312147 | 10/1992 |
| EP | 0 593 920 | 4/1974 |
| EP | 41022 | 12/1981 |
| EP | 93101 | 11/1983 |
| EP | 116220 | 8/1984 |
| EP | 121 474 | 10/1984 |
| EP | 0 156 774 | 10/1985 |
| EP | 0 216 532 | 4/1987 |
| EP | 293123 | 1/1988 |
| EP | 324166 | 7/1989 |
| EP | 324637 | 7/1989 |
| EP | 365153 | 4/1990 |
| EP | 369324 | 5/1990 |
| EP | 373762 | 6/1990 |
| EP | 0 399 701 | 11/1990 |
| EP | 0 514 139 | 11/1992 |
| EP | 0 536 903 | 4/1993 |
| EP | 0 539 762 | 5/1993 |
| EP | 0 552 050 | 7/1993 |
| EP | 0 598 579 | 5/1994 |
| EP | 0 621 006 | 10/1994 |
| EP | 630612 | 12/1994 |
| EP | 639349 | 2/1995 |
| EP | 679367 | 11/1995 |
| EP | 0 705 571 | 4/1996 |
| EP | 552423 | 1/1998 |
| EP | 0 947 167 | 10/1999 |
| EP | 0 653 922 | 12/1999 |
| EP | 653 922 | 12/1999 |
| EP | 581400 | 5/2000 |
| EP | 484677 | 7/2000 |
| EP | 1132051 A2 | 9/2001 |
| FR | 2660851 | 10/1991 |
| GB | 1352554 | 5/1974 |
| GB | 1452185 | 10/1976 |
| GB | 2022421 | 12/1979 |
| GB | 2031733 | 4/1980 |
| GB | 2044108 | 10/1980 |
| GB | 2048685 | 12/1980 |
| GB | 2165559 | 4/1986 |
| GB | 2180455 | 4/1987 |
| NL | 77 11 347 | 4/1979 |
| NL | 7711347 | 4/1979 |
| RU | 659146 | 4/1979 |
| WO | WO 82/03545 | 10/1982 |
| WO | WO 83/00992 | 3/1983 |
| WO | WO 90/05491 | 5/1990 |
| WO | WO 9006085 | 6/1990 |
| WO | WO 91/07136 | 5/1991 |
| WO | WO 92/16141 | 10/1992 |
| WO | WO 93/08754 | 5/1993 |
| WO | WO 93/14706 | 8/1993 |
| WO | WO95/18572 | 7/1995 |
| WO | WO95/35065 | 12/1995 |
| WO | WO 96/18344 | 6/1996 |
| WO | WO98/14129 | 4/1998 |
| WO | WO 95/35065 | 4/1999 |
| WO | WO 00/72765 | 12/2000 |
| WO | WO 01/08572 | 2/2001 |
| WO | WO 01/62163 | 8/2001 |

OTHER PUBLICATIONS

New York Magazine, Jun. 10, 2002 The Best Doctors in New York, p. 80.

* cited by examiner ial.describes a surgical system for powered instruments. The system includes a handpiece containing a motor and including a recess adapted to receive one of a plurality of surgical devices. A pair of reed switches is disposed within the recess, and each of the surgical devices includes one or two magnets adapted to actuate the reed switches in a particular combination when the device is assembled with the handpiece. The combination of reed switches activated by the magnets of the assembled handpiece and surgical device identifies to the system the surgical device so assembled with the handpiece. The number of possible surgical devices identifiable by this system is limited to the four possible combination of up to two magnets.

COUPLINGS FOR INTERCONNECTING COMPONENTS OF AN ELECTRO-MECHANICAL SURGICAL DEVICE

CROSS-REFERENCE TO RELATED APPLICATIONS

The present application is a divisional application of U.S. patent application Ser. No. 10/099,634, filed Mar. 15, 2002 now U.S. Pat. No. 7,951,071 which is a continuation-in-part of U.S. patent application Ser. No. 09/887,789, filed on Jun. 22, 2001, now U.S. Pat. No. 7,032,798 which is a continuation-in-part of U.S. patent application Ser. No. 09/836,781, filed on Apr. 17, 2001, now U.S. Pat. No. 6,981,941 which is a continuation-in-part of U.S. patent application Ser. No. 09/723,715, filed on Nov. 28, 2000, now U.S. Pat. No. 6,793,652 which is a continuation-in-part of U.S. patent application Ser. No. 09/324,451, filed on Jun. 2, 1999, now U.S. Pat. No. 6,315,184 a continuation-in-part of U.S. patent application Ser. No. 09/324,452, filed on Jun. 2, 1999, now U.S. Pat. No. 6,443,973 a continuation-in-part of U.S. patent application Ser. No. 09/351,534, filed on Jul. 12, 1999, now U.S. Pat. No. 6,264,087 a continuation-in-part of U.S. patent application Ser. No. 09/510,923, filed on Feb. 22, 2000, now U.S. Pat. No. 6,517,565 which is a continuation-in-part of U.S. patent application Ser. No. 09/324,452, now U.S. Pat. No. 6,443,973 a continuation-in-part of U.S. patent application Ser. No. 09/510,927, filed on Feb. 22, 2000, now U.S. Pat. No. 6,716,233 which is a continuation-in-part of U.S. patent application Ser. No. 09/324,452, now U.S. Pat. No. 6,443,973 and a continuation-in-part of U.S. patent application Ser. No. 09/510,932, filed on Feb. 22, 2000, now U.S. Pat. No. 6,491,201 each of which is expressly incorporated herein by reference in its entirety.

FIELD OF THE INVENTION

The present invention relates to an electro-mechanical surgical device.

BACKGROUND INFORMATION

The literature is replete with descriptions of surgical devices. For example, U.S. Pat. No. 4,705,038 to Sjostrom et al. describes a surgical system for powered instruments. The system includes a handpiece containing a motor and including a recess adapted to receive one of a plurality of surgical devices. A pair of reed switches is disposed within the recess, and each of the surgical devices includes one or two magnets adapted to actuate the reed switches in a particular combination when the device is assembled with the handpiece. The combination of reed switches activated by the magnets of the assembled handpiece and surgical device identifies to the system the surgical device so assembled with the handpiece. The number of possible surgical devices identifiable by this system is limited to the four possible combination of up to two magnets.

U.S. Pat. No. 4,995,877 to Ams et al. describes a device with a rotationally-driven surgical instrument. The device includes a hand-held element containing a driving motor for driving a tool insert. The device further includes a control unit having a storage unit for storing operational data manually set by the user of the device. Such data may be transferred to a code carrier, which is insertable into a plug-in facility.

U.S. Pat. No. 5,249,583 to Mallaby describes an electronic biopsy instrument with wiperless position sensors. A slotted disc and a cam are affixed to a drive shaft, which is driven by a motor. A pair of sensors is arranged so that each sensor is activated when the slot of the slotted disc is positioned over the sensor to thereby determine the position of a cannula and a stylet of the instrument. The sensors, slotted disc, cam, motor and rechargeable batteries for powering the instrument are contained within a housing of the instrument.

U.S. Pat. No. 5,383,880 to Hooven describes an endoscopic surgical system with sensing means. The instrument includes a motor disposed within a hand-held housing. A sensor is provided in the head of an instrument of the system for sensing the blood oxygen content of adjacent tissue.

Similarly, U.S. Pat. No. 5,395,033 to Byrne et al. describes an endoscopic surgical instrument having a pair of jaws. A permanent magnet is disposed in a distal end of one of the jaws, and a magneto-resistive sensor is disposed in a distal end of the other one of the jaws. The magnet produces a magnetic field between the jaws, and the sensor measures the variations in the magnetic field so that the distance between the jaws may be determined.

U.S. Pat. No. 5,467,911 to Tsuruta et al. describes a surgical device for stapling and fastening body tissues. The device includes an operation section and an insertion section, which is detachably attachable to the operation section.

U.S. Pat. Nos. 5,518,163, 5,518,164 and 5,667,517, all to Hooven, describe an endoscopic surgical system, which includes a motor disposed in a handle portion. A sensing member, which is used to sense the blood oxygen content of adjacent tissue, is disposed in a head of the instrument. A contact is also provided in the head of the instrument. When a firing nut of the system has moved forward in the head to drive and form surgical staples disposed therein, the firing nut engages the contact, thereby reversing the motor to retract the firing nut.

U.S. Pat. No. 5,653,374 to Young et al., U.S. Pat. No. 5,779,130 to Alesi et al. and U.S. Pat. No. 5,954,259 to Viola et al. describe a self-contained powered surgical apparatus, which includes a motor assembly and power source disposed within a hand-held instrument body.

These instruments and systems described above suffer numerous disadvantages. For example, in several of the above-described instruments and systems, a motor is disposed within a handle of the instrument. Due to size considerations, these motors generally provide limited torque. In certain of the instruments and systems described above, a battery is provided within the handle for powering the motor. Such battery systems, however, provide limited electrical power to the motors, further limiting the torque output by the motors.

In addition, it is generally not possible to accurately ascertain the positions of the operative elements of the aforementioned instruments and systems.

A further disadvantage of the above-described instruments and systems is that such instruments and systems typically require manual manipulation and operation. When a motor is provided in the handle of such instruments, manual manipulation and operation is awkward and cumbersome to the operator.

SUMMARY

In one example embodiment of the present invention, a flexible shaft is provided that includes an flexible, elongated outer sheath, the sheath being formed from an autoclavable material, and at least one drive shaft disposed in the outer sheath.

In another example embodiment of the present invention, a flexible shaft is provided, including: a flexible, elongated outer sheath; at least one drive shaft disposed within the outer sheath; and a moisture sensor disposed within the outer sheath configured to detect moisture within the flexible outer sheath.

In still another example embodiment a flexible shaft is provided, including: a flexible, elongated outer sheath; at least one drive shaft disposed within the outer sheath; and a coupling connected to a distal end of the outer sheath.

In yet another example embodiment a shaft for a surgical system is provided, including: a flexible, elongated outer sheath; at least one drive shaft disposed within the outer sheath; and an outer sleeve configured to retain the outer sheath in a predetermined shape.

In still another example embodiment a surgical device is provided, including an electro-mechanical driver device; a flexible, elongated outer sheath connected to the electro-mechanical driver device; and at least one drive shaft disposed within the outer sheath.

BRIEF DESCRIPTION OF THE DRAWINGS

FIG. 9a is a schematic cross-sectional side view of a second example embodiment of a circular surgical stapler attachment used in connection with the electro-mechanical surgical device illustrated in FIG. 1.

FIG. 24b is an assembled view of the example detachable second coupling illustrated in FIG. 24a.

DETAILED DESCRIPTION

Figure 1:
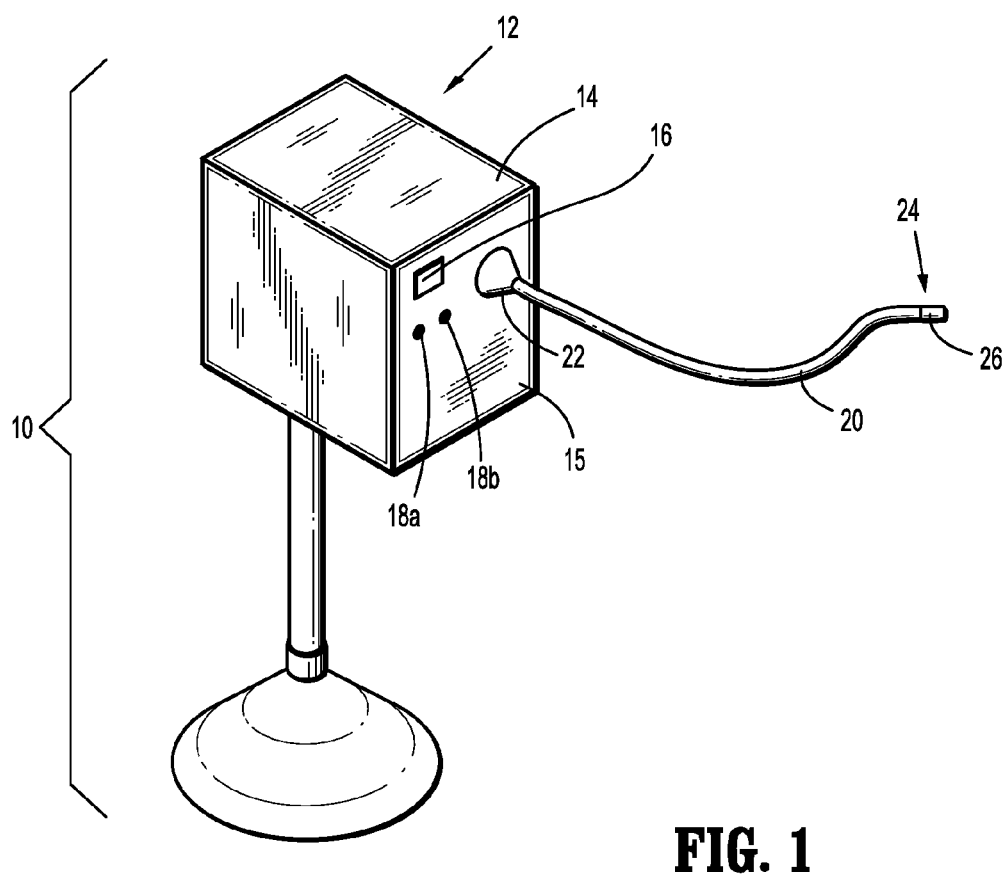
FIG. 1 is a perspective view of an electro-mechanical surgical device according to the present invention.

Those skilled in the art will gain an appreciation of the present invention from a reading of the following description when viewed in conjunction with the accompanying drawings of FIGS. 1 to 32, inclusive. The individual reference characters designate the same or similar elements throughout the several views.

Referring to FIG. 1, there is seen a perspective view of an electromechanical surgical device 10 according to an example embodiment of the present invention. Electro-mechanical surgical device 10 may include, for example, a remote power console 12, which includes a housing 14 having a front panel 15. Mounted on front panel 15 are a display device 16 and indicators 18a, 18b, which are more fully described hereinbelow. A shaft 20 may extend from housing 14 and may be detachably secured thereto via a first coupling 22. The shaft 20 may be flexible, rigid, articulable, articulatable, etc. Although shaft 20 is referred to below as a flexible shaft 20, it should be understood that reference to a flexible shaft 20 is merely one example embodiment of the shaft 20 and that shaft 20 is in no way limited to a flexible arrangement. The distal end 24 of flexible shaft 20 may include a second coupling 26 adapted to detachably secure a surgical instrument or attachment to the distal end 24 of flexible shaft 20. The surgical instrument or attachment may be, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. patent application Ser. No. 09/324,451, entitled "A Stapling Device for Use with an Electromechanical Driver Device for Use with Anastomosing, Stapling, and Resecting Instruments," U.S. patent application Ser. No. 09/324,452, entitled "Electromechanical Driver Device for Use with Anastomosing, Stapling, and Resecting Instruments," U.S. patent application Ser. No. 09/351, 534, entitled "Automated Surgical Stapling System," U.S. patent application Ser. No. 09/510,926, entitled "A Vessel and Lumen Expander Attachment for Use with an Electromechanical Driver Device," U.S. patent application Ser. No. 09/510,927, entitled "Electromechanical Driver and Remote Surgical Instruments Attachment Having Computer Assisted Control Capabilities," U.S. patent application Ser. No. 09/510,931, entitled "A Tissue Stapling Attachment for Use with an Electromechanical Driver Device," U.S. patent application Ser. No. 09/510,932, entitled "A Fluid Delivery Mechanism for Use with Anastomosing, Stapling, and Resecting Instruments," and U.S. patent application Ser. No. 09/510,933, entitled "A Fluid Delivery Device for Use with Anastomosing, Stapling, and Resecting Instruments," each of which is expressly incorporated herein in its entirety by reference thereto.

Figure 2:
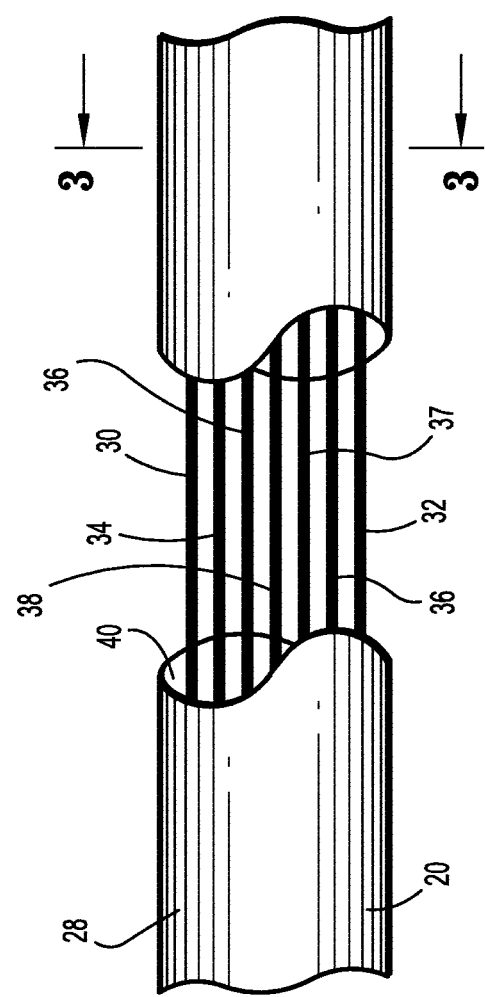
FIG. 2 is a side elevational view, partially in section, of a flexible shaft of the electro-mechanical surgical device illustrated in FIG. 1.
Figure 3:
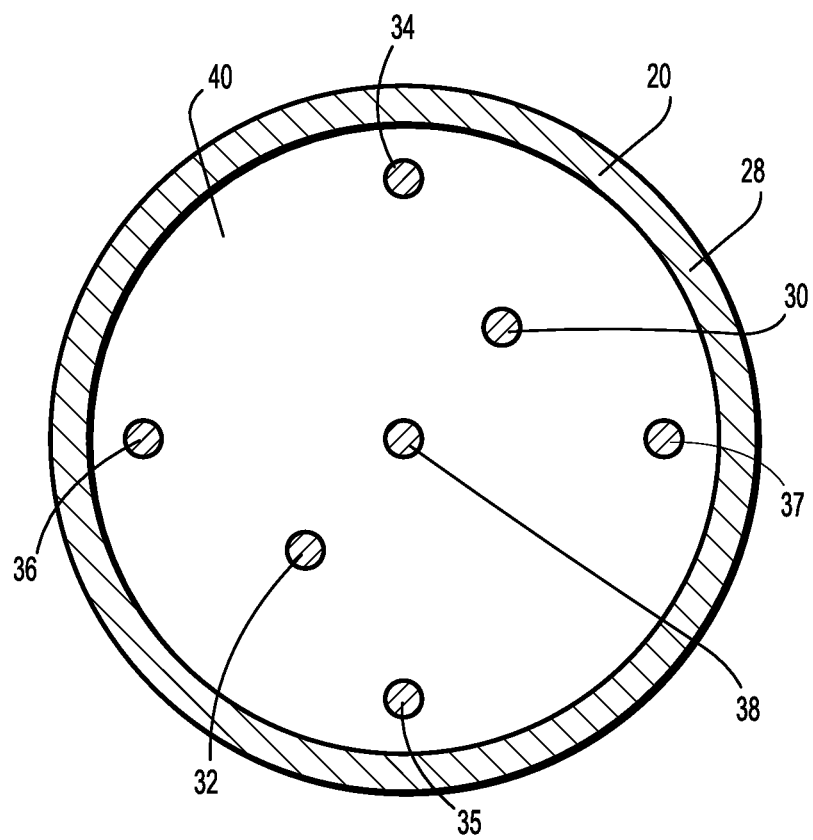
FIG. 3 is a cross-sectional view of the flexible shaft taken along the line 3-3 shown in FIG. 2.

Referring to FIG. 2, there is seen a side view, partially in section, of flexible shaft 20. According to one embodiment, flexible shaft 20 includes a tubular sheath 28, which may include a coating or other sealing arrangement to provide a fluid-tight seal between the interior channel 40 thereof and the environment. Sheath 28 may be formed of a tissue-compatible, sterilizable elastomeric material. The sheath 28 may also be formed of a material that is autoclavable. The sheath 28 may be formed of a material having a high or relatively high lubricity. For example, sheath 28 may include Teflon™ (i.e., a fluoropolymer, e.g., polytetrafluoroethylene— "PTFE"), silicone, a Teflon™/silicone combination, such as, for example, SIL-KORE™ (made by W.L. Gore & Associates). Disposed within the interior channel 40 of flexible shaft 20, and extending along the entire length thereof, may be a first rotatable drive shaft 30, a second rotatable drive shaft 32, a first steering cable 34, a second steering cable 35, a third steering cable 36, a fourth steering cable 37 and a data transfer cable 38. FIG. 3 is a cross-sectional view of flexible shaft 20 taken along the line 3-3 shown in FIG. 2 and further illustrates the several cables 30, 32, 34, 35, 36, 37, 38. Each distal end of the steering cables 34, 35, 36, 37 is affixed to the distal end 24 of the flexible shaft 20. Each of the several cables 30, 32, 34, 35, 36, 37, 38 may be contained within a respective sheath.

The first rotatable drive shaft 30 and the second rotatable drive shaft 32 may be configured, for example, as highly flexible drive shafts, such as, for example, braided or helical drive cables. It should be understood that such highly flexible drive cables may have limited torque transmission characteristics and capabilities. It should also be understood that surgical instruments, such as the circular surgical stapler attachment 250 illustrated in FIG. 9a and the circular surgical stapler attachment 2250 illustrated in FIGS. 9b and 9c and described below, or other attachments detachably attachable to the flexible shaft 20 may require a higher torque input than the torque transmittable by the drive shafts 30, 32. The drive shafts 30, 32 may thus be configured to transmit low torque but high speed, the high speed/low torque being converted to low speed/high torque by gearing arrangements disposed, for example, at the distal end and/or the proximal end of the drive flexible shaft 20, in the surgical instrument or attachment and/or in the remote power console 12. It should be appreciated that such gearing arrangement(s) may be provided at any suitable location along the power train between the motors disposed in the housing 14 and the attached surgical instrument or other attachment detachably attachable to the flexible shaft 20. Such gearing arrangement(s) may be provided in the surgical instrument or other attachment detachably attachable to the flexible shaft 20. Such gearing arrangement(s) may include, for example, a spur gear arrangement, a planetary gear arrangement, a harmonic gear arrangement, cycloidal drive arrangement, an epicyclic gear arrangement, etc. An example embodiment of a circular surgical stapler attachment 2250 having a gearing arrangement for converting high speed/low torque to low speed/high torque is illustrated in FIGS. 9b and 9c and described hereinbelow.

Figure 4:
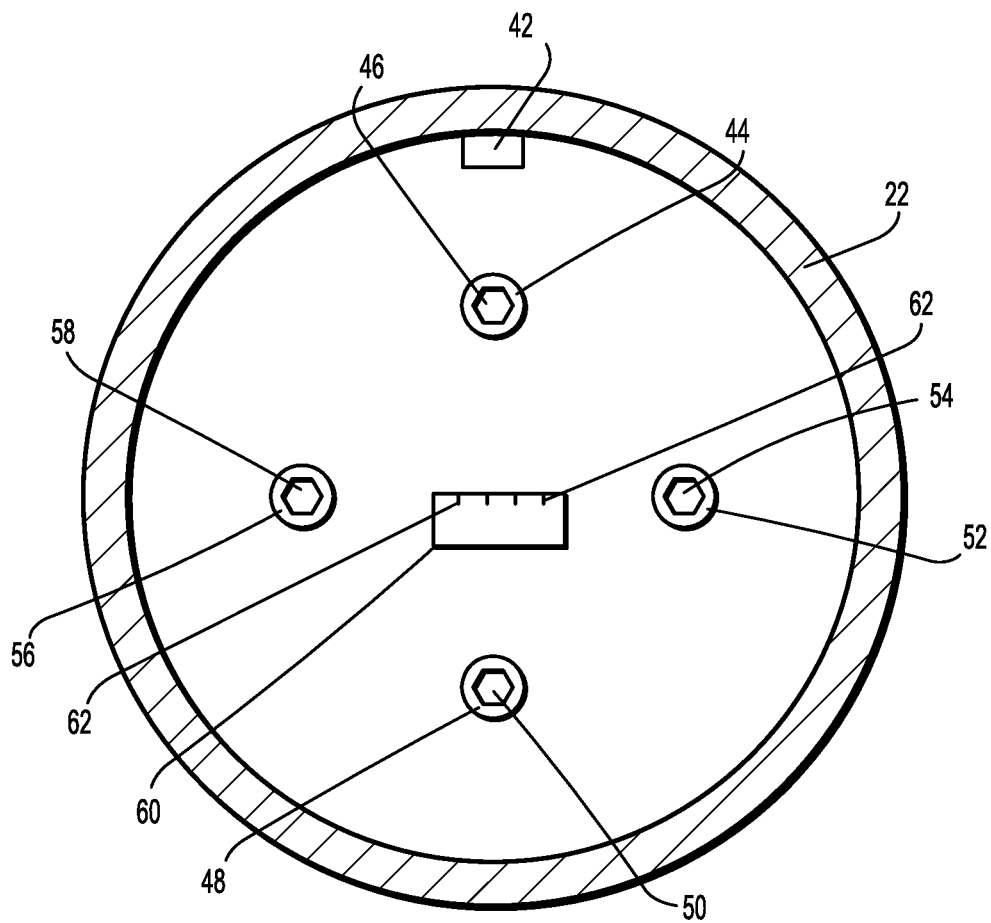
FIG. 4 is a rear end view of a first coupling of the flexible shaft illustrated in FIG. 2.

Referring now to FIG. 4, there is seen a rear end view of first coupling 22. First coupling 22 includes a first connector 44, a second connector 48, a third connector 52 and a fourth connector 56, each rotatably secured to first coupling 22. Each of the connectors 44, 48, 52, 56 includes a respective recess 46, 50, 54, 58. As shown in FIG. 4, each recess 46, 50, 54, 58 may be hexagonally shaped. It should be appreciated, however, that the recesses 46, 50, 54, 58 may have any shape and configuration to non-rotatably couple and rigidly attach the connectors 44, 48, 52, 56 to respective drive shafts of the motor arrangement contained within the housing 12, as more fully described below. It should be appreciated that complementary projections may be provided on respective drive shafts of the motor arrangement to thereby drive the drive elements of the flexible shaft 20 as described below. It should also be appreciated that the recesses may be provided on the drive shafts and complementary projections may be provided on the connectors 44, 48, 52, 56. Any other coupling arrangement configured to non-rotatably and releasably couple the connectors 44, 48, 52, 56 and the drive shafts of the motor arrangement may be provided.

One of the connectors 44, 48, 52, 56 is non-rotatably secured to the first drive shaft 30, and another one of the connectors 44, 48, 52, 56 is non-rotatably secured to the second drive shaft 32. The remaining two of the connectors 44, 48, 52, 56 engage with transmission elements configured to apply tensile forces on the steering cables 34, 35, 36, 37 to thereby steer the distal end 24 of the flexible shaft 20. The data transfer cable 38 is electrically and logically connected with data connector 60. Data connector 60 includes, for example, electrical contacts 62, corresponding to and equal in number to the number of individual wires contained in the data cable 38. First coupling 22 includes a key structure 42 to properly orient the first coupling 22 to a mating and complementary coupling arrangement disposed on the housing 12. Such key structure 42 may be provided on either one, or both, of the first coupling 22 and the mating and complementary coupling arrangement disposed on the housing 12. First coupling 22 may include a quick-connect type connector, which may use, for example, a simple pushing motion to engage the first coupling 22 to the housing 12. Seals may be provided in conjunction with any of the several connectors 44, 48, 52, 56, 60 to provide a fluid-tight seal between the interior of first coupling 22 and the environment.

Figure 5:
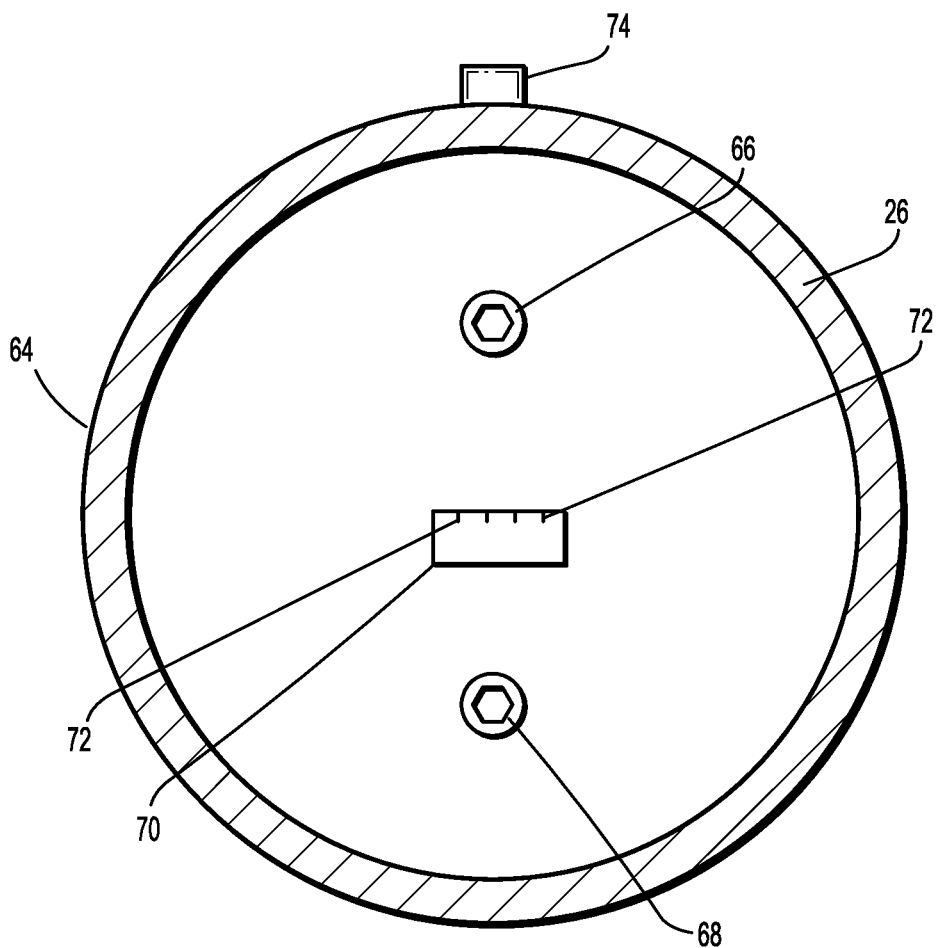
FIG. 5 is a front end view of a second coupling of the flexible shaft illustrated in FIG. 2.

Referring now to FIG. 5, there is seen a front end view of the second coupling 26 of flexible shaft 20. Second coupling 26 includes a first connector 66 and a second connector 68, each being rotatably secured to the second coupling 26 and each being non-rotatably secured to a distal end of a respective one of the first and second drive shafts 30, 32. A quick-connect type fitting 64 is provided on the second coupling 26 for detachably securing the surgical instrument or attachment thereto. The quick-connect type fitting 64 may be, for example, a rotary quick-connect type fitting, a bayonet type fitting, etc. A key structure 74 is provided on the second coupling 26 for properly aligning the surgical instrument or attachment to the second coupling 26. The key structure or other arrangement for properly aligning the surgical instrument or attachment to the flexible shaft 20 may be provided on either one, or both, of the second coupling 26 and the surgical instrument or attachment. In addition, the quick-connect type fitting may be provided on the surgical instrument or attachment. A data connector 70, having electrical contacts 72, is also provided in the second coupling 26. Like the data connector 60 of first coupling 22, the data connector 70 of second coupling 26 includes contacts 72 electrically and logically connected to the respective wires of data transfer cable 38 and contacts 62 of data connector 60. Seals may be provided in conjunction with the connectors 66, 68, 70 to provide a fluid-tight seal between the interior of second coupling 26 and the environment.

Disposed within housing 14 of the remote power console 12 are electromechanical driver elements configured to drive the drive shafts 30, 32 and the steering cables 34, 35, 36, 37 to thereby operate the electro-mechanical surgical device 10 and the surgical instrument or attachment attached to the second coupling 26. In the example embodiment illustrated schematically in FIG. 6, five electric motors 76, 80, 84, 90, 96, each operating via a power source, may be disposed in the remote power console 12. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 6:
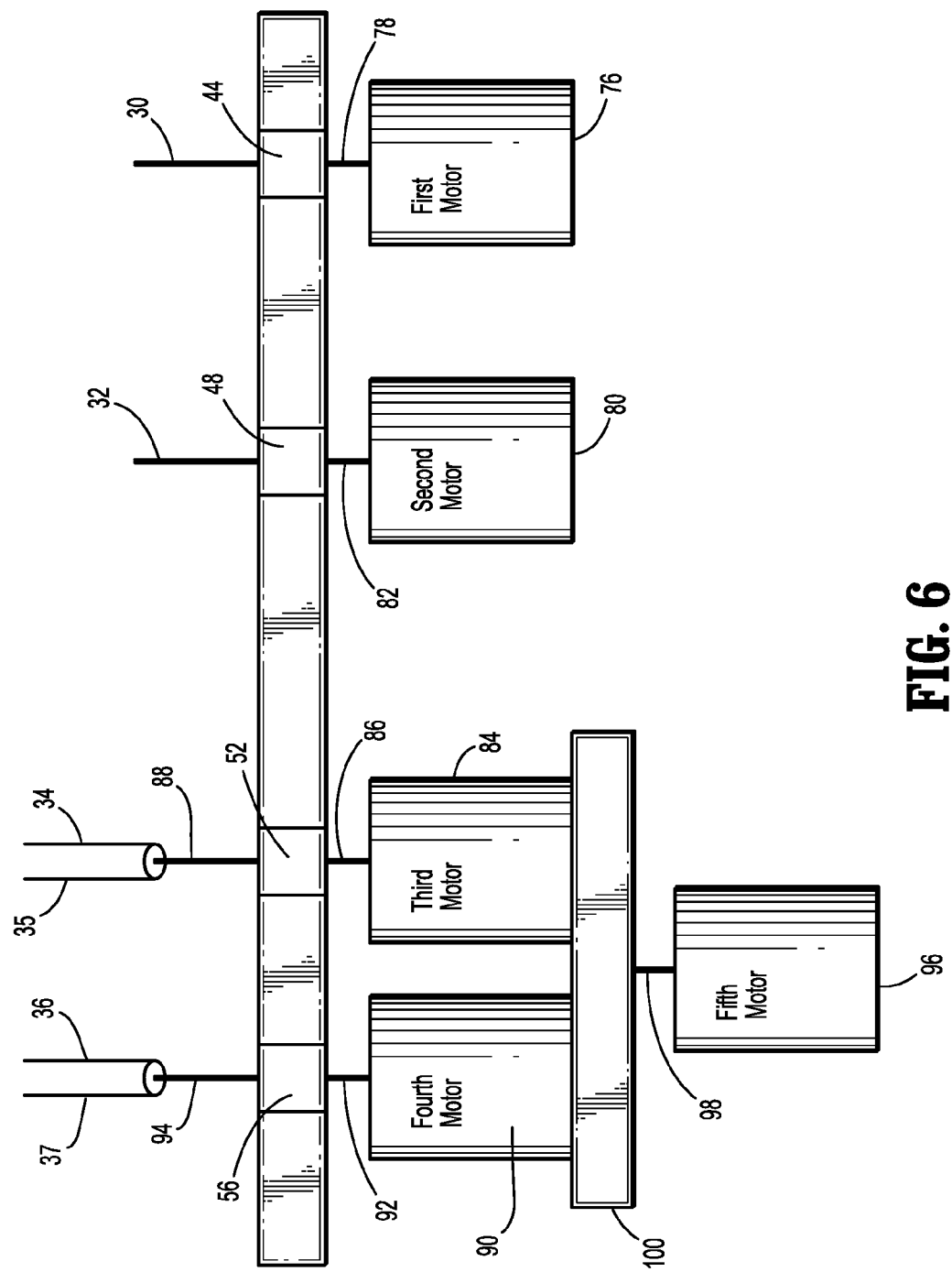
FIG. 6 is a schematic view illustrating a motor arrangement of the electromechanical surgical device illustrated in FIG. 1.

FIG. 6 illustrates schematically one possible arrangement of motors. An output shaft 78 of a first motor 76 engages with the first connector 44 of the first coupling 22 when the first coupling 22, and, therefore, flexible shaft 20, is engaged with the housing 14 to thereby drive the first drive shaft 30 and first connector 66 of second coupling 26. Similarly, an output shaft 82 of a second motor 80 engages the second connector 48 of first coupling 22 when first coupling 22, and, therefore, flexible shaft 20 is engaged with the housing 14 to thereby drive the second drive shaft 32 and second connector 68 of second coupling 26. An output shaft 86 of a third motor 84 engages the third connector 52 of the first coupling 22 when the first coupling 22, and, therefore, flexible shaft 20, is engaged with the housing 14 to thereby drive the first and second steering cables 34, 35 via a first pulley arrangement 88. An output shaft 92 of a fourth motor 90 engages the fourth connector 56 of the first coupling 22 when the first coupling 22, and, therefore, flexible shaft 20, is engaged with the housing 14 to thereby drive the third and fourth steering cables 36, 37 via a second pulley arrangement 94. The third and fourth motors 84, 90 may be secured on a carriage 100, which is selectively movable via an output shaft 98 of a fifth motor 96 between a first position and a second position to selectively engage and disengage the third and fourth motors 84, 90 with the respective pulley arrangement 88, 94 to thereby permit the flexible shaft 20 to become taut and steerable or limp as necessary. It should be appreciated that other mechanical, electrical or electro-mechanical mechanisms may be used to selectively engage and disengage the steering mechanism. The motors may be arranged and configured as described, for example, in U.S. patent application Ser. No. 09/510,923, entitled "A Carriage Assembly for Controlling a Steering Wire Mechanism Within a Flexible Shaft," which is expressly incorporated herein in its entirety by reference thereto.

It should be appreciated, that any one or more of the motors 76, 80, 84, 90, 96 may be high-speed/low-torque motors or low-speed/high-torque motors. As indicated above, the first rotatable drive shaft 30 and the second rotatable drive shaft 32 may be configured to transmit high speed and low torque. Thus, the first motor 76 and the second motor 80 may be configured as high-speed/low-torque motors. Alternatively, the first motor 76 and the second motor 80 may be configured as low-speed/high-torque motors with a torque-reducing/speed-increasing gear arrangement disposed between the first motor 76 and the second motor 80 and a respective one of the first rotatable drive shaft 30 and the second rotatable drive shaft 32. Such torque-reducing/speed-increasing gear arrangement may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 12 or in the proximal end of the flexible shaft 20, such as, for example, in the first coupling 22. It should be appreciated that the gear arrangement(s) are provided at the distal and/or proximal ends of the first rotatable drive shaft 30 and/or the second rotatable drive shaft 32 to prevent windup and breakage thereof.

Figure 7:
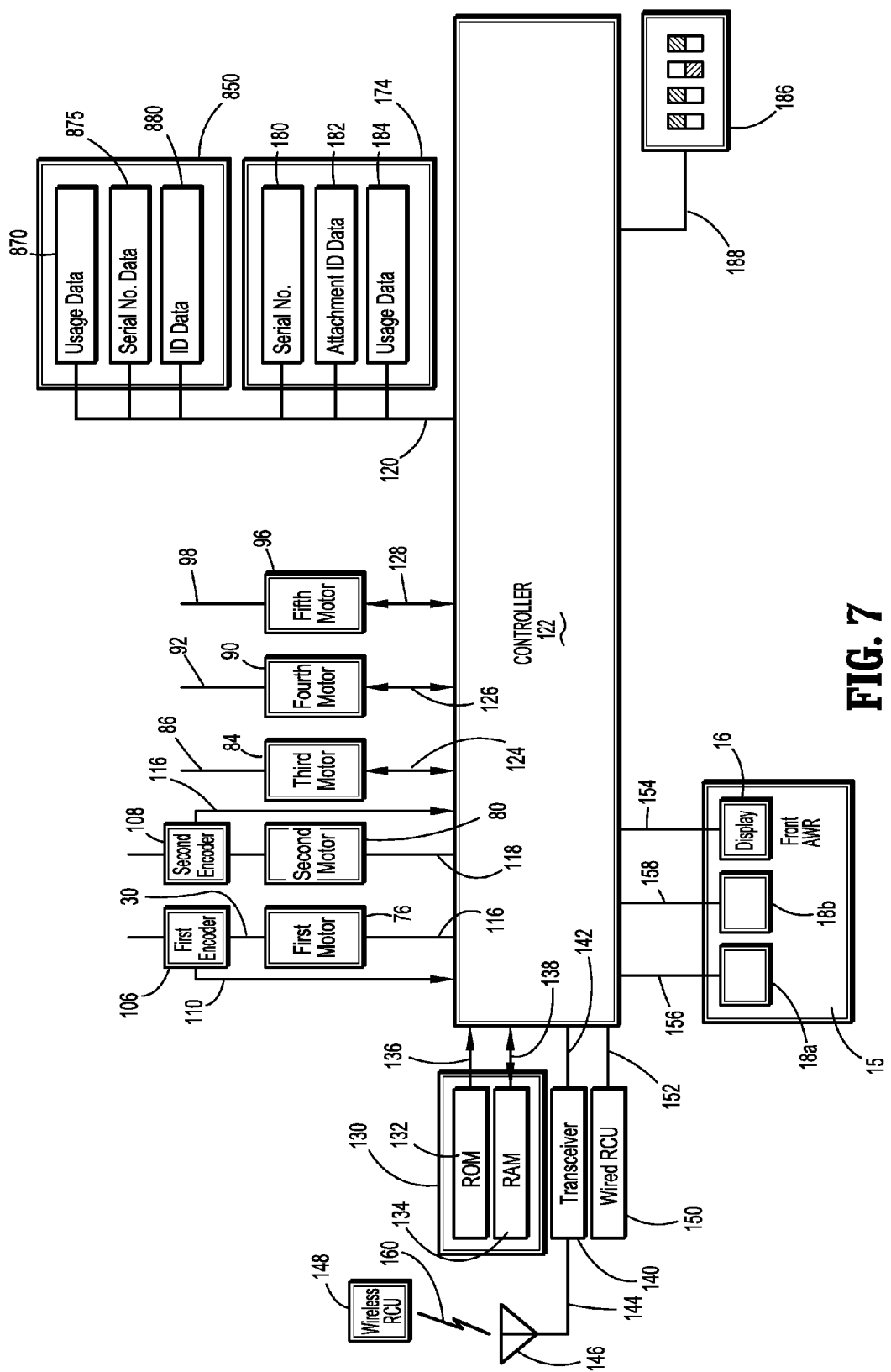
FIG. 7 is a schematic view of the electro-mechanical surgical device illustrated in FIG. 1.

Referring now to FIG. 7, there is seen a schematic view of the electromechanical surgical device 10. A controller 122 is provided in the housing 14 of remote power console 12 and is configured to control all functions and operations of the electro-mechanical surgical device 10 and any surgical instrument or attachment attached to the flexible shaft 20. A memory unit 130 is provided and may include memory devices, such as, a ROM component 132 and/or a RAM component 134. ROM component 132 is in electrical and logical communication with controller 122 via line 136, and RAM component 134 is in electrical and logical communication with controller 122 via line 138. RAM component 134 may include any type of random-access memory, such as, for example, a magnetic memory device, an optical memory device, a magneto-optical memory device, an electronic memory device, etc. Similarly, ROM component 132 may include any type of read-only memory, such as, for example, a removable memory device, such as a PC-Card or PCMCIA-type device. It should be appreciated that ROM component 132 and RAM component 134 may be embodied as a single unit or may be separate units and that ROM component 132 and/or RAM component 134 may be provided in the form of a PC-Card or PCMCIA-type device. Controller 122 is further connected to front panel 15 of housing 14 and, more particularly, to display device 16 via line 154 and indicators 18a, 18b via respective lines 156, 158. Lines 116, 118, 124, 126, 128 electrically and logically connect controller 122 to first, second, third, fourth and fifth motors 76, 80, 84, 90, 96, respectively. A wired remote control unit ("RCU") 150 is electrically and logically connected to controller 122 via line 152. A wireless RCU 148 is also provided and communicates via a wireless link 160 with a receiving/sending unit 146 connected via line 144 to a transceiver 140. The transceiver 140 is electrically and logically connected to controller 122 via line 142. Wireless link 160 may be, for example, an optical link, such as an infrared link, a radio link or any other form of wireless communication link.

A switch device 186, which may be, for example, an array of DIP switches, may be connected to controller 122 via line 188. Switch device 186 may be used, for example, to select one of a plurality of languages used in displaying messages and prompts on the display device 16. The messages and prompts may relate to, for example, the operation and/or the status of the electro-mechanical surgical device 10 and/or to any surgical instrument or attachment attached thereto, According to the example embodiment of the present invention, a first encoder 106 is provided within the second coupling 26 and is configured to output a signal in response to and in accordance with the rotation of the first drive shaft 30. A second encoder 108 is also provided within the second coupling 26 and is configured to output a signal in response to and in accordance with the rotation of the second drive shaft 32. The signal output by each of the encoders 106, 108 may represent the rotational position of the respective drive shaft 30, 32 as well as the rotational direction thereof. Such encoders 106, 108 may be, for example, Hall-effect devices, optical devices, etc. Although the encoders 106, 108 are described as being disposed within the second coupling 26, it should be appreciated that the encoders 106, 108 may be provided at any location between the motor system and the surgical instrument or attachment. It should be appreciated that providing the encoders 106, 108 within the second coupling 26 or at the distal end of the flexible shaft 20 provides for an accurate determination of the drive shaft rotation. If the encoders 106, 108 are disposed at the proximal end of the flexible shaft 20, windup of the first and second rotatable drive shafts 30, 32 may result in measurement error.

Figure 8:
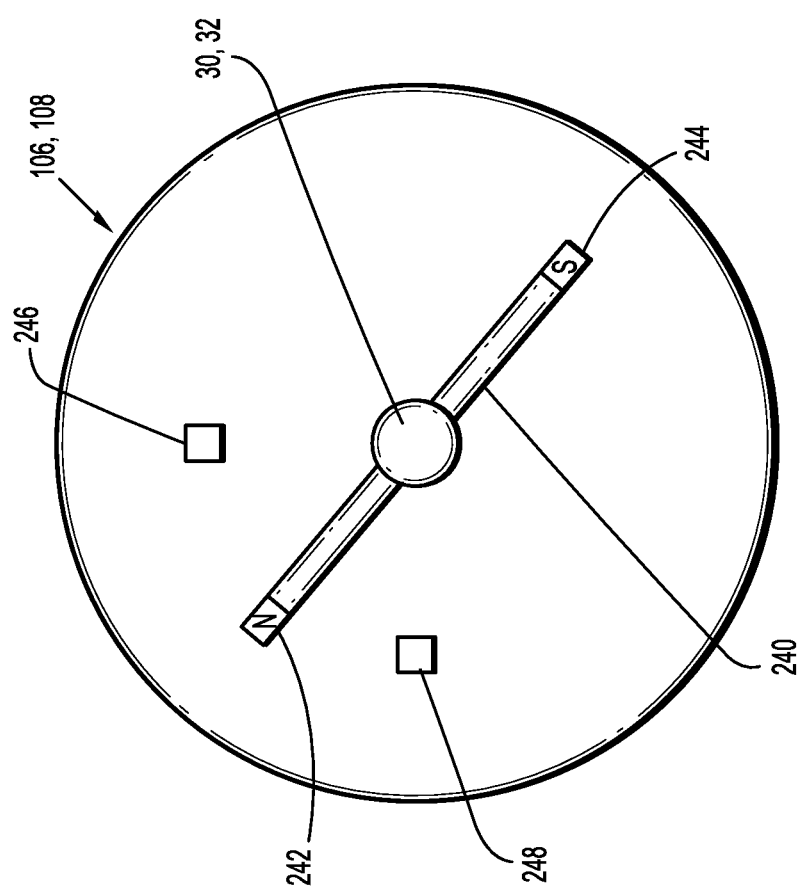
FIG. 8 is a schematic view of an encoder of the flexible shaft illustrated in FIGS. 2 and 3.

FIG. 8 is a schematic view of an encoder 106, 108, which includes a Hall-effect device. Mounted non-rotatably on drive shaft 30, 32 is a magnet 240 having a north pole 242 and a south pole 244. The encoder 106, 108 further includes a first sensor 246 and second sensor 248, which are disposed approximately 90° apart relative to the longitudinal, or rotational, axis of drive shaft 30, 32. The output of the sensors 246, 248 is persistent and changes its state as a function of a change of polarity of the magnetic field in the detection range of the sensor. Thus, based on the output signal from the encoders 106, 108, the angular position of the drive shaft 30, 32 may be determined within one-quarter revolution and the direction of rotation of the drive shaft 30, 32 may be determined. The output of each encoder 106, 108 is transmitted via a respective line 110, 112 of data transfer cable 38 to controller 122. The controller 122, by tracking the angular position and rotational direction of the drive shafts 30, 32 based on the output signal from the encoders 106, 108, can thereby determine the position and/or state of the components of the surgical instrument or attachment connected to the electro-mechanical surgical device 10. That is, by counting the revolutions of the drive shaft 30, 32, the controller 122 can determine the position and/or state of the components of the surgical instrument or attachment connected to the electro-mechanical surgical device 10.

Figure 9A:
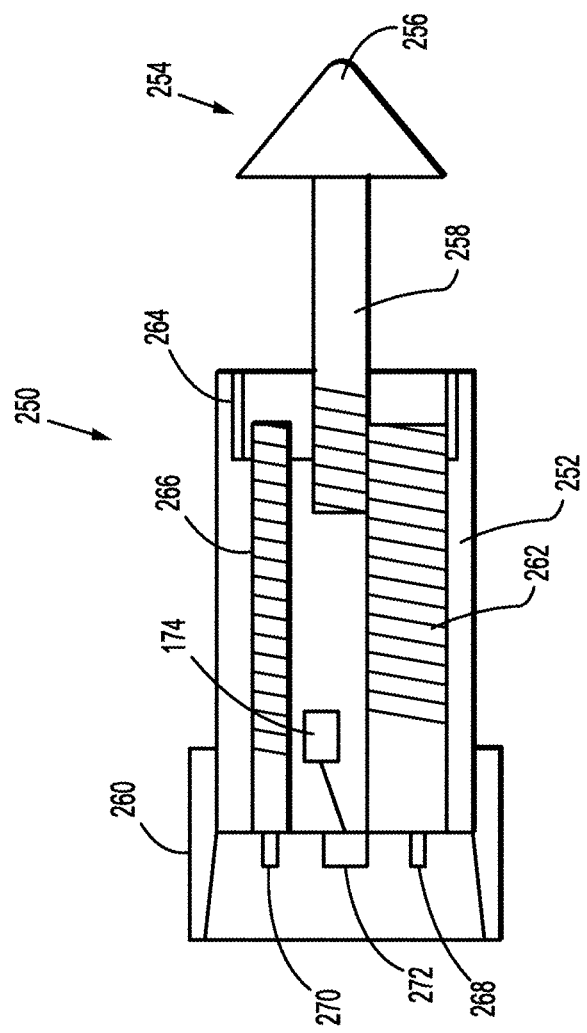
FIG. 9a is a schematic cross-sectional side view of a first example embodiment of a circular surgical stapler attachment used in connection with the electro-mechanical surgical device illustrated in FIG. 1.
Figure 9B:
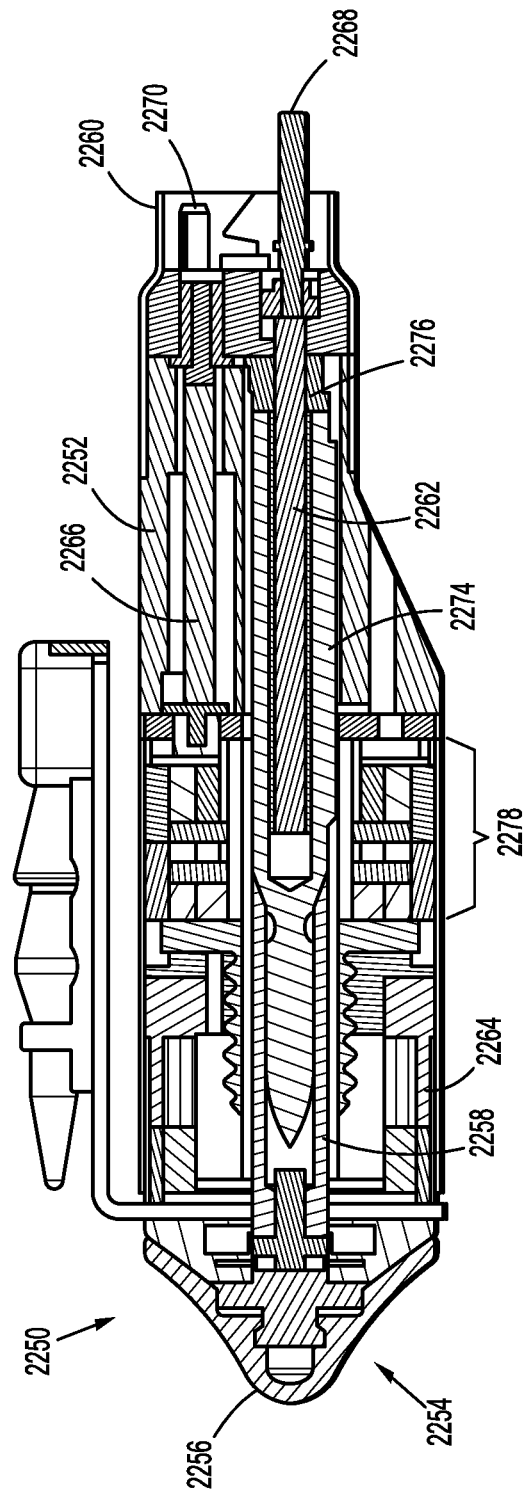
FIG. 9c is an exploded view of an example embodiment of a gear arrangement of the second example embodiment of the circular surgical stapler attachment illustrated in FIG. 9b.
Figure 9C:
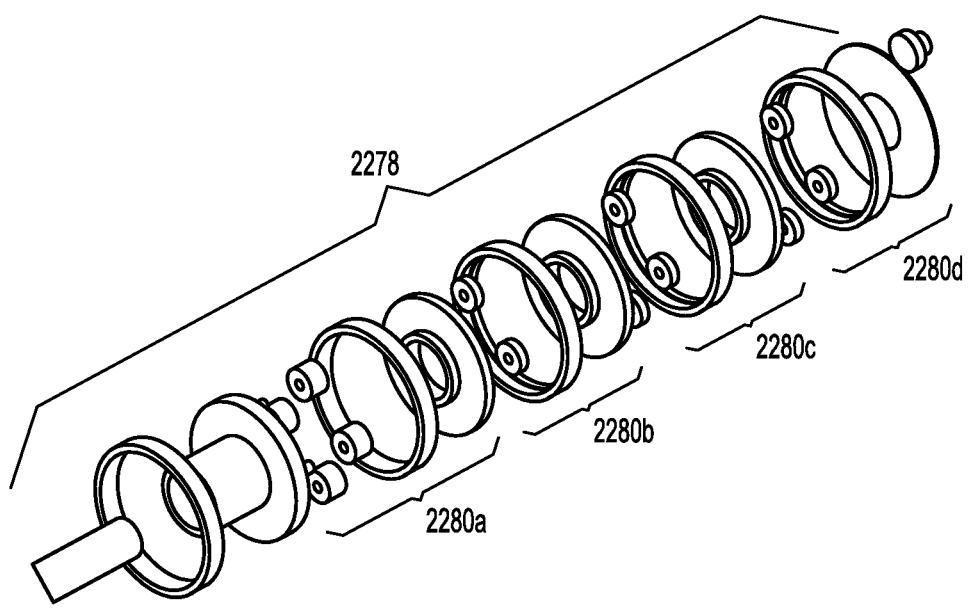

For example, in a circular surgical stapler attachment 250, such as that shown schematically in cross-section in FIG. 9a, the circular surgical stapler attachment 250 includes a coupling 260 adapted by size and configuration to cooperate with the second coupling 26 of flexible shaft 20 to detachably attach the circular surgical stapler attachment 250 thereto. Circular surgical stapler attachment 250 includes an anvil portion 254 having an anvil 256 mounted on the distal end of an anvil stem 258. The anvil stem 258 is extended and retracted by the operation of an anvil drive shaft 262, which is rotatably secured within the body portion 252 of the circular surgical stapler attachment 250. A proximal end of the anvil drive shaft 262 includes a first connector 268 adapted by size and configuration to couple with the first connector 66 of second coupling 26. Circular surgical stapler attachment 250 further includes a staple driver/cutter 264 driven by the rotation of a staple driver/cutter drive shaft 266. The proximal end of the staple driver/cutter drive shaft 266 includes a second connector 270, which is adapted by size and configuration to couple with the second connector 68 of second coupling 26.

The extension and retraction of the anvil 256 is effected by the operation of the first motor 76, and the extension and retraction of the staple driver/cutter 264 is effected by the operation of the second motor 80. The pitch of the anvil drive shaft 262 and the pitch of the stapler driver/cutter drive shaft 266 are predetermined and known quantities. That is, the advancement distance of the anvil 256 and the staple driver/cutter 264 are functions of, and ascertainable on the basis of, the rotation of the respective drive shaft 30, 32. By ascertaining an absolute position of the anvil 256 and the staple driver/cutter 264 at a point in time, the relative displacement of the anvil 256 and staple driver/cutter 264, based on the output signal from the encoders 106, 108 and the known pitches of the anvil drive shaft 262 and staple driver/cutter drive shaft 266, may be used to ascertain the absolute position of the anvil 256 and staple driver/cutter 264 at all times thereafter. The absolute position of the anvil 256 and staple driver/cutter 264 may be fixed and ascertained at the time that the circular surgical stapler attachment 250 is first coupled to the flexible shaft 20. Alternatively, the position of the anvil 256 and the staple driver/cutter 264 relative to, for example, the body portion 252 may be determined based on the output signal from the encoders 106, 108.

Circular surgical stapler attachment 250 further includes a data connector 272 adapted by size and configuration to electrically and logically connect to connector 70 of second coupling 26. In the example embodiment, data connector 272 includes contacts (not shown) equal in number to the number of leads 72 of connector 70. Contained within the circular surgical stapler attachment 250 is a memory unit 174 electrically and logically connected with the data connector 272. Memory unit 174 may be in the form of, for example, an EEPROM, EPROM, etc. and may be contained, for example, within the body portion 252 of circular surgical stapler attachment 250.

FIG. 9b is a schematic cross-sectional view of a second example embodiment of a circular surgical stapler attachment 2250. The circular surgical stapler attachment 2250 includes a coupling 2260 adapted by size and configuration to cooperate with the second coupling 26 of flexible shaft 20 to detachably attach the circular surgical stapler attachment 2250 thereto. Circular surgical stapler attachment 2250 includes an anvil portion 2254 having an anvil 2256 mounted on the distal end of an anvil stem 2258. The anvil stem 2258 may be detachably secured to a trocar 2274. The anvil stem 2258 is extended and retracted by the operation of an anvil drive shaft 2262, which is rotatably secured within the body portion 2252 of the circular surgical stapler attachment 2250. The anvil drive shaft 2262 may be externally threaded, and the trocar 2274 may be internally threaded at the proximal end 2276 thereof so that rotation of the anvil drive shaft 2262 causes the extension and retraction of the anvil stem 2262. A proximal end of the anvil drive shaft 2262 includes a first connector 2268 adapted by size and configuration to couple with the first connector 66 of second coupling 26. Circular surgical stapler attachment 2250 further includes a staple driver/cutter 2264, which is driven by the rotation of a staple driver/cutter drive shaft 2266. The proximal end of the staple driver/cutter drive shaft 2266 includes a second connector 2270, which is adapted by size and configuration to couple with the second connector 68 of the second coupling 26. A gearing arrangement 2278 is disposed between the staple driver/cutter drive shaft 2266 and the staple driver/cutter 2264. The gearing arrangement 2278 may include, for example, a planetary gear arrangement, a harmonic gear arrangement, cycloidal drive arrangement, an epicyclic gear arrangement, etc., which is configured to convert the high-speed/low-torque transmitted by the second rotating drive shaft 32 to low-speed/high-torque for ejecting and forming the staples, as more fully described herein. FIG. 9c is an exploded view of the gearing arrangement 2278, which includes a planetary gear arrangement, namely four sets of planetary gears 2280a, 2280b, 2280c, 2280d. The operation of the second example embodiment of the circular surgical stapler attachment 2250 is similar to the operation of the first example embodiment of the circular surgical stapler attachment 250 as more fully set forth above.

Figure 10:
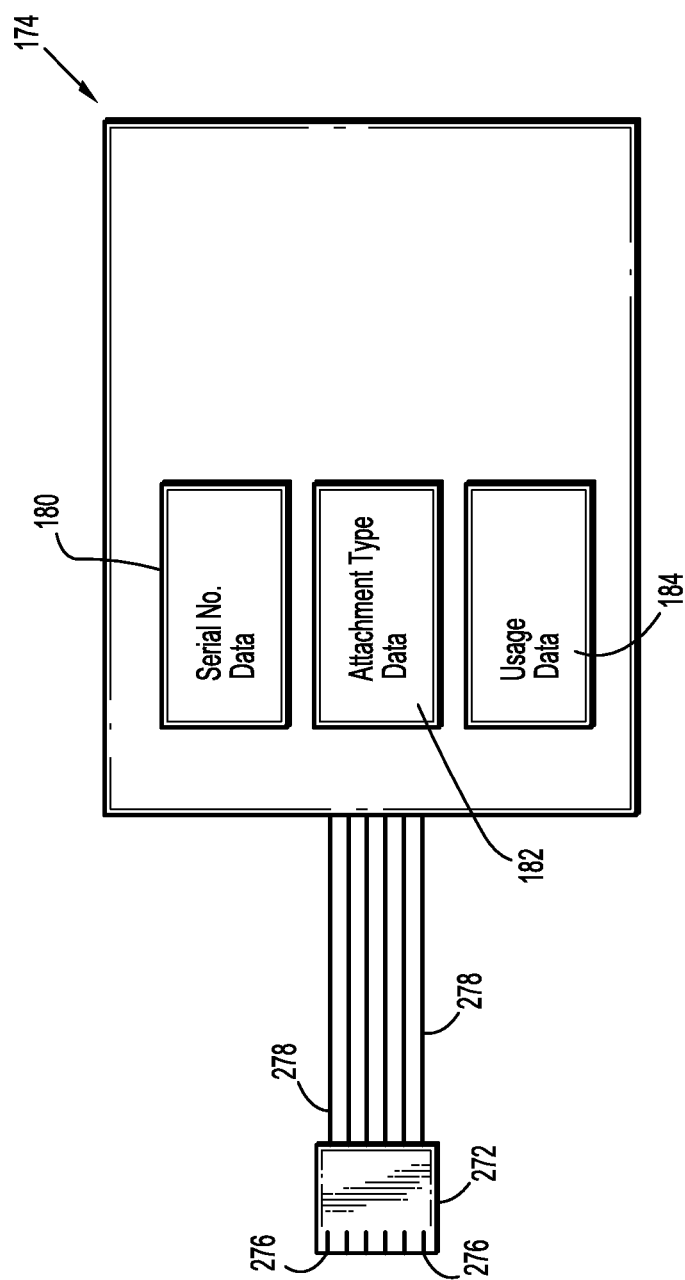
FIG. 10 is a schematic view of a memory device of the first example embodiment of a circular surgical stapler attachment illustrated in FIG. 9b.

FIG. 10 schematically illustrates the memory unit 174. As seen in FIG. 10, data connector 272 includes contacts 276, each electrically and logically connected to memory unit 174 via a respective line 278. Memory unit 174 is configured to store, for example, a serial number data 180, an attachment type identifier (ID) data 182 and a usage data 184. Memory unit 174 may additionally store other data. Both the serial number data 180 and the ID data 182 may be configured as read-only data. In the example embodiment, serial number data 180 is data uniquely identifying the particular surgical instrument or attachment, whereas the ID data 182 is data identifying the type of the attachment, such as, for example, a circular surgical stapler attachment, a linear surgical stapler attachment, etc. The usage data 184 represents usage of the particular attachment, such as, for example, the number of times the anvil 256 of the circular surgical stapler attachment 250 has been advanced or the number of times that the staple driver/cutter 264 of the circular surgical stapler attachment 250 has been advanced or fired.

It should be appreciated that each type of surgical instrument or attachment attachable to the distal end 24 of the flexible shaft 20 may be designed and configured to be used a single time or multiple times. The surgical instrument or attachment may also be designed and configured to be used a predetermined number of times. Accordingly, the usage data 184 may be used to determine whether the surgical instrument or attachment has been used and whether the number of uses has exceeded the maximum number of permitted uses. As more fully described below, an attempt to use a surgical instrument or attachment after the maximum number of permitted uses has been reached will generate an ERROR condition.

It should be appreciated that the circular surgical stapler attachment 250 illustrated in FIG. 9a is intended to be merely an example of a surgical attachment used in conjunction with the electro-mechanical surgical device 10. It should be further appreciated that any other type of surgical instrument or attachment, such as those enumerated hereinabove, may be used in conjunction with the electromechanical surgical device 10. Regardless of the particular type of surgical instrument or attachment, in the example embodiment of the present invention, the surgical instrument or attachment includes the coupling elements 268, 270, 272, as necessary for proper operation of the surgical instrument or attachment, as well as the memory unit 174. Although the drive shafts and motors are described herein as effecting particular functions of the circular surgical stapler attachment 250, it should be appreciated that the drive shafts and motors may effect the same or other functions of other types of surgical instruments or attachments.

Referring again to FIG. 7, in accordance with the example embodiment of the present invention, the controller 122 is configured to read the ID data 182 from the memory unit 174 of the surgical instrument or attachment when the surgical instrument or attachment is initially connected to the flexible shaft 20, and the controller 122 is configured to read the ID data 880 from the memory unit 850 of the PCB 635 of the second coupling 26. The memory units 174, 850 may be electrically and logically connected in parallel to the controller 122 via line 120 of data transfer cable 38 or, alternatively, may be connected to the controller 122 via respective dedicated lines.

Based on the read usage data 870 of the flexible shaft 20, the controller 122 may prevent the surgical device 10 from driving the flexible shaft 20. As described above, a particular flexible shaft 20 may be designed and configured to be used a single time, multiple times, or a predetermined number of times. Accordingly, the usage data 870 may be read by the controller 122 to determine whether the flexible shaft 20 has been used and whether the number of uses has exceeded a maximum number of permitted uses. If the maximum number of uses has been exceeded, the controller 122 may prevent subsequent attempts to use the flexible shaft 20.

Additionally, the controller 122 may write the usage data 870 to the memory unit 850 of the flexible shaft 20. The written usage data 870 may include information relating to, for example, a number of revolutions of one or both rotatable drive shafts 30, 32, a number of uses of one or both rotatable drive shafts 30, 32, a number of firings of one or both rotatable drive shafts 30, 32, and/or the number of times the flexible shaft 20 has been used, etc. It should be appreciated that the written usage data 870 may include information in any form suitable to indicate a change in any condition of the flexible shaft 20 that may relate, for example, to usage.

Based on the read ID data 182, the controller 122 is configured to read or select from the memory unit 130, an operating program or algorithm corresponding to the type of surgical instrument or attachment connected to the flexible shaft 20. The memory unit 130 is configured to store the operating programs or algorithms for each available type of surgical instrument or attachment, the controller 122 selecting and/or reading the operating program or algorithm from the memory unit 130 in accordance with the ID data 182 read from the memory unit 174 of an attached surgical instrument or attachment. As indicated above, the memory unit 130 may include a removable ROM component 132 and/or RAM component 134. Thus, the operating programs or algorithms stored in the memory unit 130 may be updated, added, deleted, improved or otherwise revised as necessary. The operating programs or algorithms stored in the memory unit 130 may be customizable based on, for example, specialized needs of the user. A data entry device, such as, for example, a keyboard, a mouse, a pointing device, a touch screen, etc., may be connected to the memory unit 130 via, for example, a data connector port, to facilitate the customization of the operating programs or algorithms. Alternatively or additionally, the operating programs or algorithms may be customized and preprogrammed into the memory unit 130 remotely from the electro-mechanical surgical device 10. It should be appreciated that the serial number data 180 and/or usage data 184 may also be used to determine which of a plurality of operating programs or algorithms is read or selected from the memory unit 130. It should be appreciated that the operating program or algorithm may alternatively be stored in the memory unit 174 of the surgical instrument or attachment and transferred to the controller 122 via the data transfer cable 38. Once the appropriate operating program or algorithm is read or selected by, or transmitted to, the controller 122, the controller 122 causes the operating program or algorithm to be executed in accordance with operations performed by the user via the wired RCU 150 and/or the wireless RCU 148. As indicated hereinabove, the controller 122 is electrically and logically connected with the first, second, third, fourth and fifth motors 76, 80, 84, 90, 96 via respective lines 116, 118, 124, 126, 128 and controls such motors 76, 80, 84, 90, 96 in accordance with the read, selected or transmitted operating program or algorithm via the respective lines 116, 118, 124, 126, 128.

Figure 11:
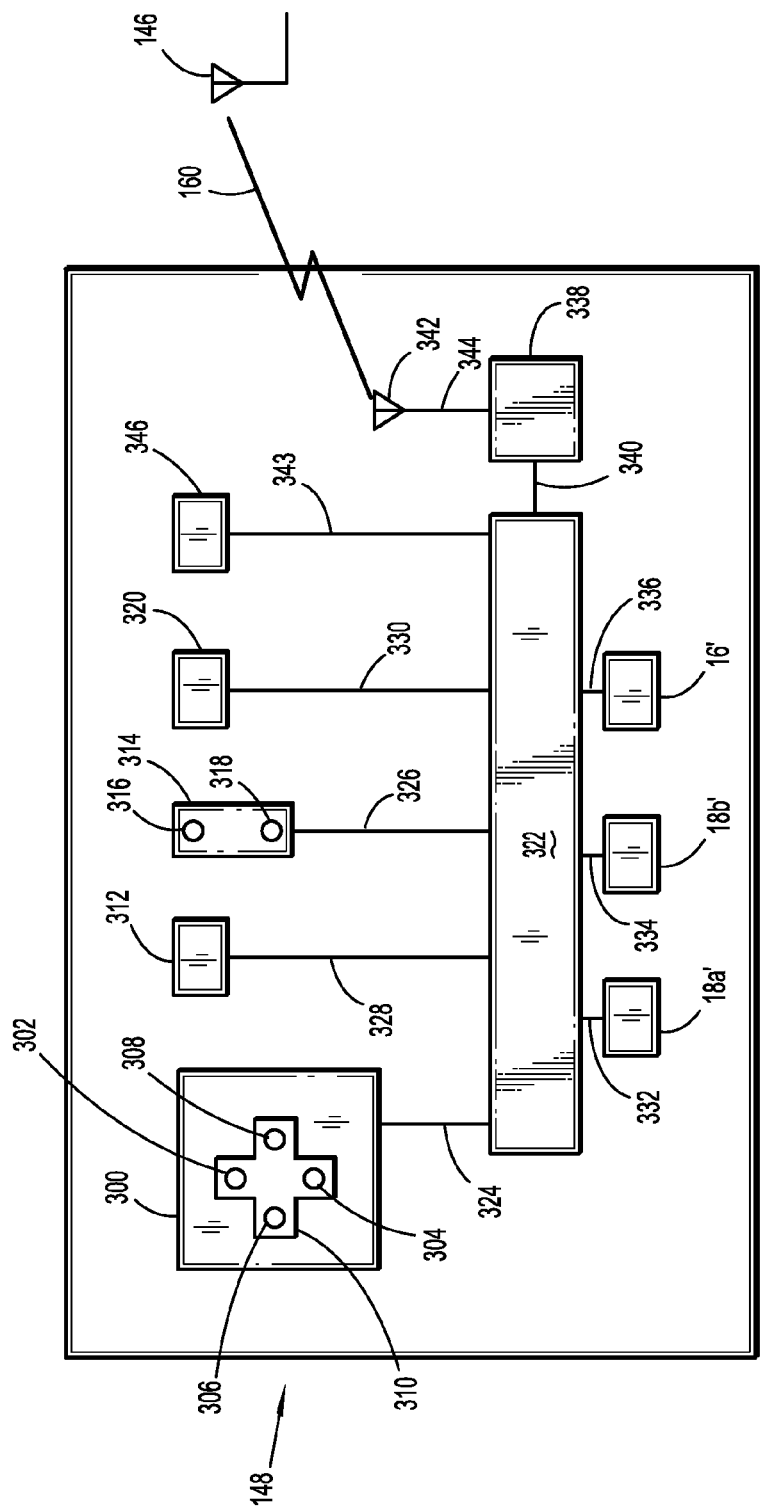
FIG. 11 is a schematic view of a wireless remote control unit of the electromechanical surgical device illustrated in FIG. 1.

Referring now to FIG. 11, there is seen a schematic view of wireless RCU 148. Wireless 148 includes a steering controller 300 having a plurality of switches 302, 304, 306, 308 arranged under a four-way rocker 310. The operation of switches 302, 304, via rocker 310, controls the operation of first and second steering cables 34, 35 via third motor 84. Similarly, the operation of switches 306, 308, via rocker 310, controls the operation of third and fourth steering cables 36, 37 via fourth motor 92. It should be appreciated that rocker 310 and switches 302, 304, 306, 308 are arranged so that the operation of switches 302, 304 steers the flexible shaft 20 in the north-south direction and that the operation of switches 306, 308 steers the flexible shaft 20 in the east-west direction. Reference herein to north, south, east and west is made to a relative coordinate system. Alternatively, a digital joystick, analog joystick, etc. may be provided in place of rocker 310 and switches 302, 304, 306, 308. Potentiometers or any other type of actuator may also be used in place of switches 302, 304, 306, 308.

Wireless RCU 148 further includes a steering engage/disengage switch 312, the operation of which controls the operation of fifth motor 96 to selectively engage and disengage the steering mechanism. Wireless RCU 148 also includes a two-way rocker 314 having first and second switches 316, 318 operable thereby. The operation of these switches 316, 318 controls certain functions of the electromechanical surgical device 10 and any surgical instrument or attachment attached to the flexible shaft 20 in accordance with the operating program or algorithm corresponding to the attached surgical instrument or attachment, if any. For example, where the surgical instrument is a circular surgical stapler attachment 250, such as that shown in FIG. 9a and described hereinabove, operation of the two-way rocker 314 may control the advancement and retraction of the anvil 256. Wireless RCU 148 is provided with yet another switch 320, the operation of which may further control the operation of the electro-mechanical surgical device 10 and any surgical instrument or attachment attached to the flexible shaft 20 in accordance with the operating program or algorithm corresponding to the attached surgical instrument or attachment, if any. For example, when the circular surgical stapler attachment 250 is attached to the flexible shaft 20, operation of the switch 320 initiates the advancement, or firing sequence, of the staple driver/cutter 264.

Wireless RCU 148 includes a controller 322, which is electrically and logically connected with the switches 302, 304, 306, 308 via line 324, with the switches 316, 318 via line 326, with switch 312 via line 328 and with switch 320 via line 330. Wireless RCU 148 may include indicators 18a', 18b', corresponding to the indicators 18a, 18b of front panel 15, and a display device 16', corresponding to the display device 16 of the front panel 15. If provided, the indicators 18a', 18b' are electrically and logically connected to controller 322 via respective lines 332, 334, and the display device 16' is electrically and logically connected to controller 322 via line 336. Controller 322 is electrically and logically connected to a transceiver 338 via line 340, and transceiver 338 is electrically and logically connected to a receiver/transmitter 342 via line 344. A power supply, not shown, for example, a battery, may be provided in wireless RCU 148 to power the same. Thus, the wireless RCU 148 may be used to control the operation of the electro-mechanical surgical device 10 and any surgical instrument or attachment attached to the flexible shaft 20 via wireless link 160.

Wireless RCU 148 may include a switch 346 connected to controller 322 via line 348. Operation of switch 346 transmits a data signal to the transmitter/receiver 146 via wireless link 160. The data signal includes identification data uniquely identifying the wireless RCU 148. This identification data is used by the controller 122 to prevent unauthorized operation of the electro-mechanical surgical device 10 and to prevent interference with the operation of the electro-mechanical surgical device 10 by another wireless RCU. Each subsequent communication between the wireless RCU 148 and the electro-mechanical device surgical 10 may include the identification data. Thus, the controller 122 can discriminate between wireless RCUs and thereby allow only a single, identifiable wireless RCU 148 to control the operation of the electro-mechanical surgical device 10 and any surgical instrument or attachment attached to the flexible shaft 20.

Based on the positions of the components of the surgical instrument or attachment attached to the flexible shaft 20, as determined in accordance with the output signals from the encoders 106, 108, the controller 122 may selectively enable or disable the functions of the electro-mechanical surgical device 10 as defined by the operating program or algorithm corresponding to the attached surgical instrument or attachment. For example, where the surgical instrument or attachment is the circular surgical stapler attachment 250 illustrated in FIG. 9a, the firing function controlled by the operation of the switch 320 is disabled unless the space or gap between the anvil 256 and the body portion 252 is determined to be within an acceptable range. The space or gap between the anvil 256 and the body portion 252 is determined based on the output signal from the encoders 106, 108, as more fully described hereinabove. It should be appreciated that the switch 320 itself remains operable but that the controller 122 does not effect the corresponding function unless the space or gap is determined to be within the acceptable range.

Figure 12:
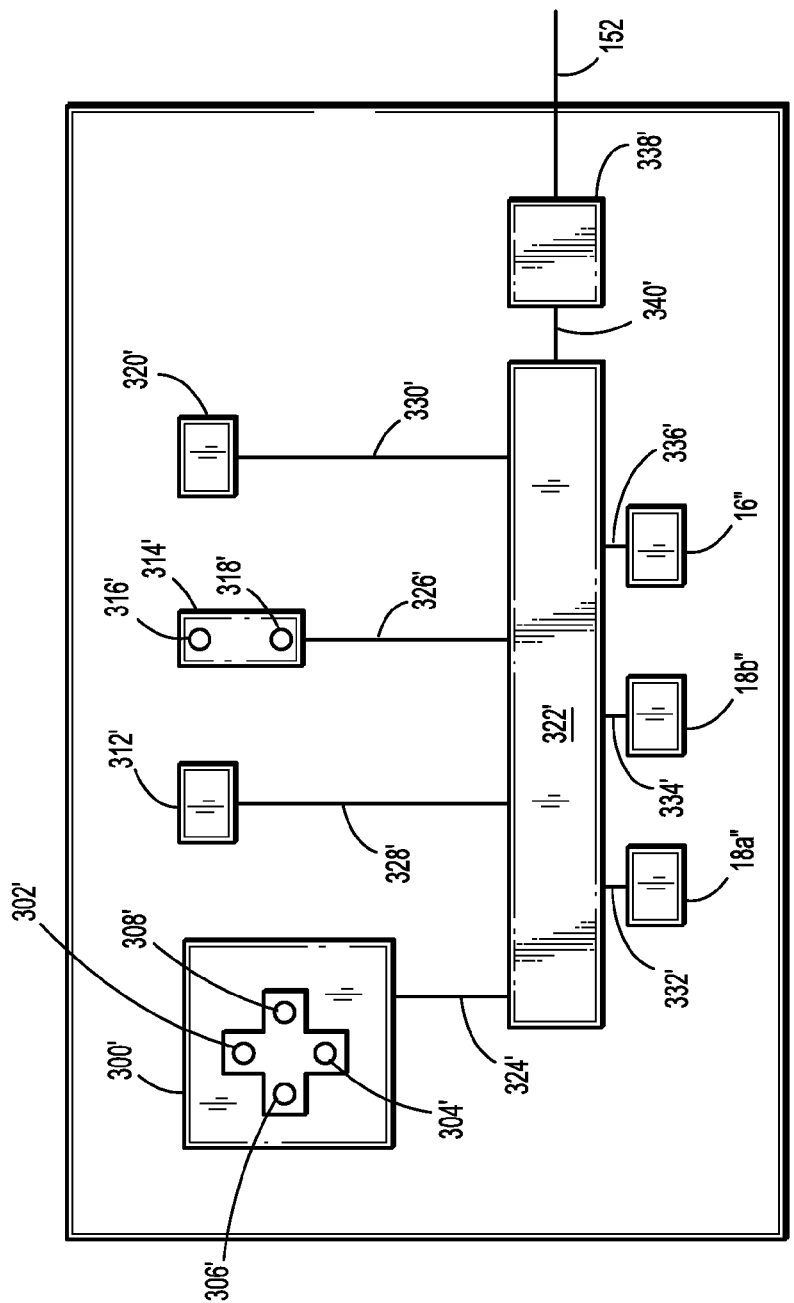
FIG. 12 is a schematic view of a wired remote control unit of the electromechanical surgical device illustrated in FIG. 1.

Referring now to FIG. 12, there is seen a schematic view of a wired RCU 150. In the example embodiment, wired RCU 150 includes substantially the same control elements as the wireless RCU 148 and further description of such elements is omitted. Like elements are noted in FIG. 12 with an accompanying prime. It should be appreciated that the functions of the electro-mechanical surgical device 10 and any surgical instrument or attachment attached to the flexible shaft 20 may be controlled by the wired RCU 150 and/or by the wireless RCU 148. In the event of a battery failure, for example, in the wireless RCU 148, the wired RCU 150 may be used to control the functions of the electro-mechanical surgical device 10 and any surgical instrument or attachment attached to the flexible shaft 20.

As described hereinabove, the front panel 15 of housing 14 includes display device 16 and indicators 18a, 18b. The display device 16 may include an alpha-numeric display device, such as an LCD display device. Display device 16 may also include an audio output device, such as a speaker, a buzzer, etc. The display device 16 is operated and controlled by controller 122 in accordance with the operating program or algorithm corresponding to a surgical instrument or attachment, if any, attached to the flexible shaft 20. If no surgical instrument or attachment is so attached, a default operating program or algorithm may be read or selected by, or transmitted to, controller 122 to thereby control the operation of the display device 16 as well as the other aspects and functions of the electromechanical surgical device 10. If the circular surgical stapler attachment 250 illustrated in FIG. 9a is attached to flexible shaft 20, display device 16 may display, for example, data indicative of the gap between the anvil 256 and the body portion 252 as determined in accordance with the output signal of encoders 106, 108, as more fully described hereinabove.

Similarly, the indicators 18a, 18b are operated and controlled by controller 122 in accordance with the operating program or algorithm corresponding to the surgical instrument or attachment, if any, attached to the flexible shaft 20. Indicator 18a and/or indicator 18b may include an audio output device, such as a speaker, a buzzer, etc., and/or a visual indicator device, such as an LED, a lamp, a light, etc. If the circular surgical stapler attachment 250 illustrated in FIG. 9a is attached to the flexible shaft 20, indicator 18a may indicate, for example, that the electromechanical surgical device 10 is in a power ON state, and indicator 18b may, for example, indicate whether the gap between the anvil 256 and the body portion 252 is determined to be within the acceptable range as more fully described hereinabove. It should be appreciated that although only two indicators 18a, 18b are described, any number of additional indicators may be provided as necessary. Additionally, it should be appreciated that although a single display device 16 is described, any number of additional display devices may be provided as necessary. The display device 16' and indicators 18a', 18b' of wireless RCU 150 and the display device 16" and indicators 18a", 18b" of wired RCU 148 are similarly operated and controlled by respective controller 322, 322' in accordance with the operating program or algorithm corresponding to the surgical instrument or attachment, if any, attached to the flexible shaft 20.

Figure 13:
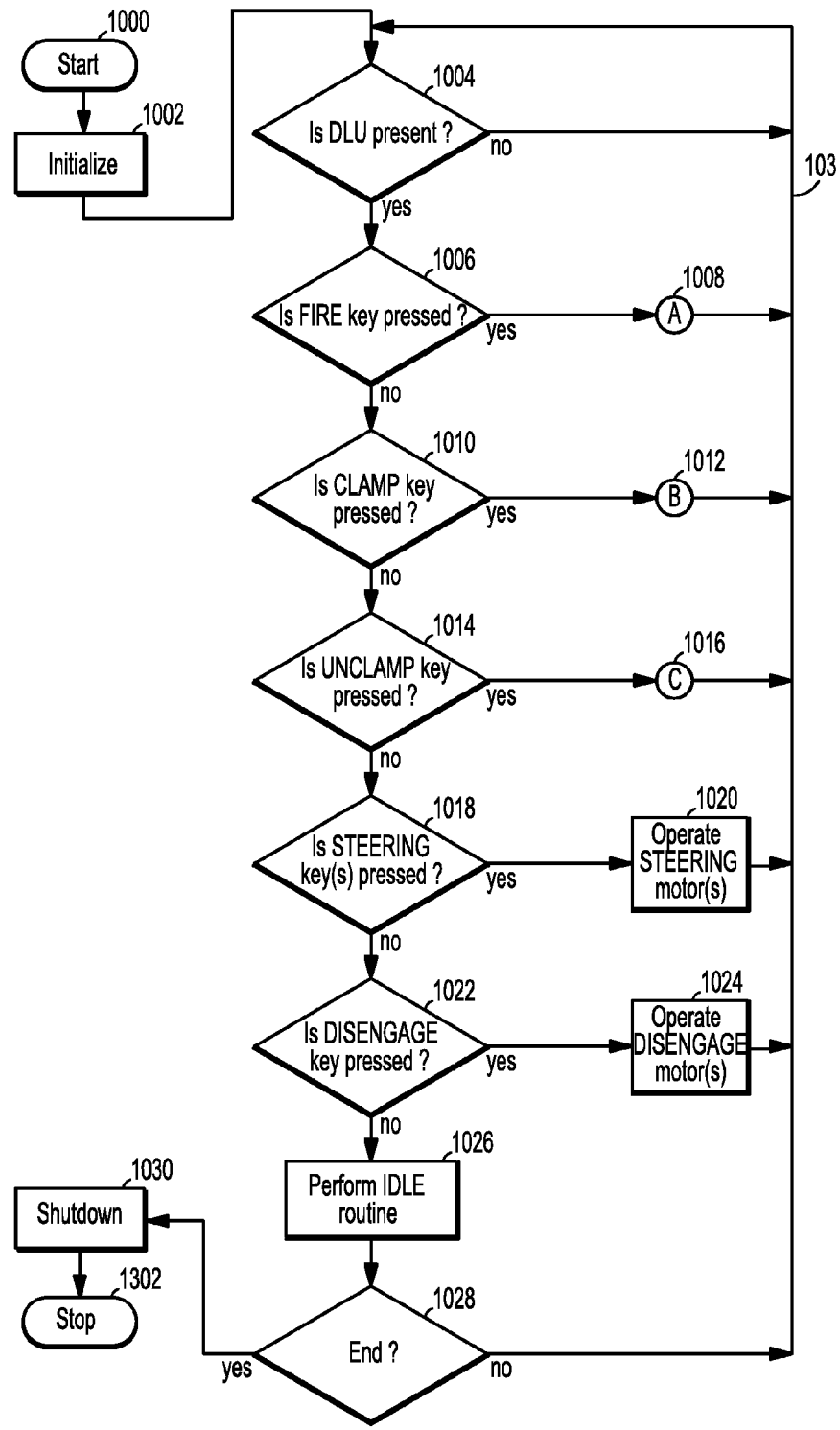
FIG. 13 illustrates a flowchart of a first example embodiment of a main operating program for operating the electro-mechanical surgical device illustrated in FIG. 1.

Referring now to FIG. 13, there is seen a flowchart of a first example embodiment of a main operating program according to the present invention. The main operating program begins at step 1000 and proceeds to step 1002, during which the electro-mechanical surgical device 10 is initialized. Step 1002 may include initialization steps, such as memory population and initialization, diagnostic self-testing, etc. After initialization step 1002, it is determined in step 1004 whether a surgical instrument or attachment ("DLU") is present—that is, installed on the distal end 24 of flexible shaft 20. If it is determined in step 1004 that no DLU is present, control is transferred to loop 1034. If it is determined that a DLU is present, the operating program proceeds to step 1006, in which it is determined whether the FIRE key is pressed. FIRE key, in this context, refers to one of the switches of the wireless RCU 148 and/or wired RCU 150. More particularly, the FIRE key may correspond to switch 320 of wireless RCU 148 and/or switch 320' of wired RCU 150. If it is determined in step 1006 that FIRE key is pressed, control is transferred to routine A in step 1008. Routine A is specific to the DLU, if any, attached to the flexible shaft 20. Routine A is more fully described hereinbelow and in FIGS. 14a to 14d. After the execution of routine A in step 1008, control is transferred to loop 1034.

If it is determined in step 1006 that the FIRE key is not pressed, it is determined in step 1010 whether the CLAMP key is pressed. In this context, the CLAMP key refers to one of the switches of the wireless RCU 148 and/or wired RCU 150. More particularly, CLAMP switch may correspond to, for example, switch 316 of wireless RCU 148 and/or to switch 316' of wired RCU 150. If it is determined in step 1010 that CLAMP key is pressed, control is transferred to routine B in step 1012. Routine B is specific to the DLU, if any, attached to the flexible shaft 20. Routine B is more fully described hereinbelow and in FIGS. 15a and 15b. After the execution of routine B in step 1012, control is transferred to loop 1034.

If it is determined in step 1010 that the CLAMP key is not pressed, it is determined in step 1014 whether the UNCLAMP key is pressed. In this context, the UNCLAMP key refers to one of the switches of the wireless RCU 148 and/or wired RCU 150. More particularly, the UNCLAMP switch may correspond to, for example, switch 318 of wireless RCU 148 and/or to switch 318' of wired RCU 150. If it is determined in step 1014 that UNCLAMP key is pressed, control is transferred to routine C in step 1016. Routine C is specific to the DLU, if any, attached to the flexible shaft 20. Routine C is more fully described hereinbelow and in FIG. 16. After the execution of routine C in step 1016, control is transferred to loop 1034.

If it is determined in step 1014 that the UNCLAMP key is not pressed, it is determined in step 1018 whether one or more of STEERING keys are pressed. In this context, the STEERING keys refer to respective switches of the wireless RCU 148 and/or wired RCU 150. More particularly, the STEERING keys may correspond to switches 302, 304, 306, 308 of wireless RCU 148 and/or switches 302', 304', 306', 308' of wired RCU 150. If it is determined in step 1018 that one or more STEERING keys are pressed, operation of respective steering motor(s) is performed in step 1020. The steering motors may correspond to third motor 84 and fourth motor 92 as more fully set forth above. After the execution of step 1020, control is transferred to loop 1034.

If it is determined in step 1018 that none of the STEERING keys is pressed, it is determined in step 1022 whether the DISENGAGE key is pressed. In this context, the DISENGAGE key refers to one of the switches of wireless RCU 148 and/or wired RCU 150. More particularly, DISENGAGE key may correspond to switch 312 of wireless RCU 148 and/or switch 312' of wired RCU 150. If it is determined in step 1022 that the DISENGAGE key is pressed, a disengage operation is performed in step 1024. After the execution of step 1024, control is transferred to loop 1034.

If it is determined in step 1022 that DISENGAGE key is not pressed, an IDLE routine is performed in step 1026.

In step 1028, it is determined whether to end the operation of the main operating program. If it is determined in step 1028 to not end the operation of the main operating program, control is transferred to loop 1034. If, however, it is determined in step 1028 to end or terminate the operation of the main operating program, a shutdown routine is executed in step 1030, and the main operating program is thereafter terminated in step 1032.

It should be appreciated that the main operating program may determine which, if any, key is pressed in the order illustrated in FIG. 13 or in any other appropriate order. It should also be appreciated that the main operating program illustrated in FIG. 13, as well as the routines illustrated in FIGS. 14*a* to 14*d*, 15*a*, 15*b* and 16, may be embodied, for example, in a messaging-based, event-driven and/or polling-type software application.

Referring now to FIGS. 14*a* to 14*d*, there is seen a flowchart of a first example embodiment of a fire routine specific to a circular surgical stapler attachment 250, such as that illustrated in FIG. 9*a*, or 2250, such as that illustrated in FIGS. 9*b* and 9*c*. It should be appreciated that the fire routine illustrated in FIGS. 14*a* to 14*d* represents the routine A of step 1008 of the main operating program illustrated in FIG. 13 and that the firing routine illustrated in FIGS. 14*a* to 14*d* is specific to a circular surgical stapler attachment 250, such as that illustrated in FIG. 9*a*, or 2250, such as that illustrated in FIGS. 9*b* and 9*c*. It should be further appreciated that other surgical instruments or attachments, such as those enumerated above, may have other firing routines associated therewith.

Proceeding from step 1008, it is determined in step 1100 whether the DLU—the circular surgical stapler attachment 250—has been fully opened. This determination may be made based on the signals generated by the encoders 106, 108, as more fully described above. If it is determined in step 1100 that the DLU has not been fully opened, an ERROR condition is determined in step 1102 in that the DLU is not ready for firing. Control is then transferred to step 1120, wherein control returns to the main operating program illustrated in FIG. 13.

If it is determined in step 1100 that the DLU has been fully opened, it is determined in step 1104 whether the DLU has been fully clamped. This determination may be made based on the signals generated by the encoders 106, 108, as more fully described above. If it is determined in step 1104 that the DLU has not been fully clamped, an ERROR condition is determined in step 1106 in that the DLU is not within an acceptable range for firing. Control is then transferred to step 1120, wherein control returns to the main operating program illustrated in FIG. 13.

If it is determined in step 1104 that the DLU has been fully clamped, it is determined in step 1108 whether the DLU has been previously fired. This determination may be made based on the signals generated by the encoders 106, 108 and/or in accordance with usage data 184. If it is determined in step 1108 that the DLU has been previously fired, an ERROR condition is determined in step 1110 in that the DLU has been used. Control is then transferred to step 1120, wherein control returns to the main operating program illustrated in FIG. 13. It should be appreciated that a similar usage determination may be made in the main operating program illustrated in FIG. 13, for example, in the initialization step 1002 or in the DLU presence determining step 1004, as an alternative or in addition to the determining step 1108.

If it is determined in step 1108 that the DLU has not been previously fired, a usage count is decremented in step 1112. The usage count may be stored in usage data 184 as more fully described hereinabove. Several attempts at decrementing the usage count may be made in step 1112. However, a failure to decrement the usage count may nevertheless occur. In step 1114, it is determined whether the usage count decrementing step 1112 has failed. If it is determined in step 1114 that the decrementing of usage count failed, a ERROR condition is determined in step 1116. Thereafter, in step 1118, a wait loop is executed until all keys of the wireless RCU 148 and/or wired RCU 150 have been released. After it is determined in step 1118 that all keys have been released, control is transferred to step 1120. Thereafter, control returns to the main operating program illustrated in FIG. 13.

If it is determined in step 1114 that the usage count decrementing did not fail, the firing motor current limit is set in step 1122. In this context, the firing motor may correspond to the second motor 80 as more fully described hereinabove. The firing motor is then started in step 1124 to begin the advancement of the staple driver/cutter 264.

Figure 14A:
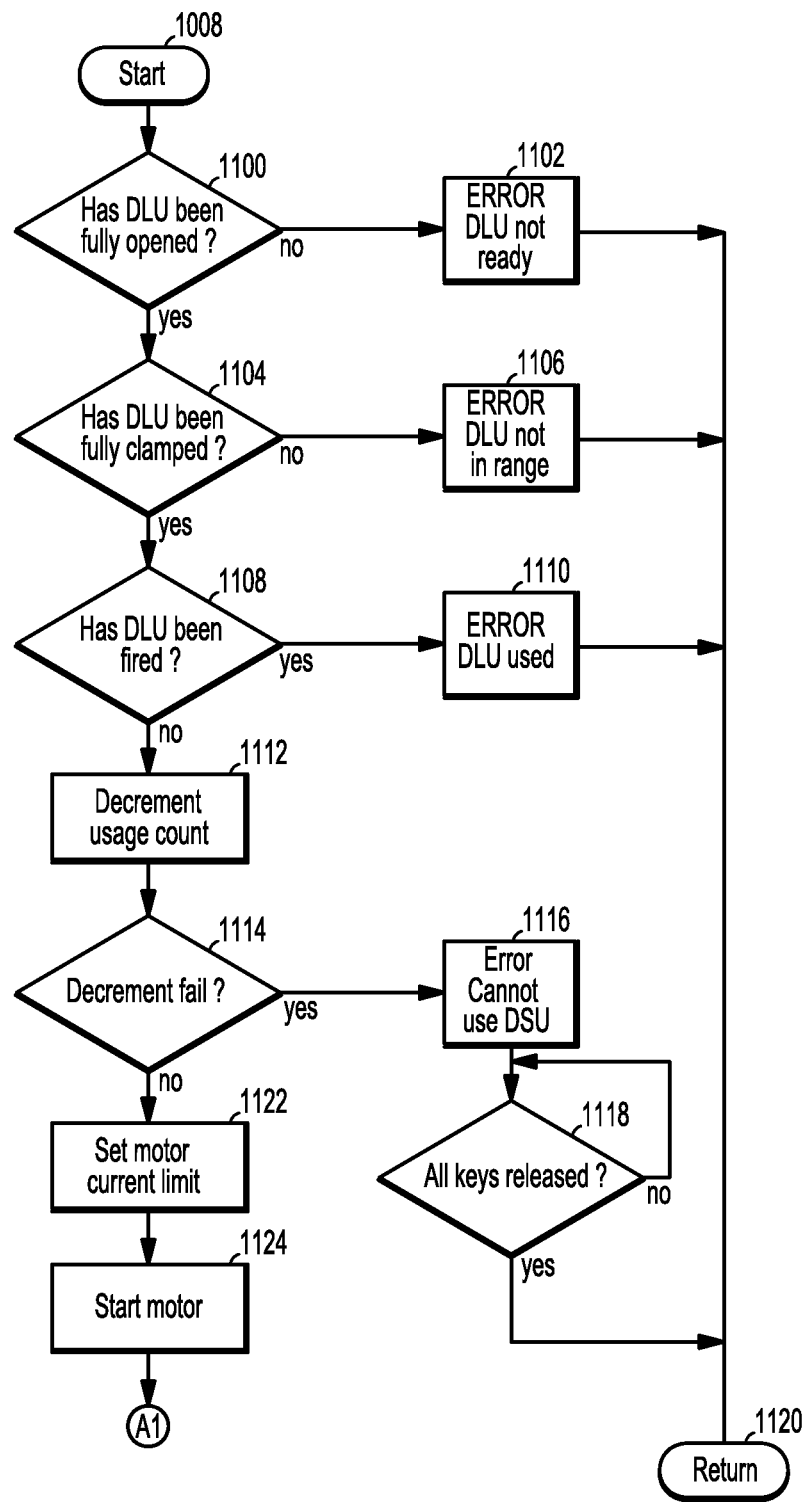
FIGS. 14a to 14d illustrate a flowchart of a first example embodiment of a fire routine for a circular surgical stapler attachment, such as that illustrated in FIGS. 9a to 9c.
Figure 14B:
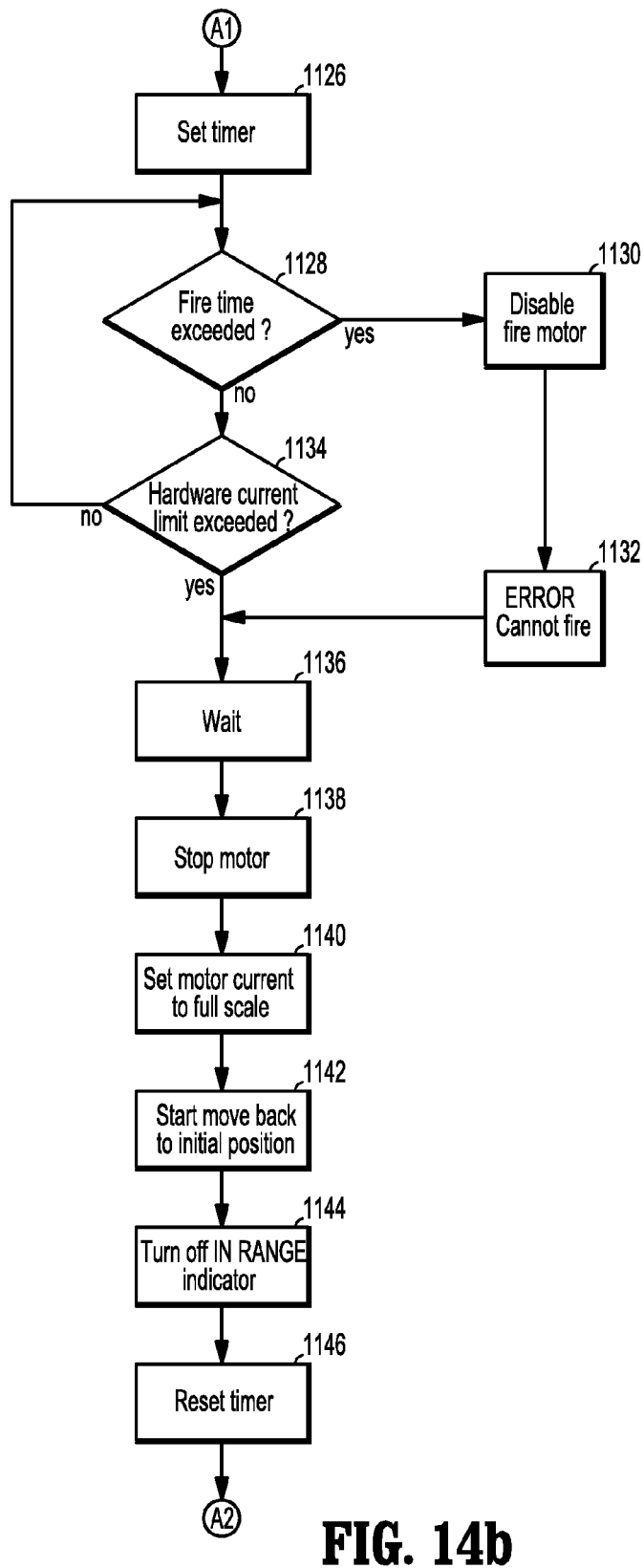

Referring now to FIG. 14*b*, a timer is set in step 1126. It is thereafter determined in step 1128 whether the time elapsed for the firing operation has exceeded a predetermined threshold. If it is determined in step 1128 that the firing time limit has been exceeded, the firing motor is disabled in step 1130, and an ERROR condition is determined in step 1132. Control then proceeds to step 1136. If, however, it is determined in step 1128 that the firing time has not exceeded the predetermined firing time limit, it is determined in step 1134 whether a hardware current limit has been exceeded. The hardware current limit relates to the resistance of the firing motor to continued operation. A condition that the hardware current limit has been exceeded is indicative that the stapling operation has been successfully completed. If it is determined in step 1134 that the hardware current limit has not been exceeded, the operation of firing motor is continued until either the predetermined firing time limit has been exceeded or the hardware current limit has been exceeded. In either instance control proceeds thereafter to step 1136.

Step 1136 represents a waiting step, during which a predetermined wait time is permitted to elapse. This wait time permits the driving and driven elements of electro-mechanical surgical device 10 and circular surgical stapler attachment 250 to come to rest before proceeding to step 1138, in which step the firing motor is stopped.

After the firing motor is stopped in step 1138, the motor current limit is set to full scale in step 1140, and then the firing motor is started in step 1142 in a reverse direction to retract the staple driver/cutter 264 and return the same to its initial position. Then, once the gap between the anvil 256 and the body portion 252 has exceeded the acceptable range, the indicator 18*a*, 18*b* corresponding to an IN-RANGE indicator is turned off in step 1144. Alternatively, the IN-RANGE indicator may be turned off in step 1144 upon the start of the reversal of the motor in step 1142. After the IN-RANGE indicator is turned off in step 1144, the timer is reset in step 1146.

Figure 14C:
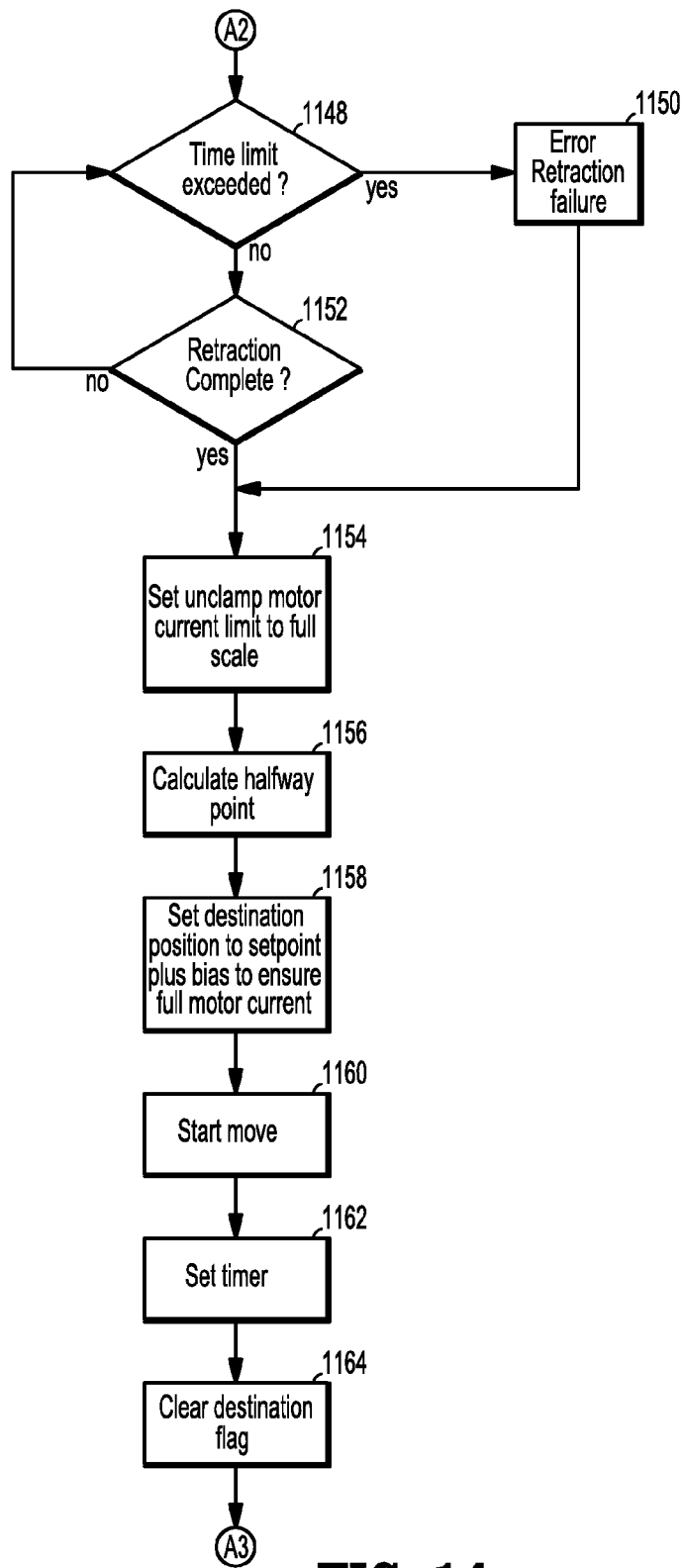

Referring now to FIG. 14*c*, it is determined in step 1148 whether a predetermined time limit for completing the retraction of the staple driver/cutter 264, based on the timer reset in step 1146, has been exceeded. If it is determined in step 1148 that the predetermined time limit has been exceeded, an ERROR condition is determined in step 1150 in that the retraction operation failed to be completed within the permissible predetermined time limit. If, however, it is determined in step 1148 that the predetermined time limit has not been exceeded, it is determined in step 1152 whether retraction of the staple driver/cutter 264 has been completed. If it is determined in step 1152 that the retraction of the staple driver/cutter 264 has not been completed, control returns to step 1148. Retraction of staple driver/cutter 264 continues until either the predetermined time limit has been exceeded as determined in step 1148 or the retraction has been completed as determined in step 1152. It should be appreciated that the determination made in step 1152 may be based on the signals generated by the encoders 106, 108. After it is determined that the retraction of staple driver/cutter 264 has been completed (step 1152) or that the predetermined time limit has been exceeded (step 1148), the unclamp motor current limit is set of full scale in step 1154. In this context, the unclamp motor may correspond to first motor 76 as more fully described hereinabove.

In step 1156, the halfway point between the current position of the anvil 256 and the final, unclamped position of the anvil 256 is calculated. A "phantom" destination position is set in step 1158 to a predetermined setpoint plus a predetermined bias value to ensure that the unclamp motor achieves its maximum, or full, current to thereby ensure the maximum torque output from the unclamp motor. In step 1160, the movement of the unclamp motor is initiated. In step 1162, the timer is set, and in step 1164 a destination flag is cleared.

Figure 14D:
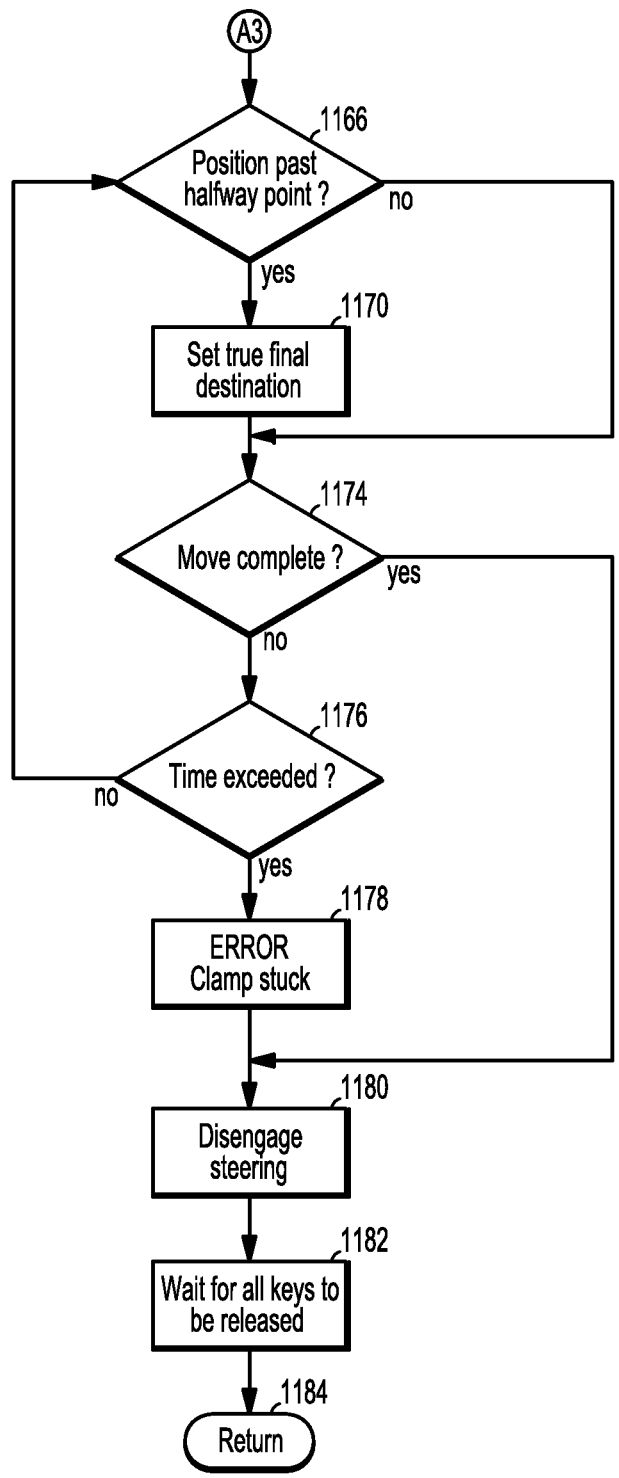

Referring now to FIG. 14*d*, it is determined in step 1166 whether the anvil 256 has passed the halfway point determined in step 1156. If it is determined in step 1166 that the anvil 256 has passed the halfway point determined in step 1156, the "true" final destination position for the anvil 256 is set in step 1170, thereby superceding the "phantom" final destination set in step 1158. Control is then transferred to step 1174. If, however, it is determined in step 1166 that the position of the anvil 256 is not past the halfway point determined in step 1156, control is directly transferred to step 1174, bypassing the destination resetting step 1170.

In step 1174, it is determined whether the anvil 256 has reached the "true" final destination set in step 1170. It should be appreciated that the position of the anvil 256 may be determined in accordance with the signals output by encoders 106, 108 as more fully described hereinabove. If it is determined in step 1174 that anvil 256 has reached its "true" final destination set in step 1170, control is transferred to step 1180, described below. If, however, it is determined in step 1174 that the "true" final destination of the anvil 256 has not been reached, it is determined in step 1176, with reference to the timer reset in step 1162, whether a predetermined time limit has been exceeded. If it is determined in step 1176 that the predetermined time limit has not been exceeded, control is returned to step 1166, and the unclamp motor continues its operation to further unclamp the anvil 256. If, however, it is determined in step 1176 that the predetermined time limit has been exceeded, and ERROR condition is determined in step 1178 in that the anvil 256 could be moved into its "true" final destination within the predetermined time limit. Control is thereafter transferred to step 1180, in which the steering mechanism is disengaged. In the example embodiment of electro-mechanical surgical device 10 described above, the steering mechanism may include the fifth motor 96 and/or carriage 100 as more fully described hereinabove. After the steering mechanism has been disengaged in step 1180, a wait loop is executed in step 1182 until all keys of wireless RCU 148 and/or wired RCU 150 have been released. Once all of the keys have been released, control returns in step 1184 to the main operating program illustrated in FIG. 13.

Figure 15A:
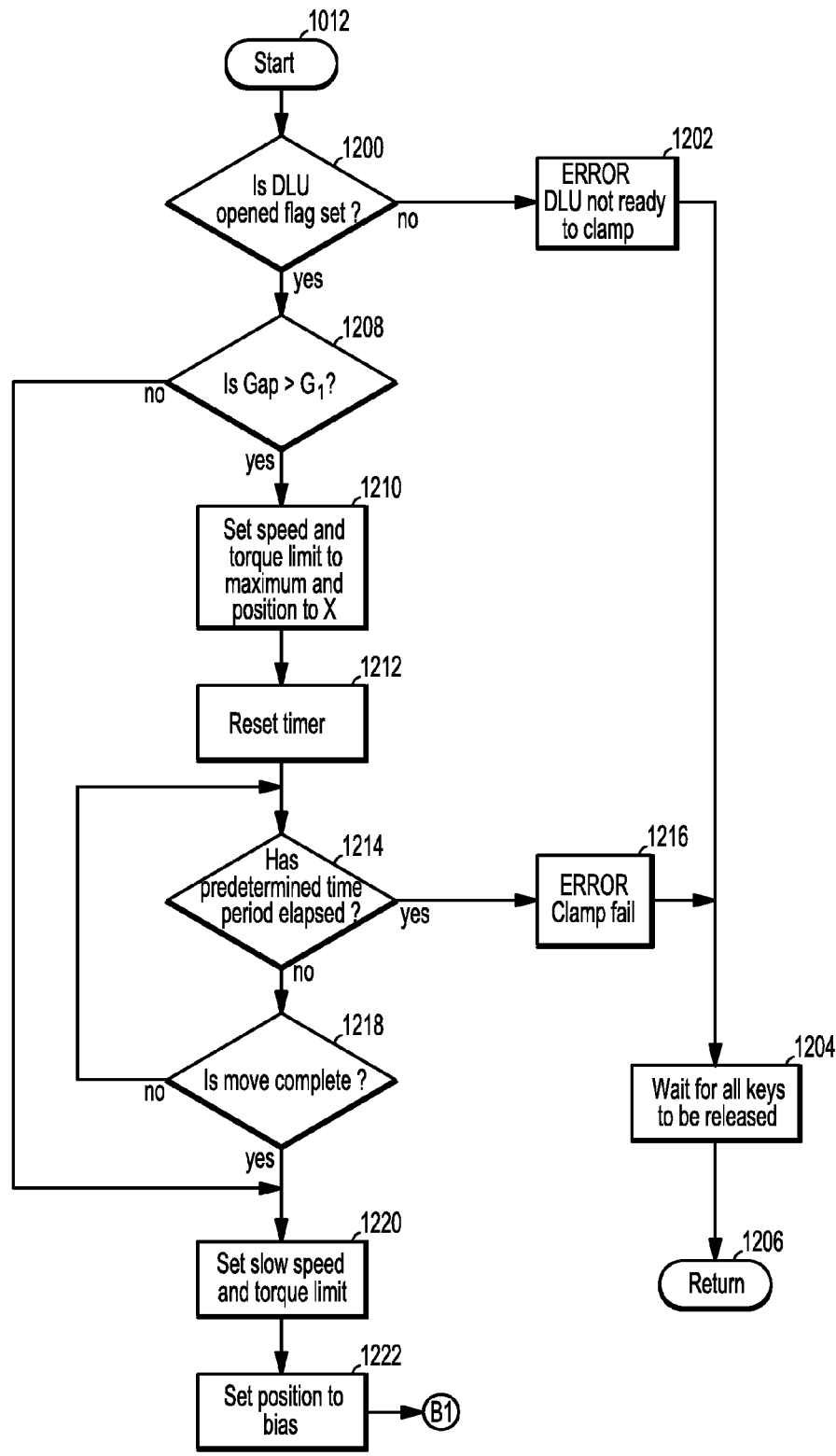
FIGS. 15a and 15b illustrate a flowchart of a clamp routine for a circular surgical stapler attachment, such as that illustrated in FIGS. 9a to 9c.
Figure 15B:
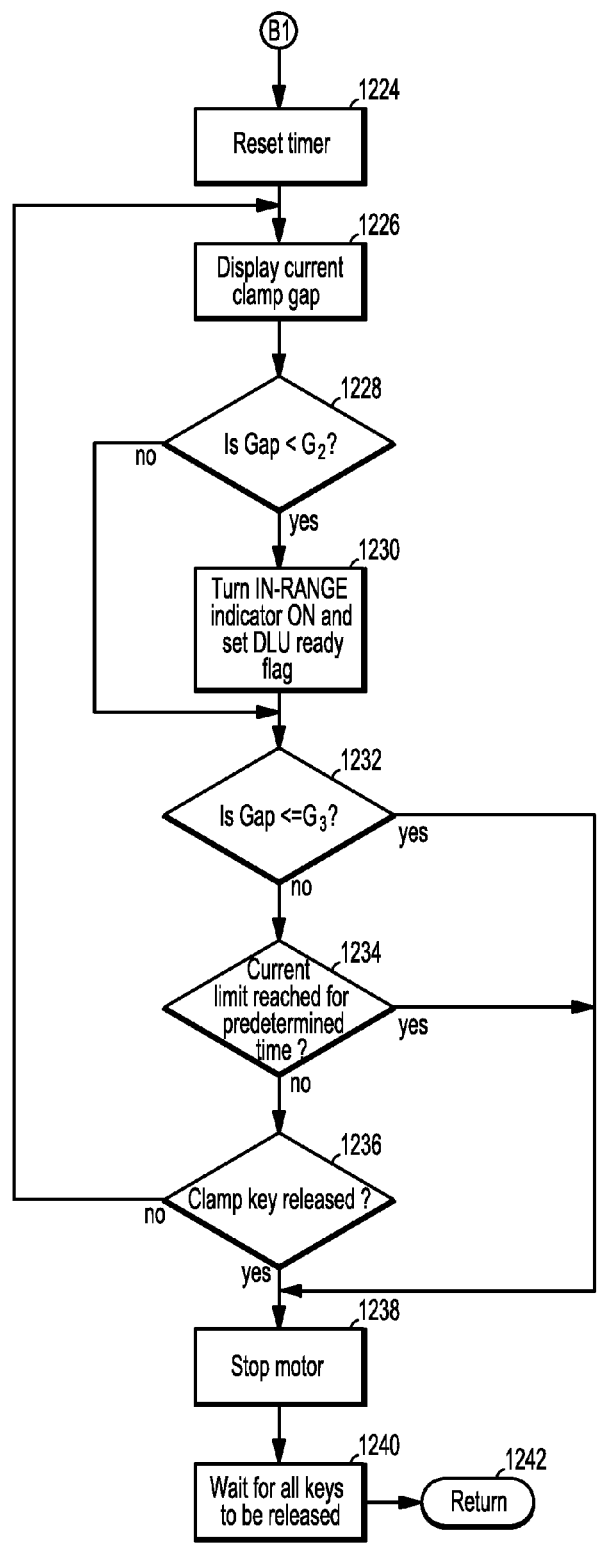

Referring now to FIGS. 15*a* and 15*b*, there is seen a flowchart of a first example embodiment of a clamp routine specific to a circular surgical stapler attachment 250, such as that illustrated in FIG. 9*a*, or 2250, such as that illustrated in FIGS. 9*b* and 9*c*. It should be appreciated that the clamp routine illustrated in FIGS. 15*a* and 15*b* represents the routine B of step 1012 of the main operating program illustrated in FIG. 13 and that the clamp routine illustrated in FIGS. 15*a* and 15*b* is specific to a circular surgical stapler attachment 250, such as that illustrated in FIG. 9*a*, or 2250, such as that illustrated in FIGS. 9*b* and 9*c*. It should be further appreciated that other surgical instruments or attachments, such as those enumerated above, may have other clamping routines associated therewith.

Proceeding from step 1012, it is determined in step 1200 whether a DLU open flag is set. If it is determined in step 1200 that the DLU open flag is not set, an ERROR condition is determined in step 1202 in that the DLU is not ready to clamp. A wait loop is executed thereafter in step 1204, and once all keys of wireless RCU 148 and/or wired RCU 150 have been released, control returns in step 1206 to the main operating program illustrated in FIG. 13.

If, however, it is determined in step 1200 that the DLU open flag is set, it is determined in step 1208 whether the gap between the anvil 256 and the body portion 252 is greater than a predetermined threshold $G_1$, such as, for example, 5.0 mm. This determination may be made based on the signals generated by the encoders 106, 108, as more fully described above. If it determined that the gap between the anvil 256 and the body portion 252 is less than the predetermined threshold $G_1$, control proceeds to step 1220. If, however, it is determined in step 1208 that the gap between the anvil 256 and the body portion 252 is greater than the predetermined threshold $G_1$, control proceeds to step 1210 in which a CLAMP motor speed and torque limit are set to the respective maximum values. In this context, the CLAMP motor may correspond to first motor 76 as more fully described hereinabove. A timer is reset in step 1212, and the control loop of steps 1214 and 1218 is executed until either a predetermined time period for reaching a gap of less than the predetermined threshold $G_1$ is exceeded or the gap is determined to be less than the predetermined threshold $G_1$. If it is determined in step 1214 that the predetermined time period has been exceeded, an ERROR condition is determined in step 1216 in that the clamp operation is considered to have failed. After step 1216 is performed, step 1204 is performed, in which a wait loop is executed until all keys of wireless RCU 148 and/or wired RCU 150 have been released. Thereafter, control returns in step 1206 to the main operating program illustrated in FIG. 13.

If it is determined in step 1214 that the predetermined time period has not been exceeded, it is determined in step 1218 whether the movement of the anvil 256 to a location in which the gap between the anvil 256 and the body portion 252 is less than the predetermined threshold $G_1$ has been completed. If it is determined in step 1218 that this move has not been completed, the operation of CLAMP motor is continued, and control returns to step 1214. If however, it is determined in step 1218 that the move is complete, control proceeds to step 1220.

In step 1220, a speed lower than the maximum speed set in step 1210 is set for the CLAMP motor and a torque limit lower than the torque limit set in step 1210 is set for the CLAMP motor. Thereafter, in step 1222, a position bias is set to ensure that the CLAMP motor outputs full torque when the gap between the anvil 256 and the body portion 252 approaches the bias value. The bias value may be, for example, approximately 1.0 mm to ensure full torque output from the CLAMP motor when the gap is approximately equal to 1.0 mm.

Referring now to FIG. 15*b*, control proceeds to step 1224, in which a timer is reset. In step 1226, the value of the current gap between the anvil 256 and the body portion 252 is displayed on the display device 16. In step 1228, it is determined whether the gap between the anvil 256 and the body portion 252 is less than a predetermined threshold $G_2$. This determination may be made based on the signals generated by the encoders 106, 108, as more fully described above. The predetermined threshold $G_2$ may be, for example, 2.0 mm. If the gap between the anvil 256 and the body portion 252 is determined in step 1228 to be less than the predetermined threshold $G_2$, control proceeds to step 1230, in which an IN-RANGE indicator is activated and a DLU ready flag is set. The IN-RANGE indicator may correspond to one of the indicators 18a, 18b, either one or both of which may be, for example, LED elements or other audio or visual indicators. If it is determined in step 1228 that the gap between the anvil 256 and the body portion 252 is not less than the predetermined threshold $G_2$, control proceeds to step 1232, in which it is determined whether the gap between the anvil 256 and the body portion is less than or equal to another predetermined threshold $G_3$. This determination may be made based on the signals generated by the encoders 106, 108, as more fully described above. The predetermined threshold $G_3$ may be, for example, 1.0 mm. If it is determined in step 1232 that the gap between the anvil 256 and the body portion 252 is less than or equal to the predetermined threshold $G_3$, control proceeds to step 1238, described below. However, if it is determined in step 1232 that the gap between the anvil 256 and the body portion 252 is greater than the predetermined threshold $G_3$, it is determined in step 1234 whether the current limit to the CLAMP motor has been reached for a predetermined time limit. That the current limit to the CLAMP motor has been reached for the predetermined time limit is indicative that tissue is fully clamped between the anvil 256 and the body portion 252. The predetermined time limit may be, for example, 1.0 second. If it is determined in step 1234 that the current limit to the CLAMP motor has been reached for the predetermined time limit, control proceeds to step 1238. If, however, it is determined in step 1234 that the current limit to the CLAMP motor has not been exceeded for the predetermined time limit, it is determined in step 1236 whether the CLAMP key has been released. If it is determined in step 1236 that the CLAMP key has not been released, control returns to step 1226. If it is determined in step 1236 that the CLAMP key has been released, control proceeds to step 1238.

In step 1238, the operation of the CLAMP motor is stopped. Thereafter, in step 1240, a wait loop is executed until all keys of wireless RCU 148 and/or wired RCU 150 have been released. After all keys have been released, control returns in step 1242 to the main operating program illustrated in FIG. 13.

Figure 16:
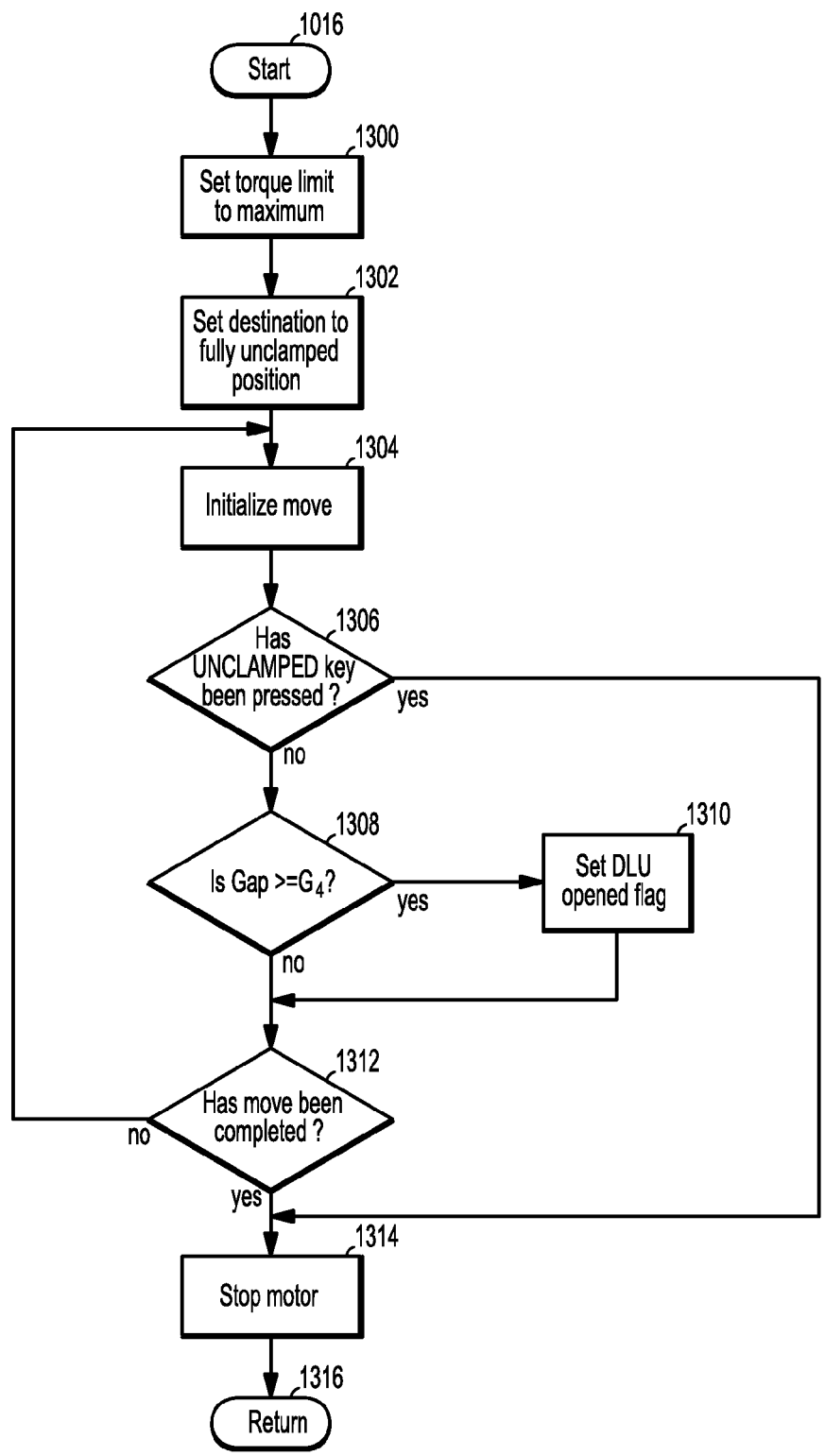
FIG. 16 illustrates a flowchart of an unclamp routine for a circular surgical stapler attachment, such as that illustrated in FIGS. 9a to 9c.
Figure 17A:
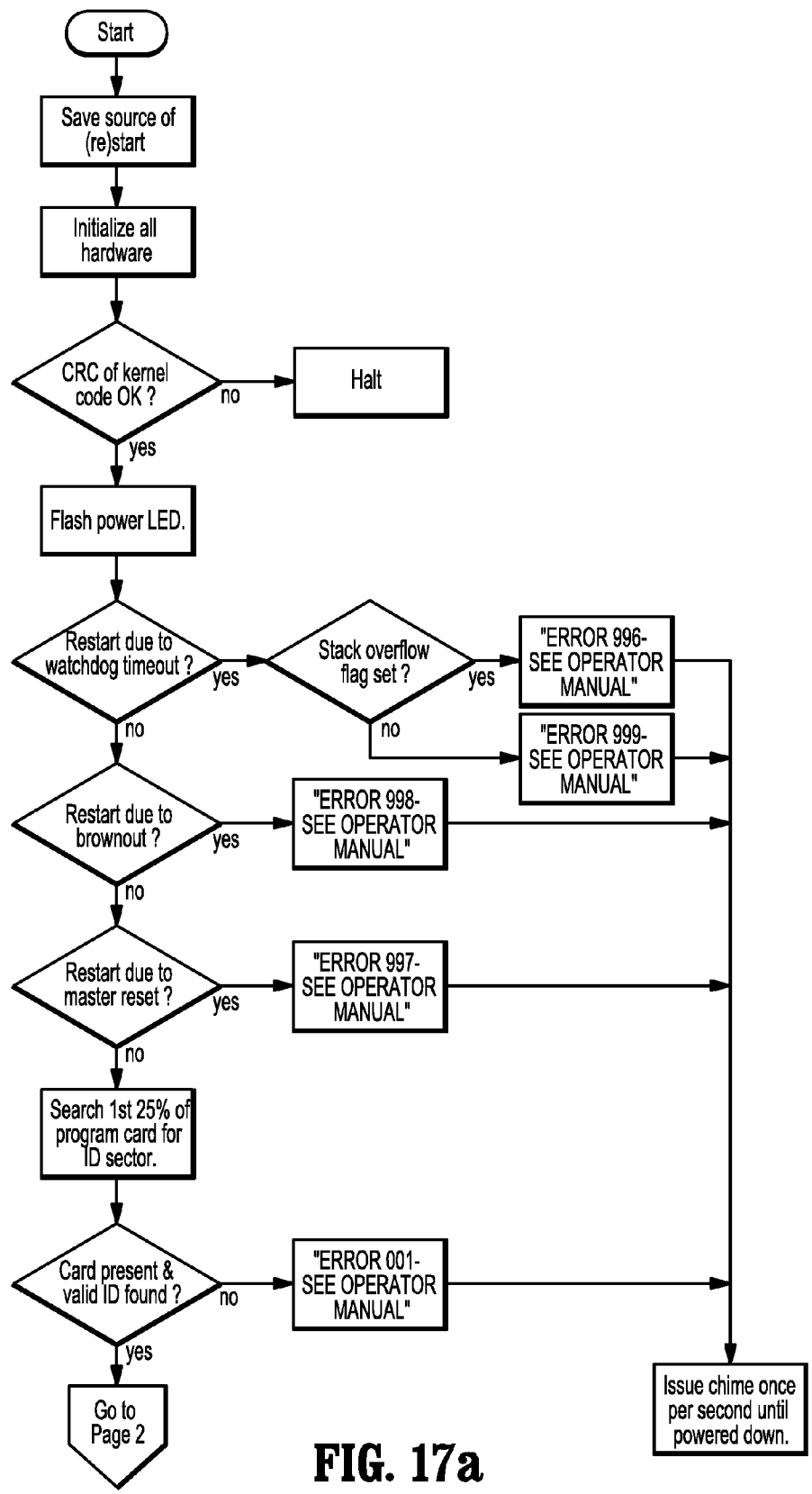
FIGS. 17a to 17d illustrate a flowchart of a second example embodiment of a main operating program for operating the electro-mechanical surgical device illustrated in FIG. 1.
Figure 17B:
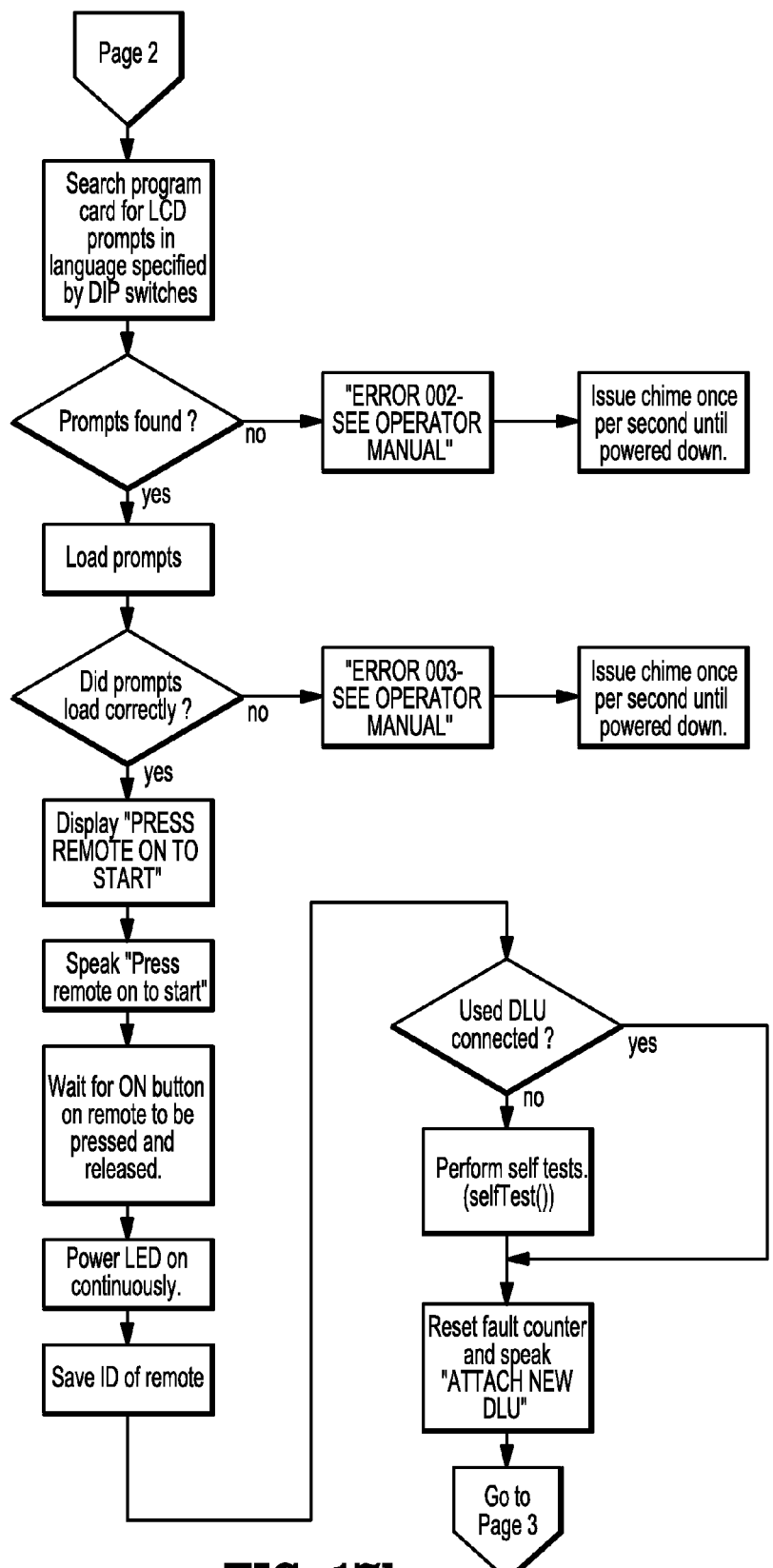
Figure 17C:
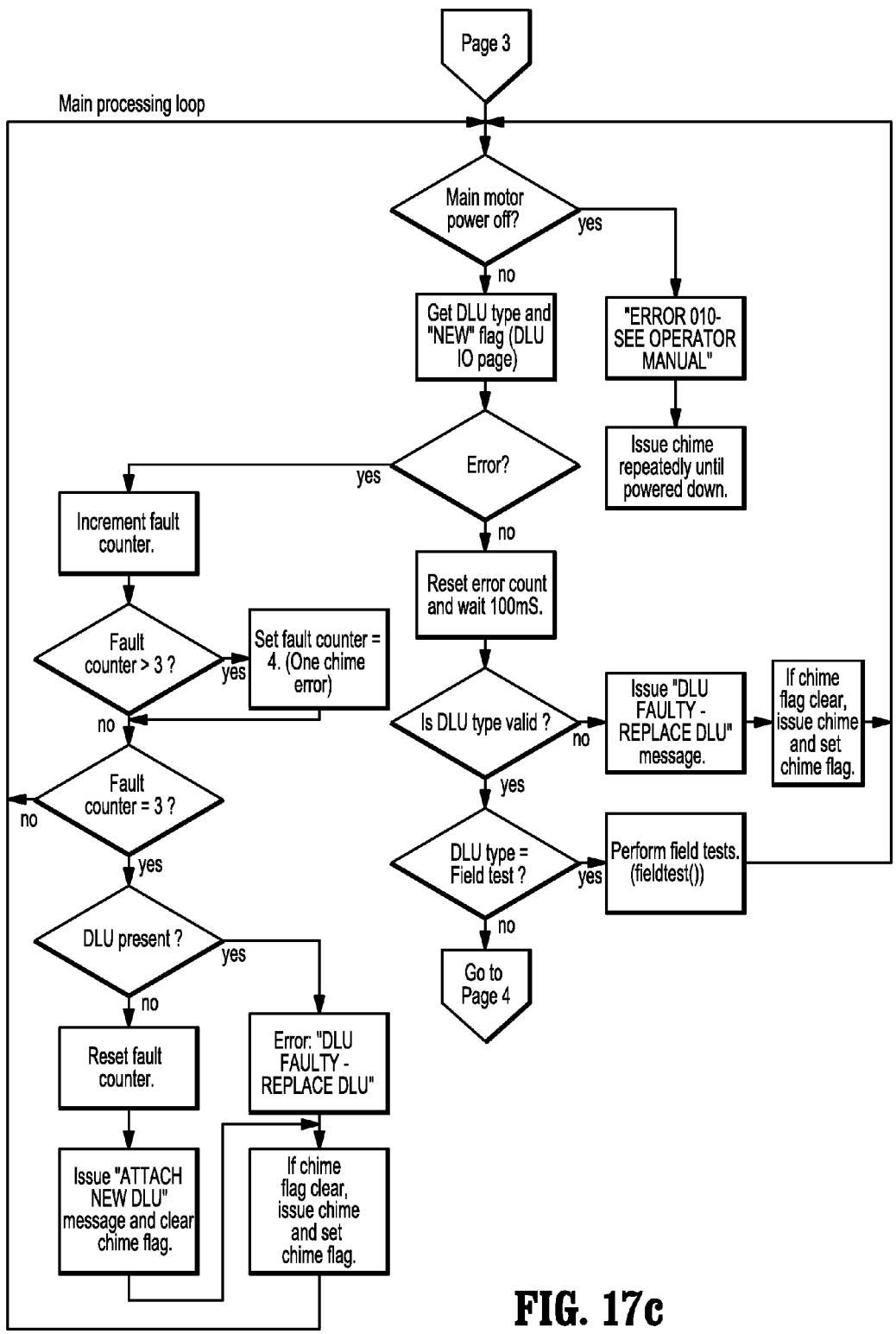
Figure 17D:
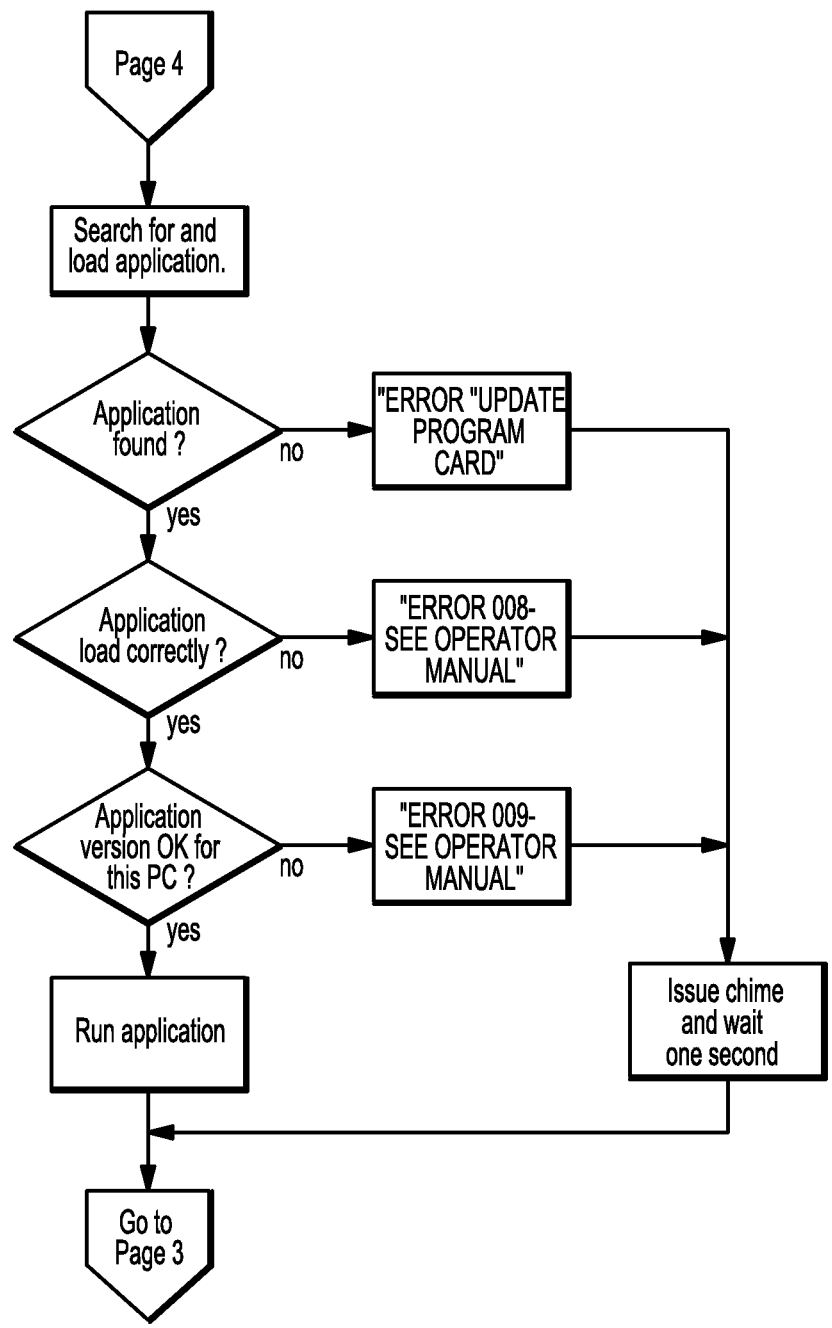

Referring now to FIG. 16, there is seen a flowchart of a first example embodiment of an unclamp routine specific to a circular surgical stapler attachment 250, such as that illustrated in FIG. 9a, or 2250, such as that illustrated in FIGS. 9b and 9c. It should be appreciated that the unclamp routine illustrated in FIG. 16 represents the routine C of step 1016 of the main operating program illustrated in FIG. 13 and that the unclamp routine illustrated in FIG. 16 is specific to a circular surgical stapler attachment 250, such as that illustrated in FIG. 9a, or 2250, such as that illustrated in FIGS. 9b and 9c. It should be further appreciated that other surgical instruments or attachments, such as those enumerated above, may have other unclamp routines associated therewith.

Proceeding from step 1016, a torque limit for an UNCLAMP motor is set in step 1300 to its maximum value. The UNCLAMP motor may correspond to the CLAMP motor as more fully described hereinabove. The UNCLAMP motor may also correspond to the first motor 76 as more fully described hereinabove.

In step 1302, the destination position for the anvil 256 is set to a value representative of its fully unclamped position. The operation of the UNCLAMP motor is initiated in step 1304. In step 1306, it is determined whether the UNCLAMP key has been released. If it is determined in step 1306 that the UNCLAMP key has been released, control proceeds to step 1314. If it is determined in step 1306 that the UNCLAMP key has not been released, it is determined in step 1308 whether the gap between the anvil 256 and the body portion 252 is greater than or equal to a predetermined threshold $G_4$, which is defined in accordance with the destination position set in step 1302. This determination may be made based on the signals generated by the encoders 106, 108, as more fully described above. If it is determined in step 1308 that the gap between the anvil 256 and the body portion 252 is greater than or equal to the predetermined threshold $G_4$, a DLU opened flag is set in step 1310. Control then proceeds to step 1312. If it is determined in step 1308 that the gap between the anvil 256 and the body portion 252 is less than the predetermined threshold $G_4$, it is determined in step 1312 whether the unclamp operation is complete. That is, whether the destination position for the anvil 256 set in step 1302 has been reached. If it is determined in step 1312 that the movement of the anvil 256 is not complete, control returns to step 1306. If it is determined in step 1312 that the movement of the anvil 256 is complete, the operation of the UNCLAMP motor is stopped in step 1314. Control then returns in step 1316 to the main operating program illustrated in FIG. 13.

Figure 18A:
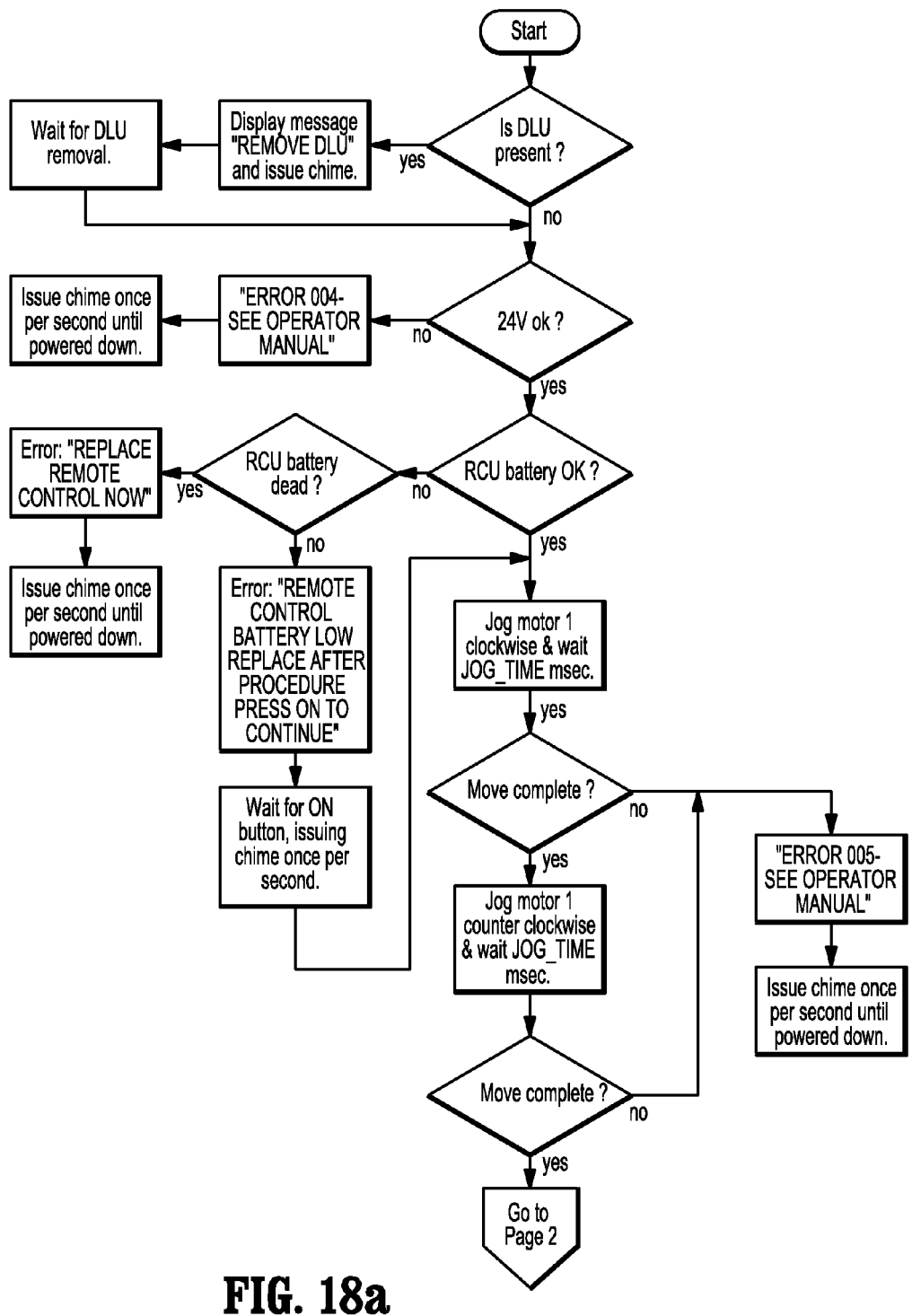
FIGS. 18a and 18b illustrate a flowchart of a self-test operating program for the electro-mechanical surgical device illustrated in FIG. 1.
Figure 18B:
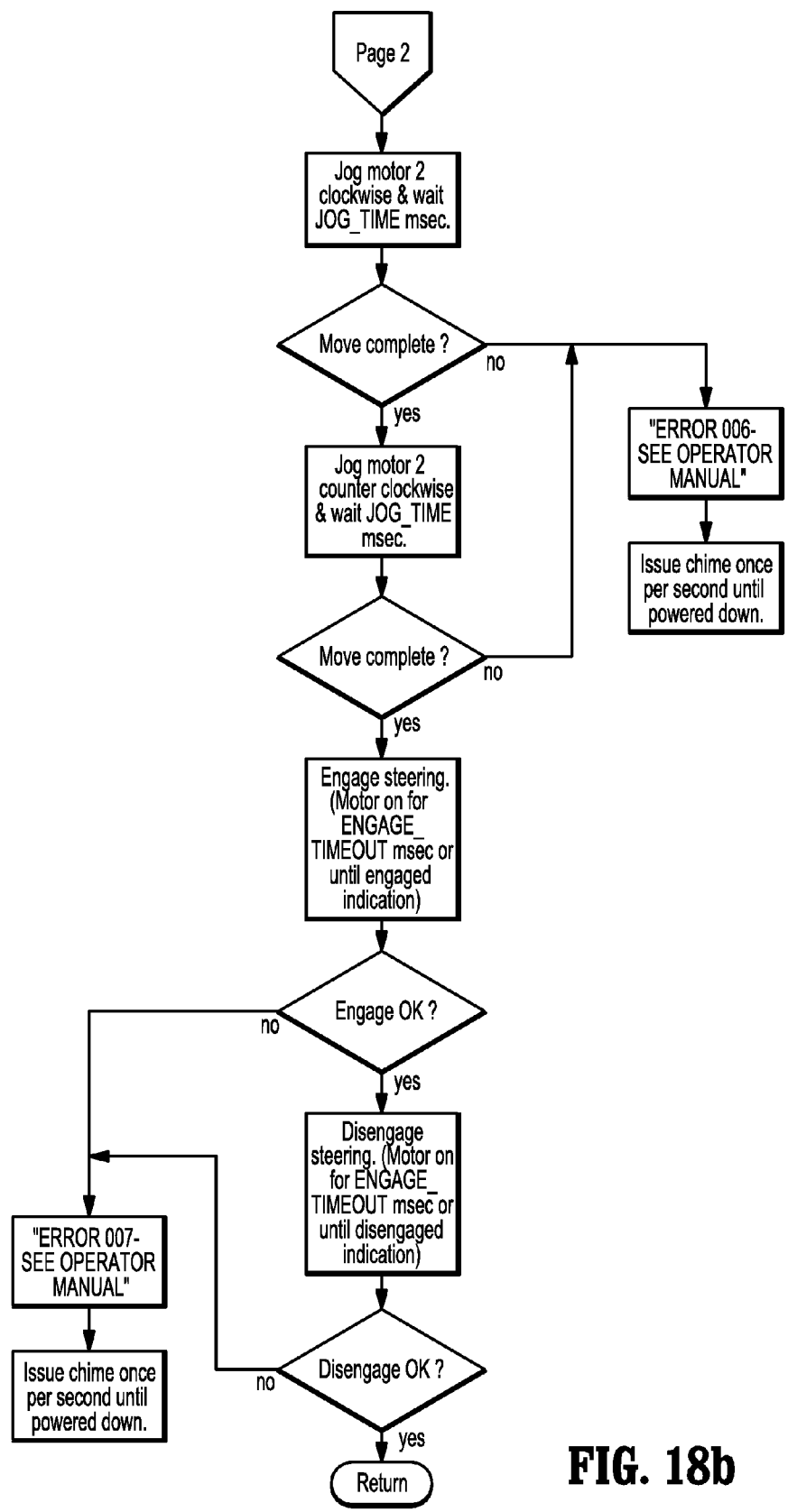
Figure 19A:
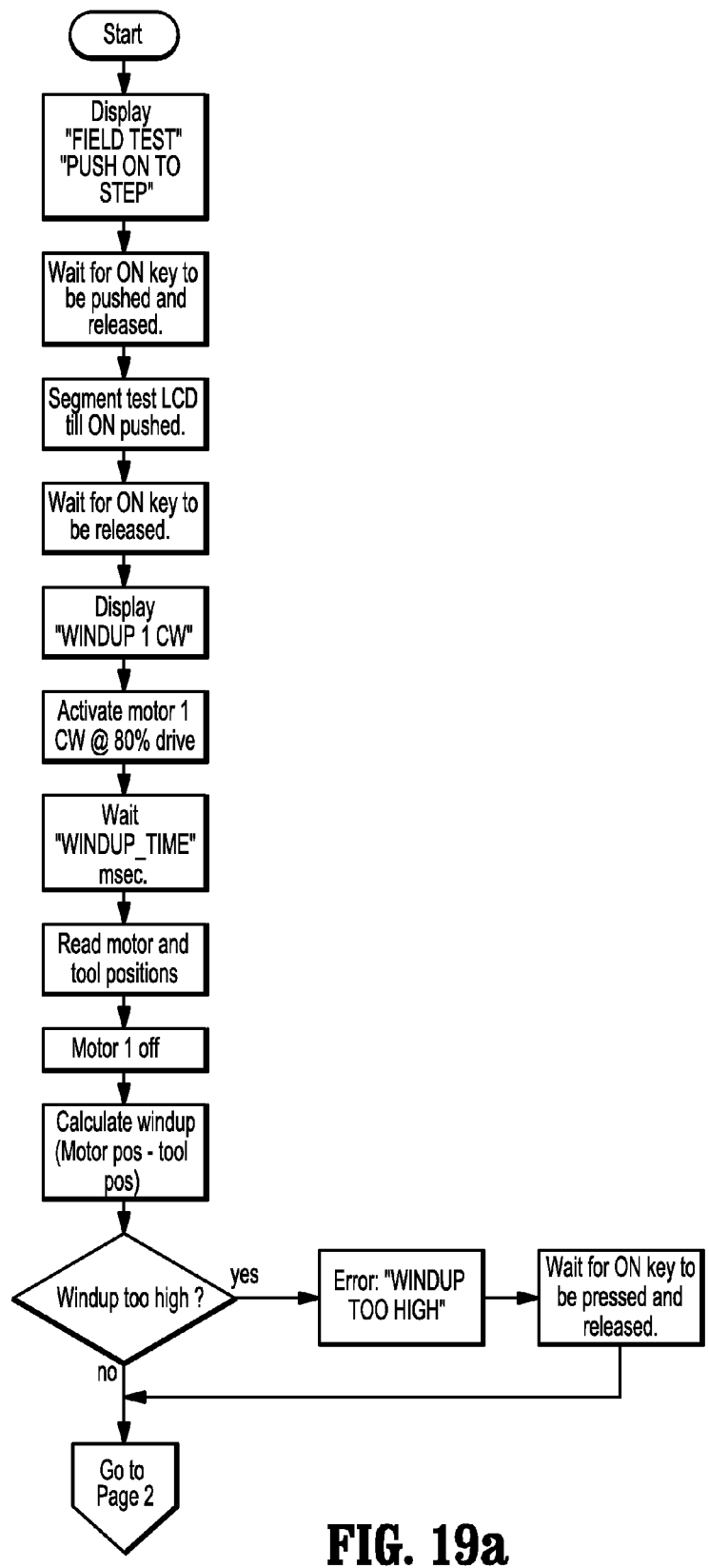
FIGS. 19a to 19e illustrate a flowchart for a field test operating program for the electro-mechanical surgical device illustrated in FIG. 1.
Figure 19B:
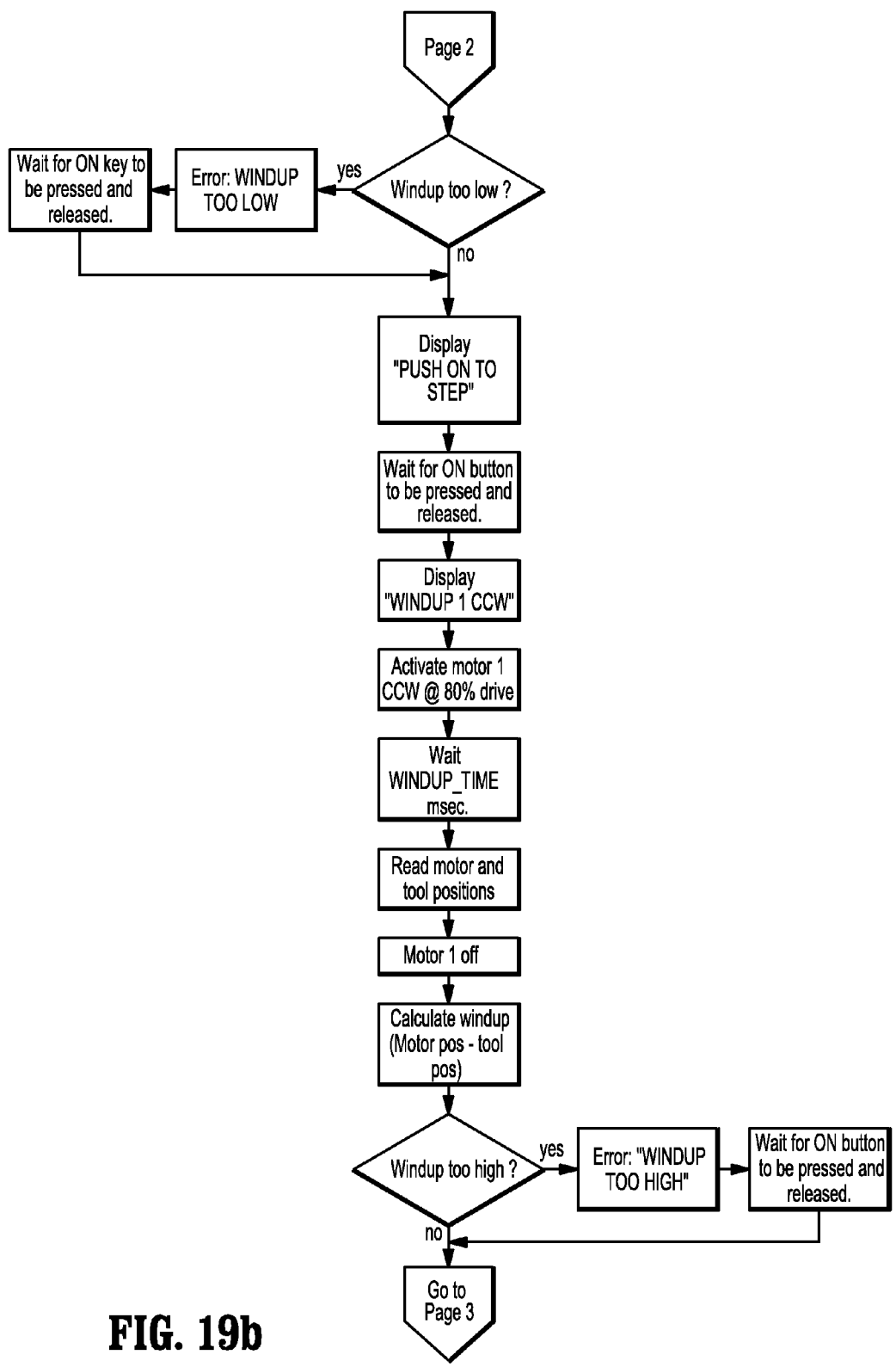
Figure 19C:
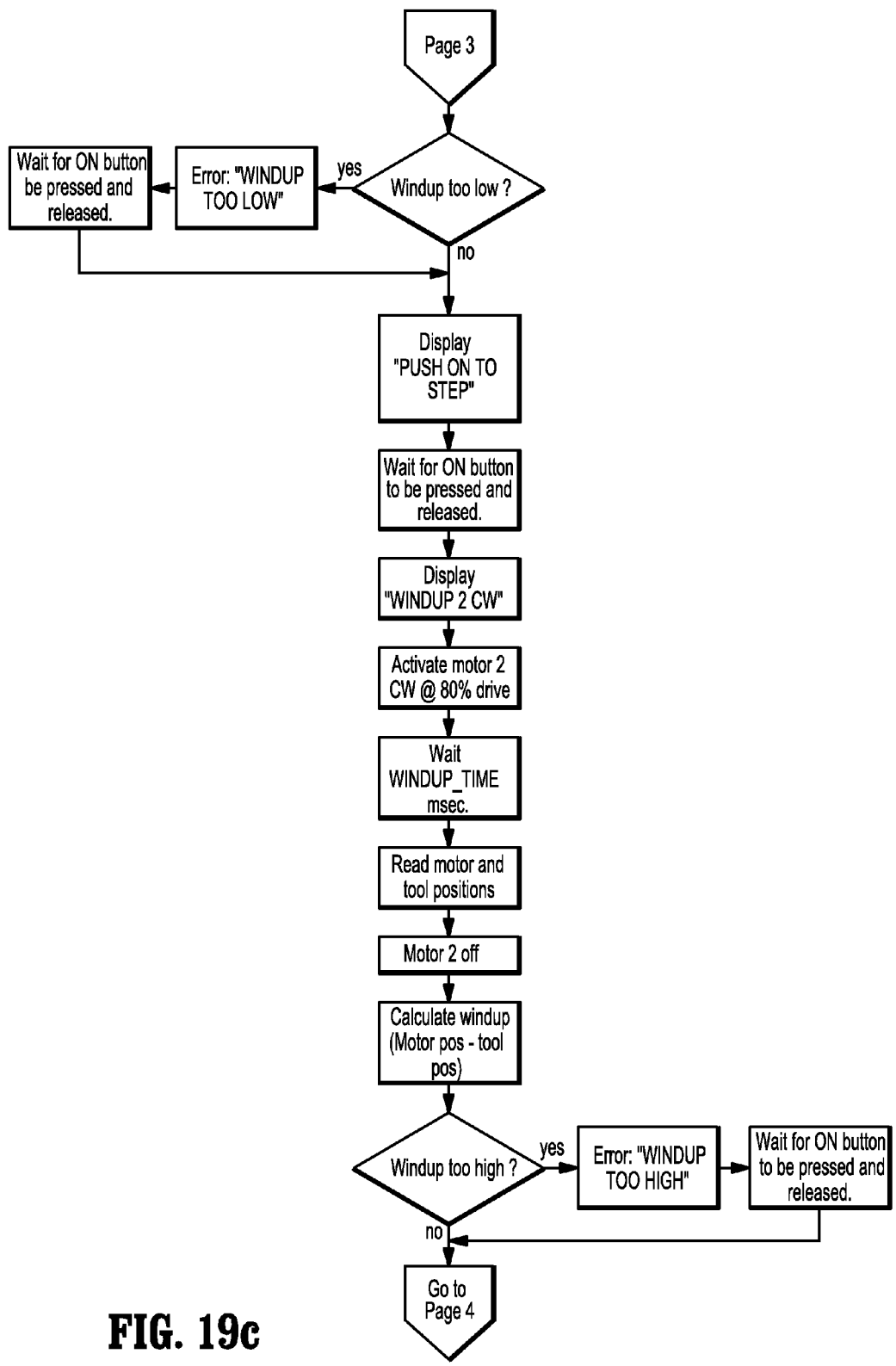
Figure 19D:
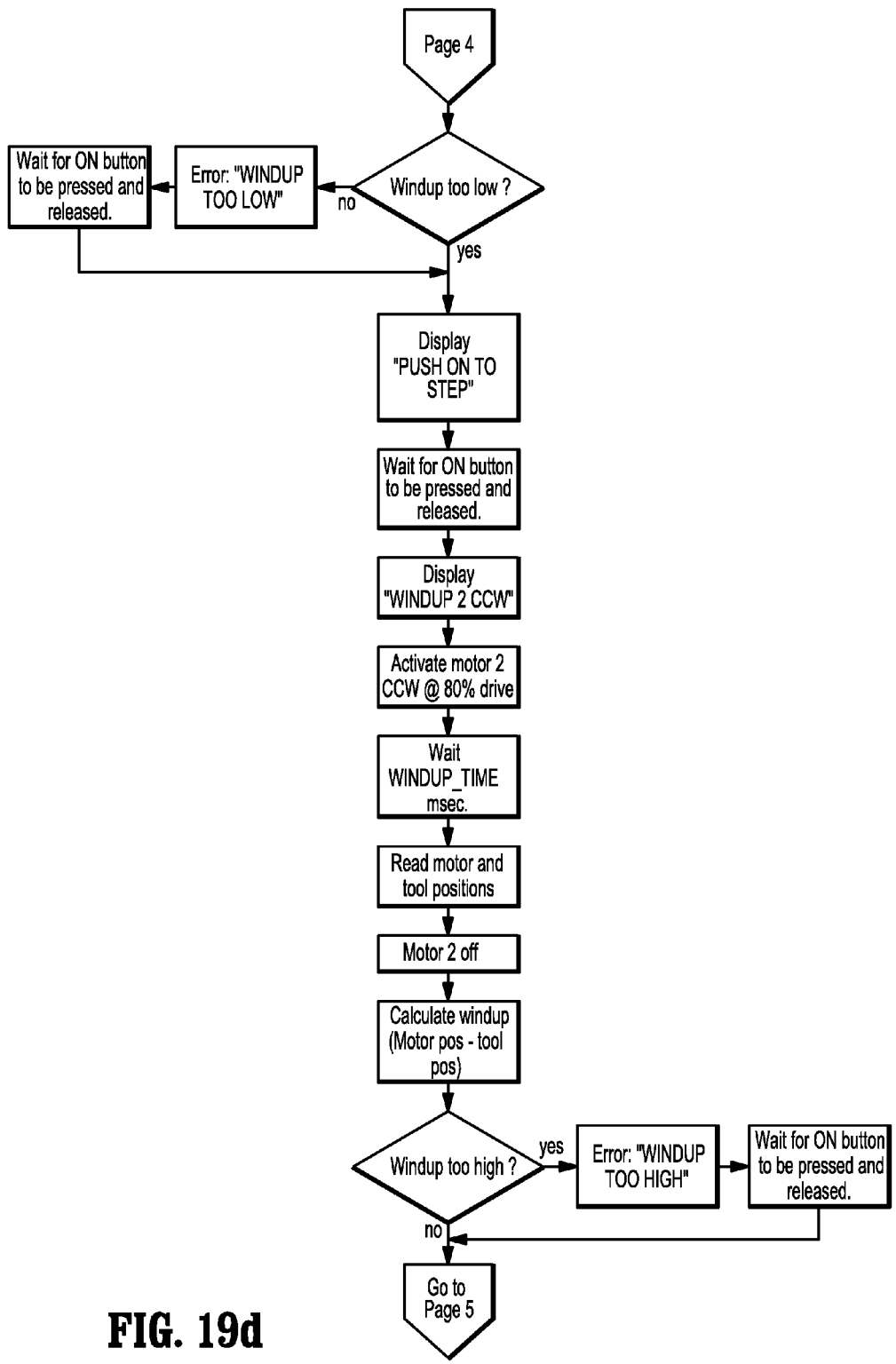
Figure 19E:
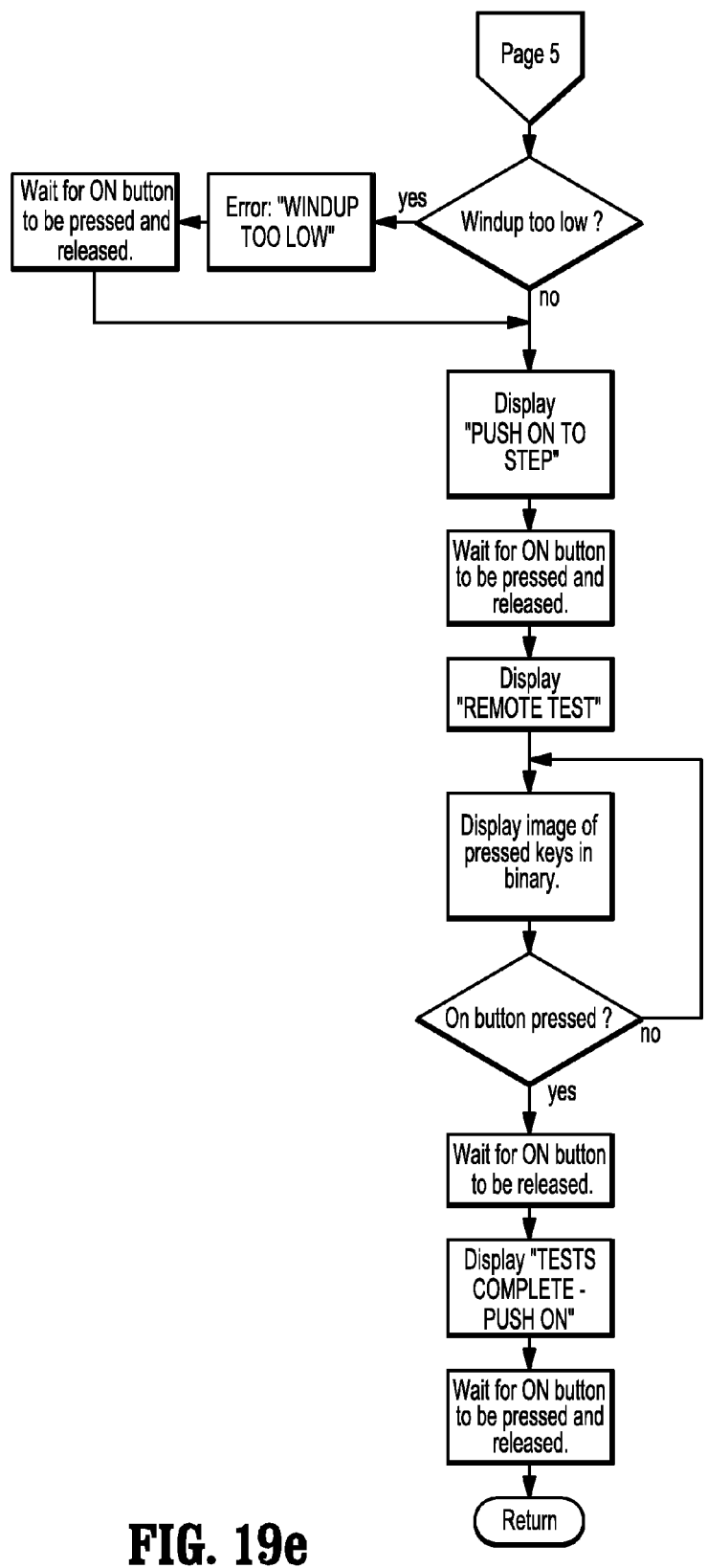
Figure 20A:
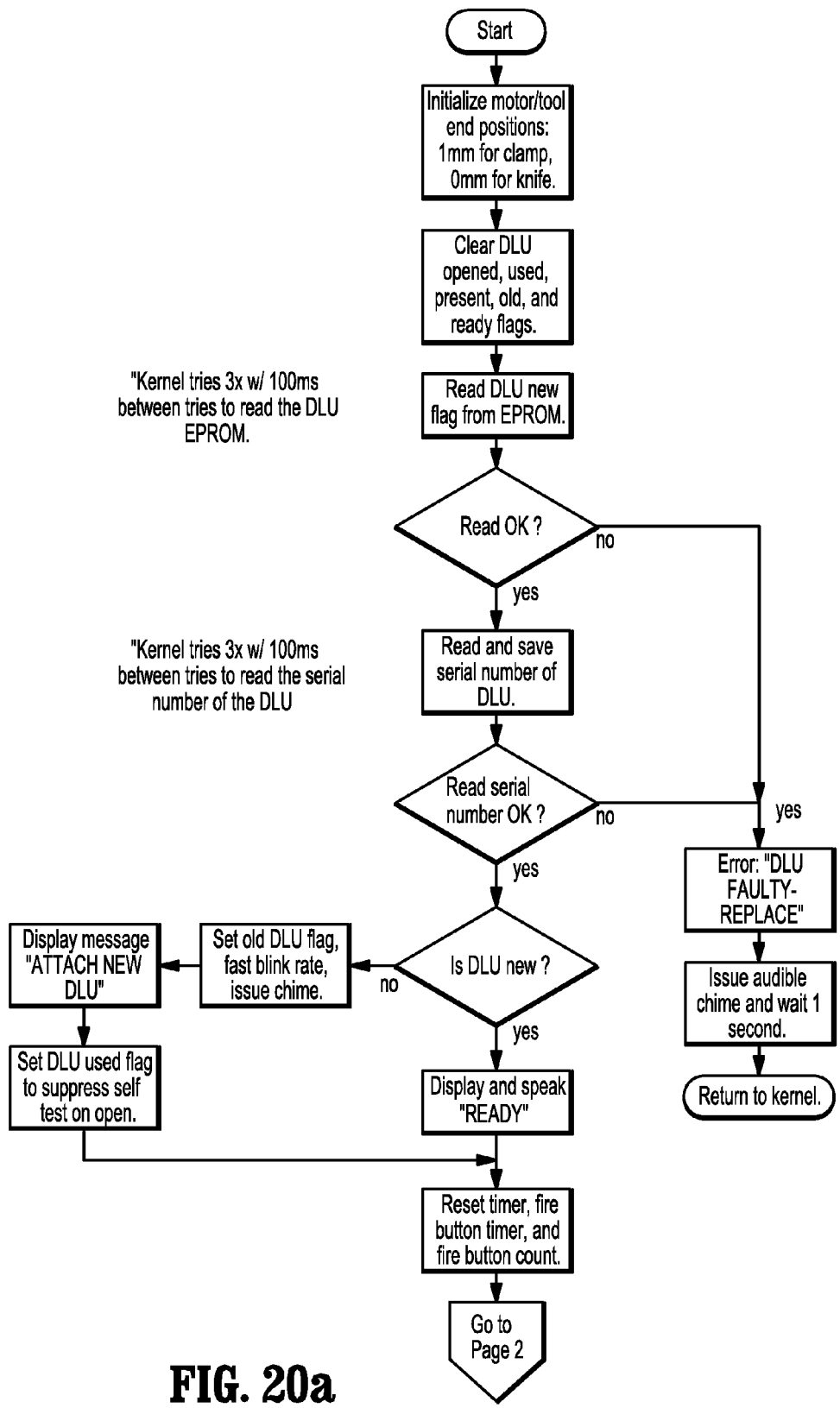
FIGS. 20a to 20c illustrate a flowchart for a main operating program for operating the circular surgical stapler attachment, such as that illustrated in FIGS. 9a to 9c.
Figure 20B:
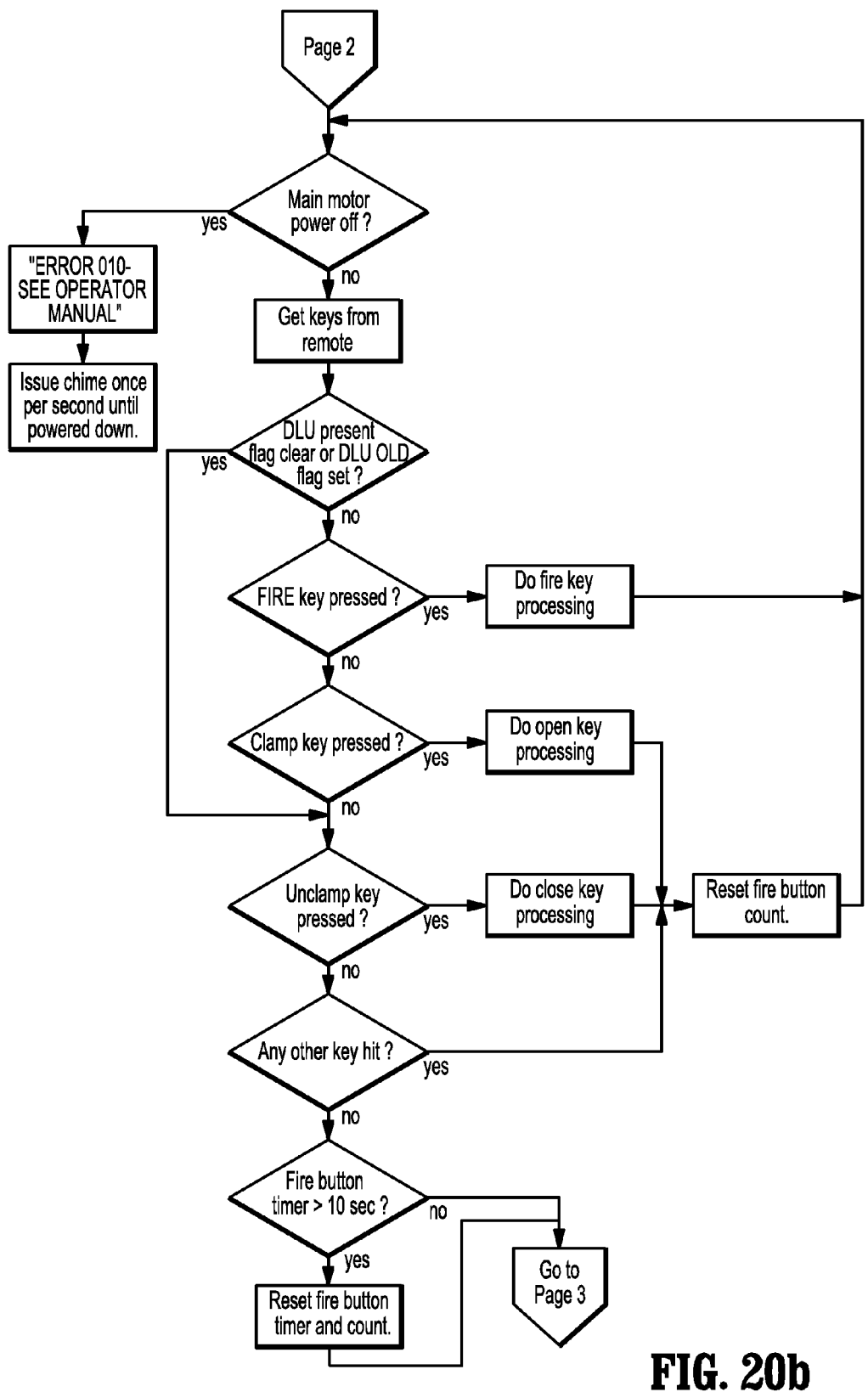
Figure 20C:
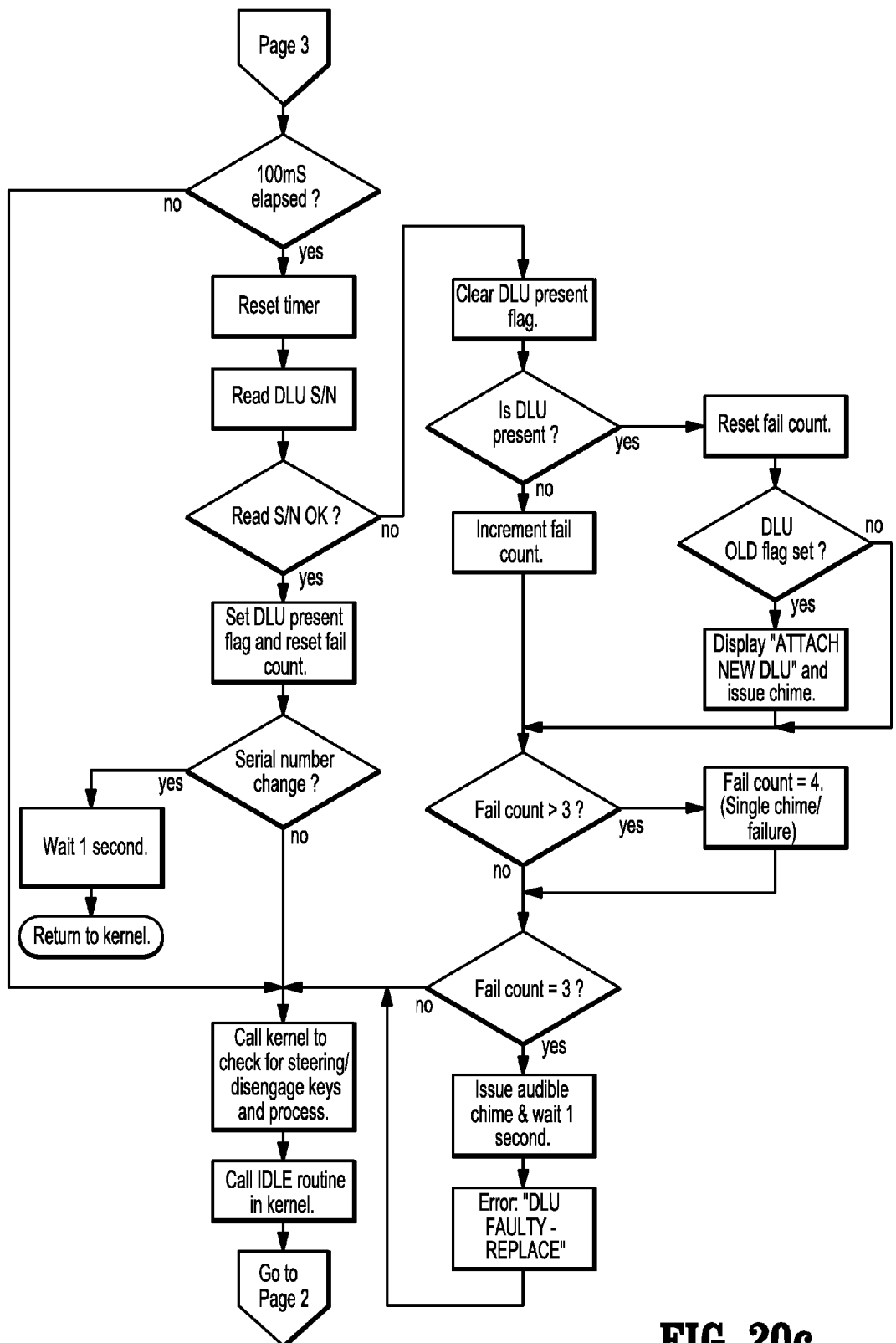
Figure 21A:
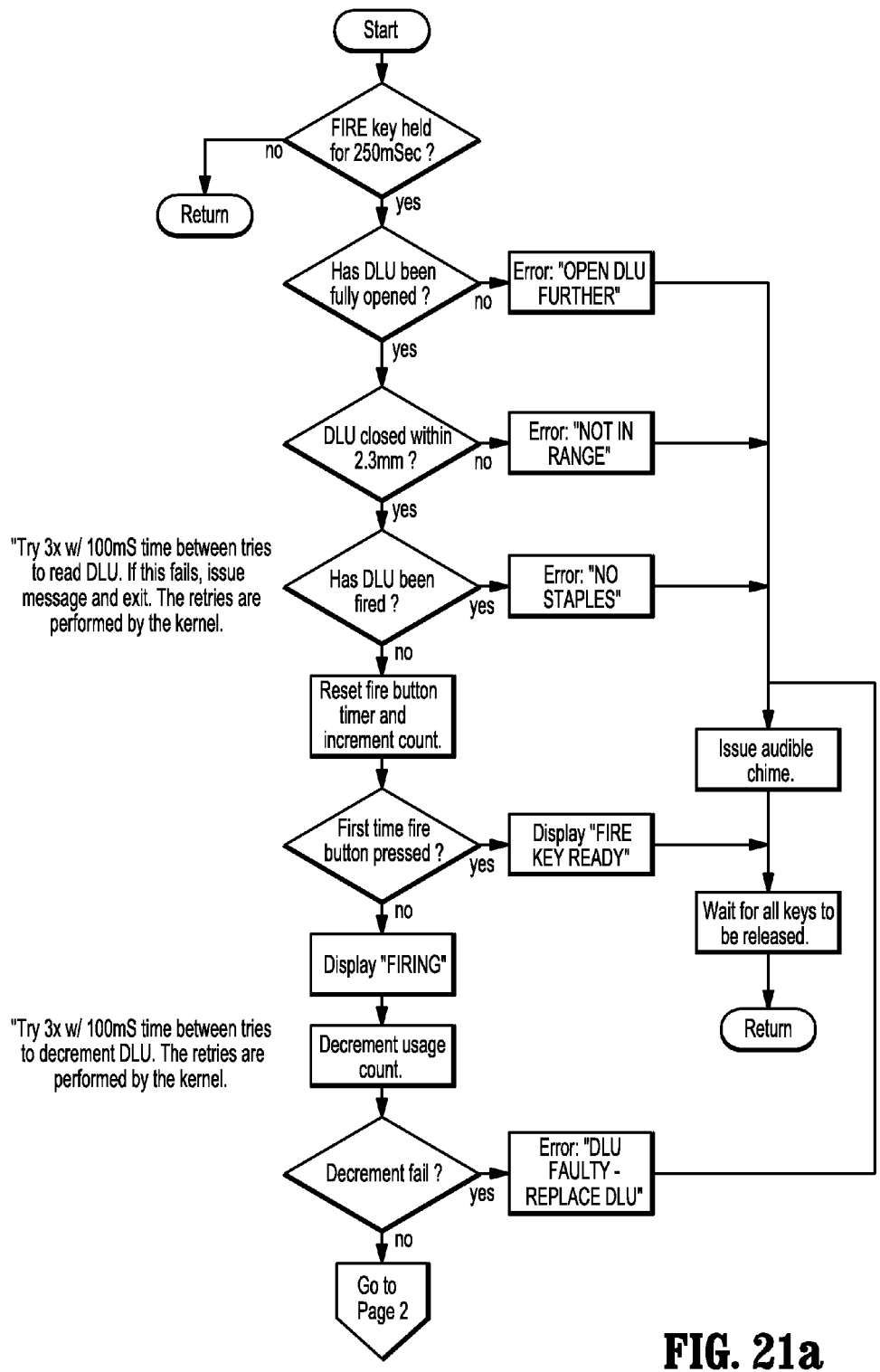
FIGS. 21a to 21d illustrate a flowchart of a second example embodiment of a fire routine for a circular surgical stapler attachment, such as that illustrated in FIGS. 9a to 9c.
Figure 21B:
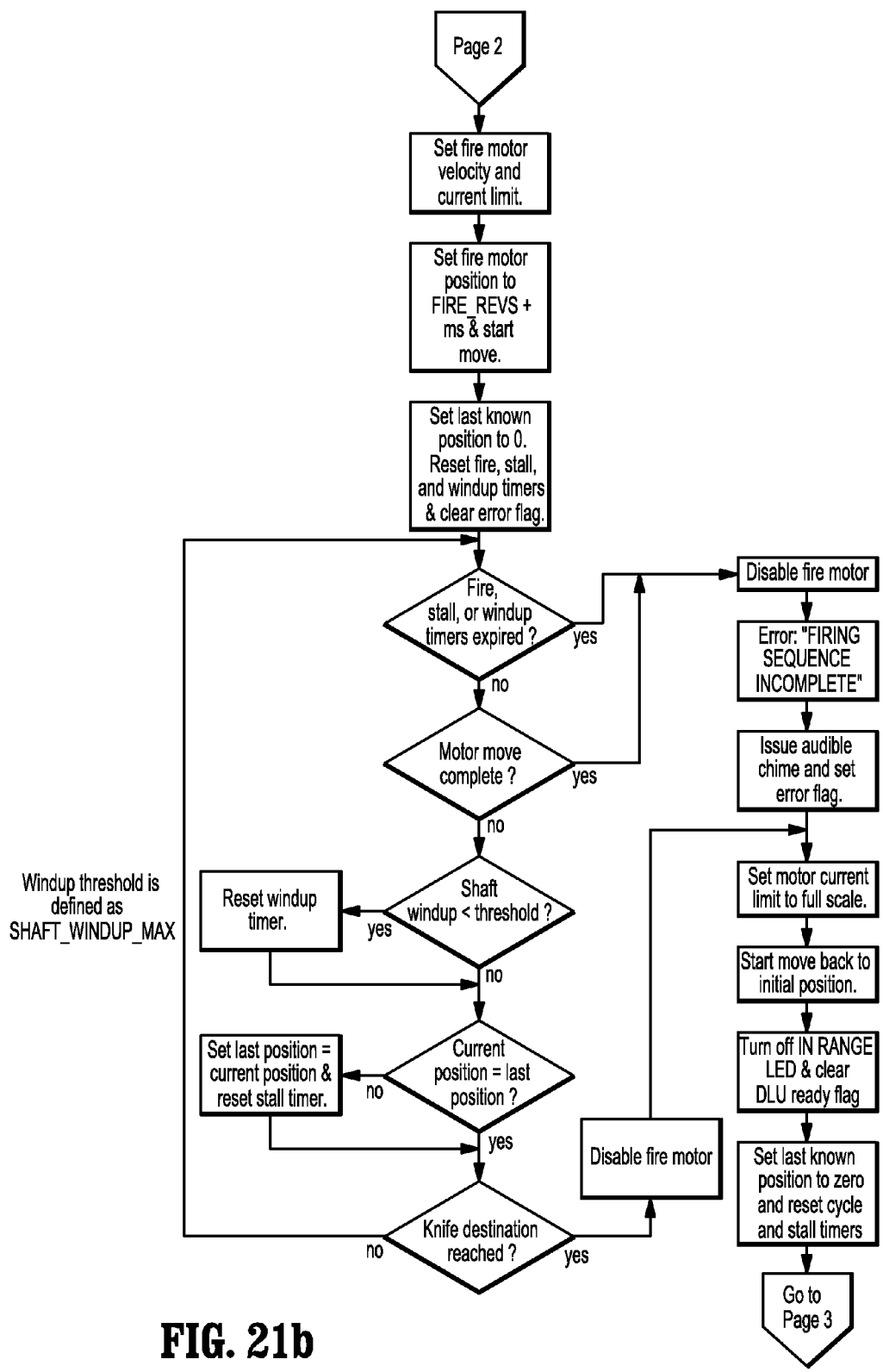
Figure 21C:
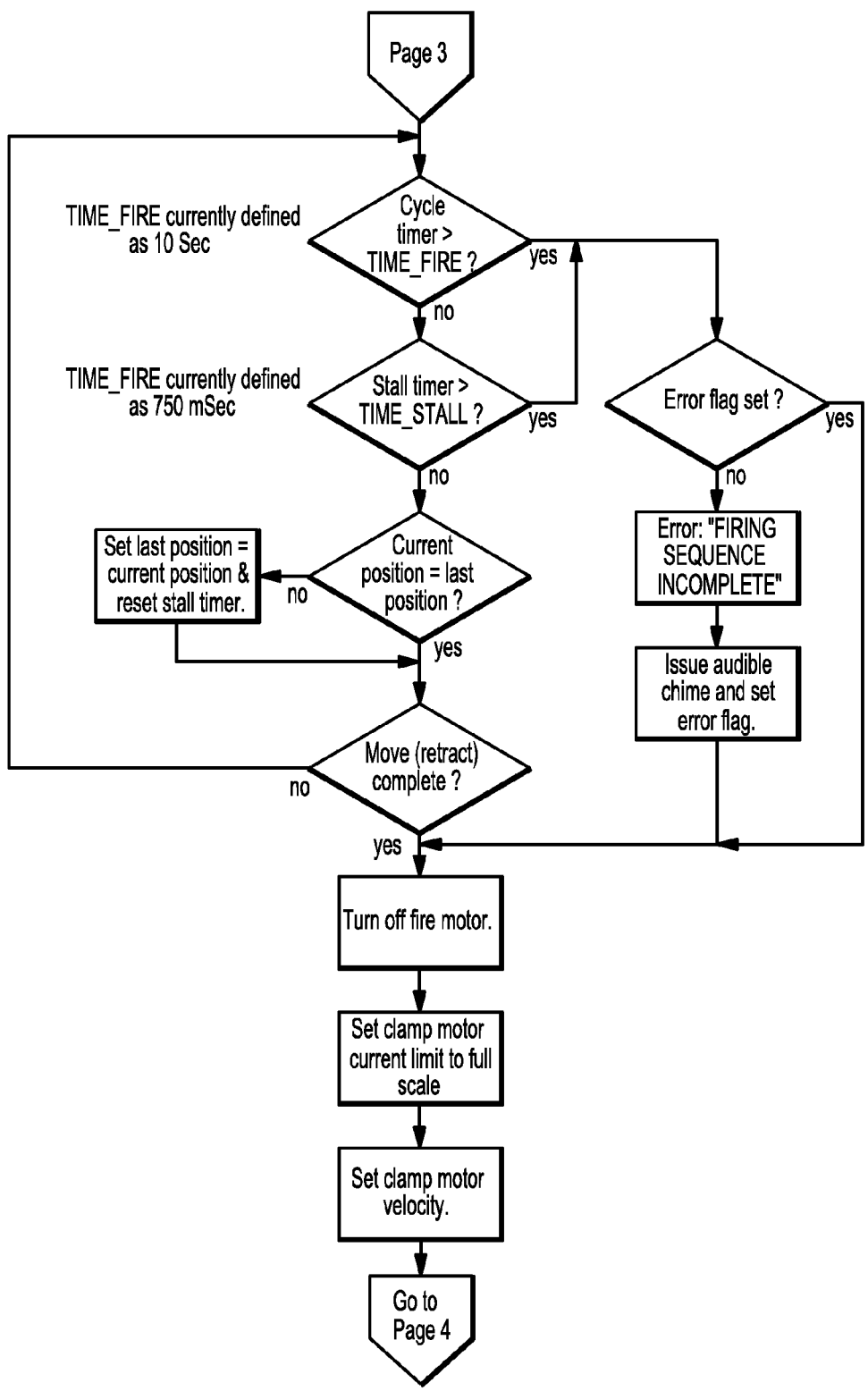
Figure 21D:
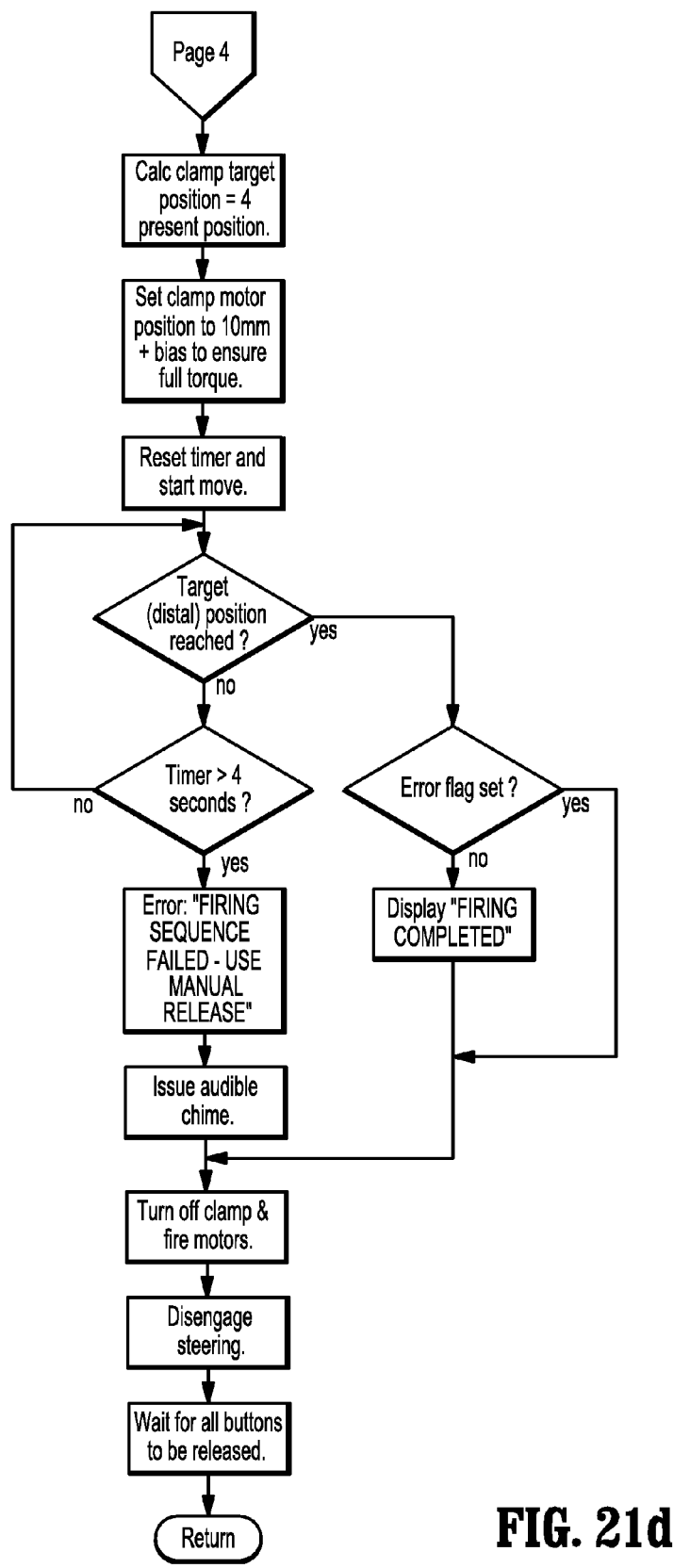
Figure 22A:
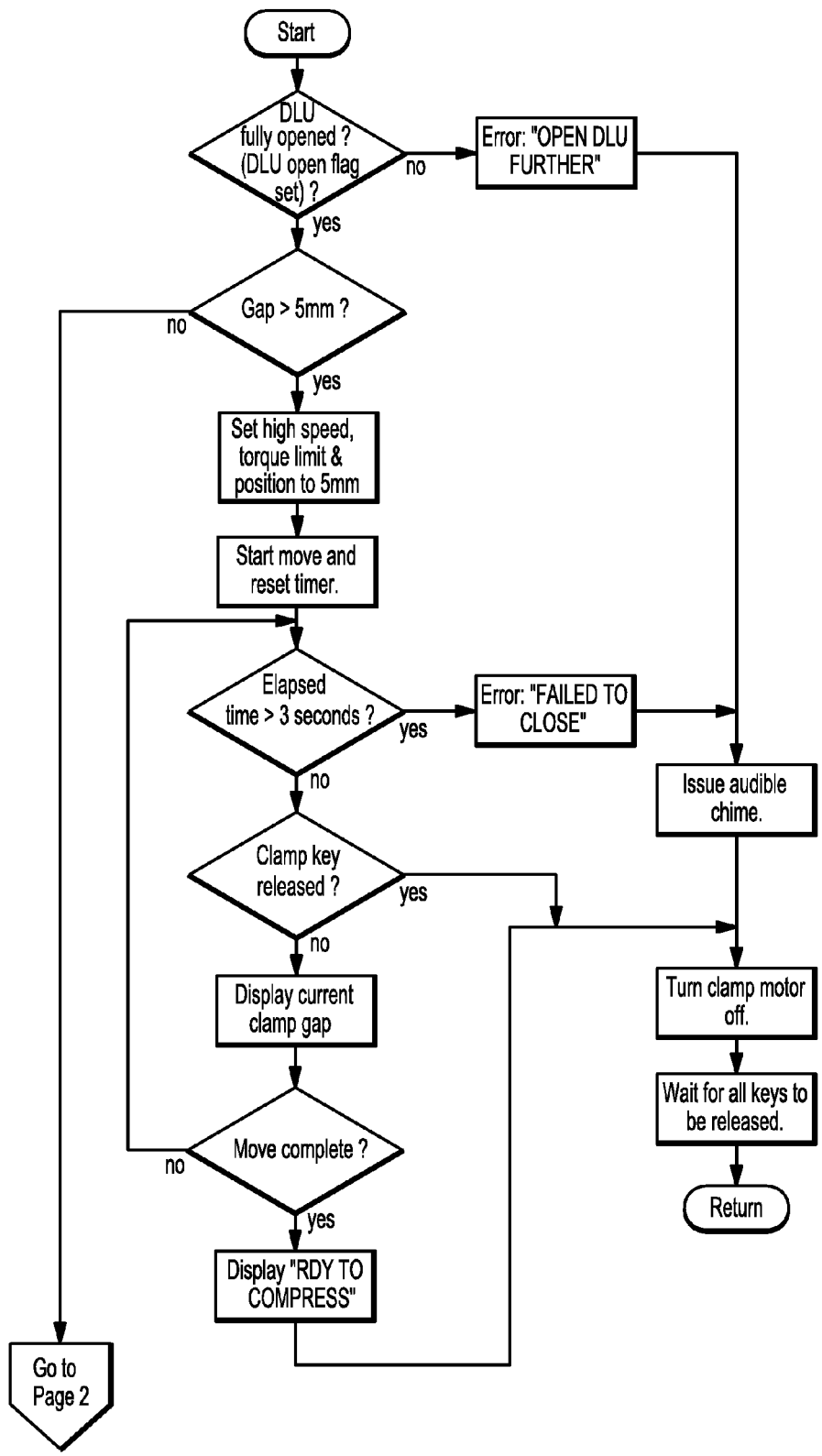
FIGS. 22a and 22b illustrate a flowchart of a second example embodiment of a clamp routine for a circular surgical stapler attachment, such as that illustrated in FIGS. 9a to 9c.
Figure 22B:
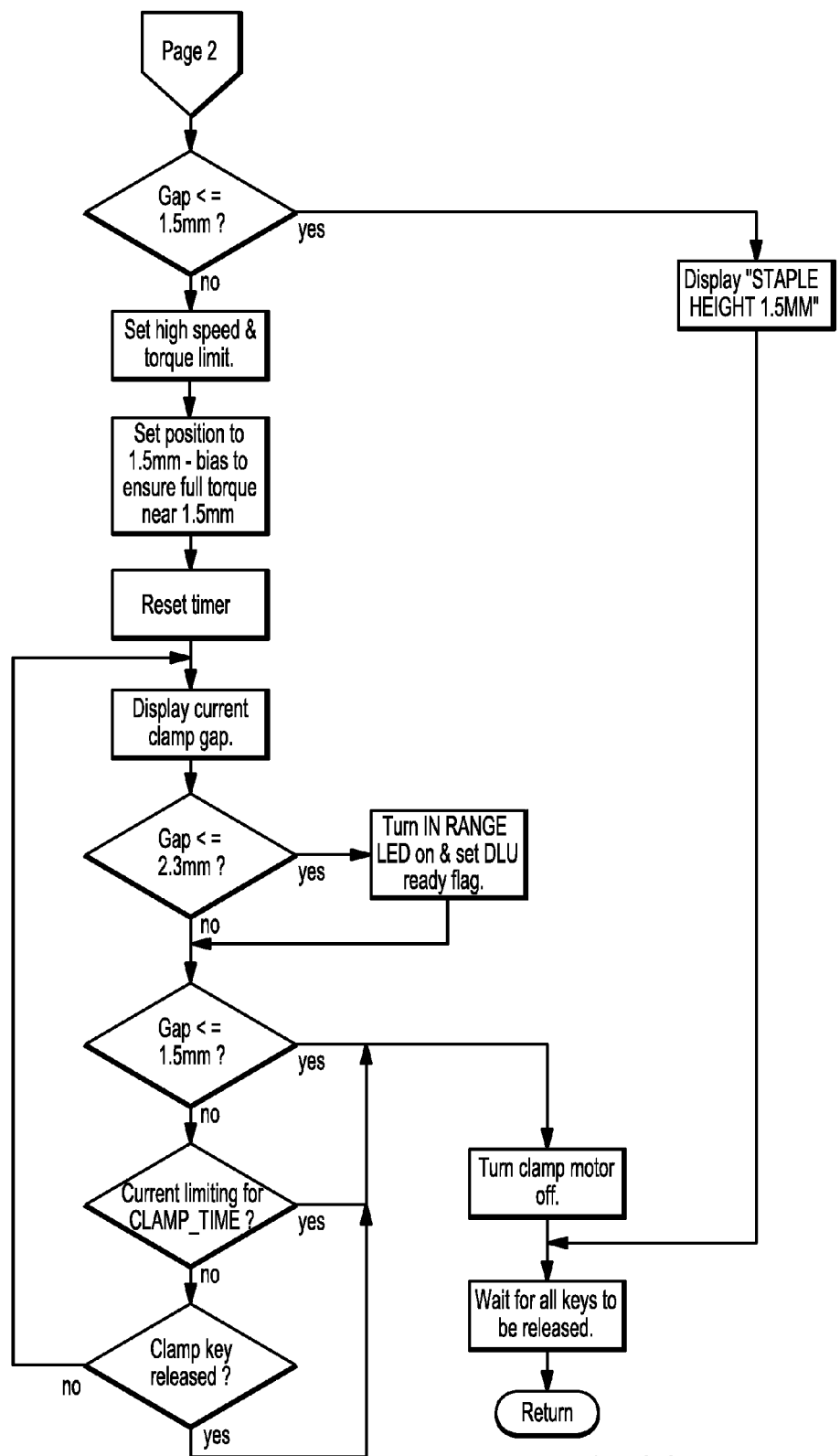
Figure 23A:
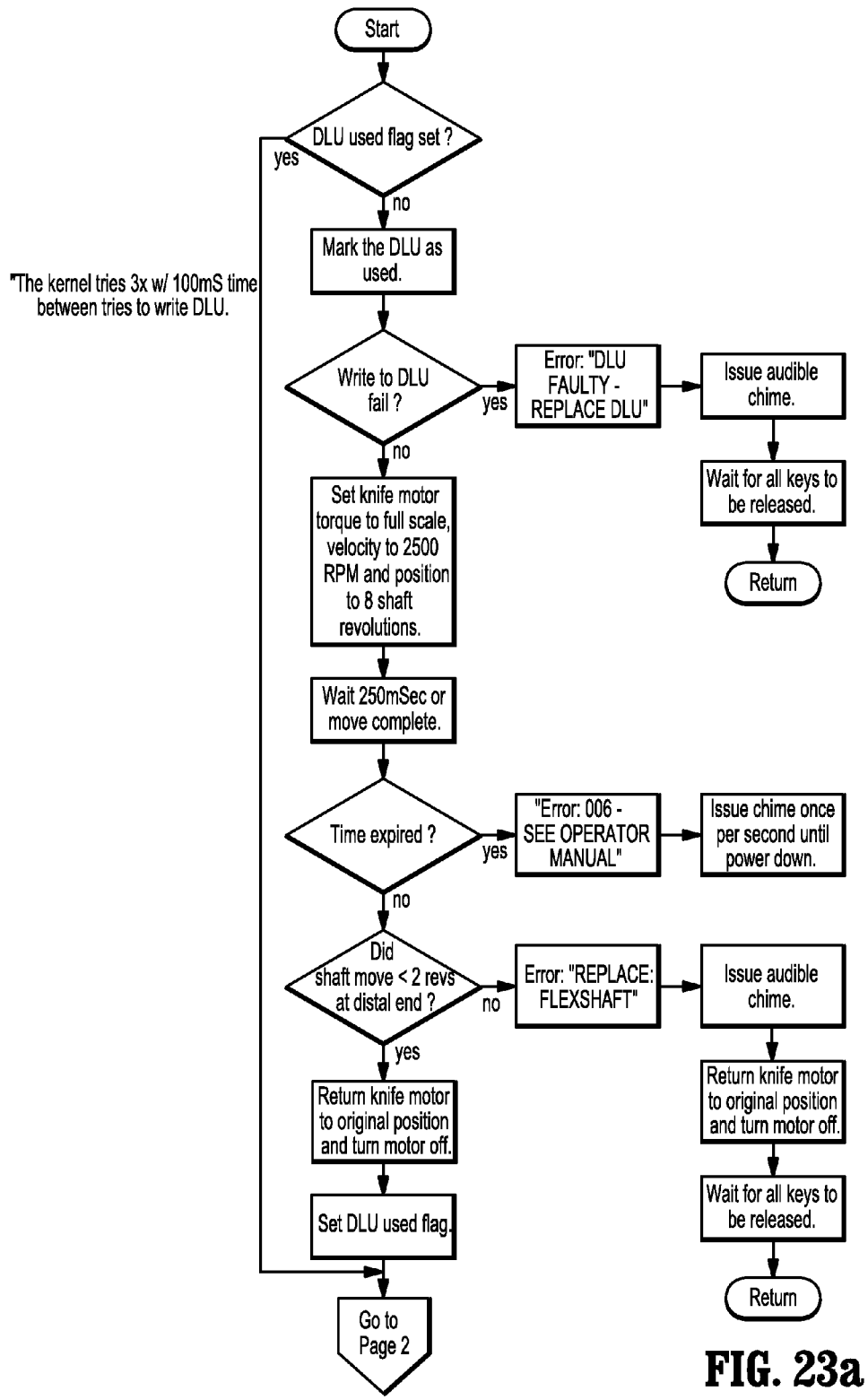
FIGS. 23a and 23b illustrate a flowchart of a second example embodiment of an unclamp routine for a circular surgical stapler attachment, such as that illustrated in FIGS. 9a to 9c.
Figure 23B:
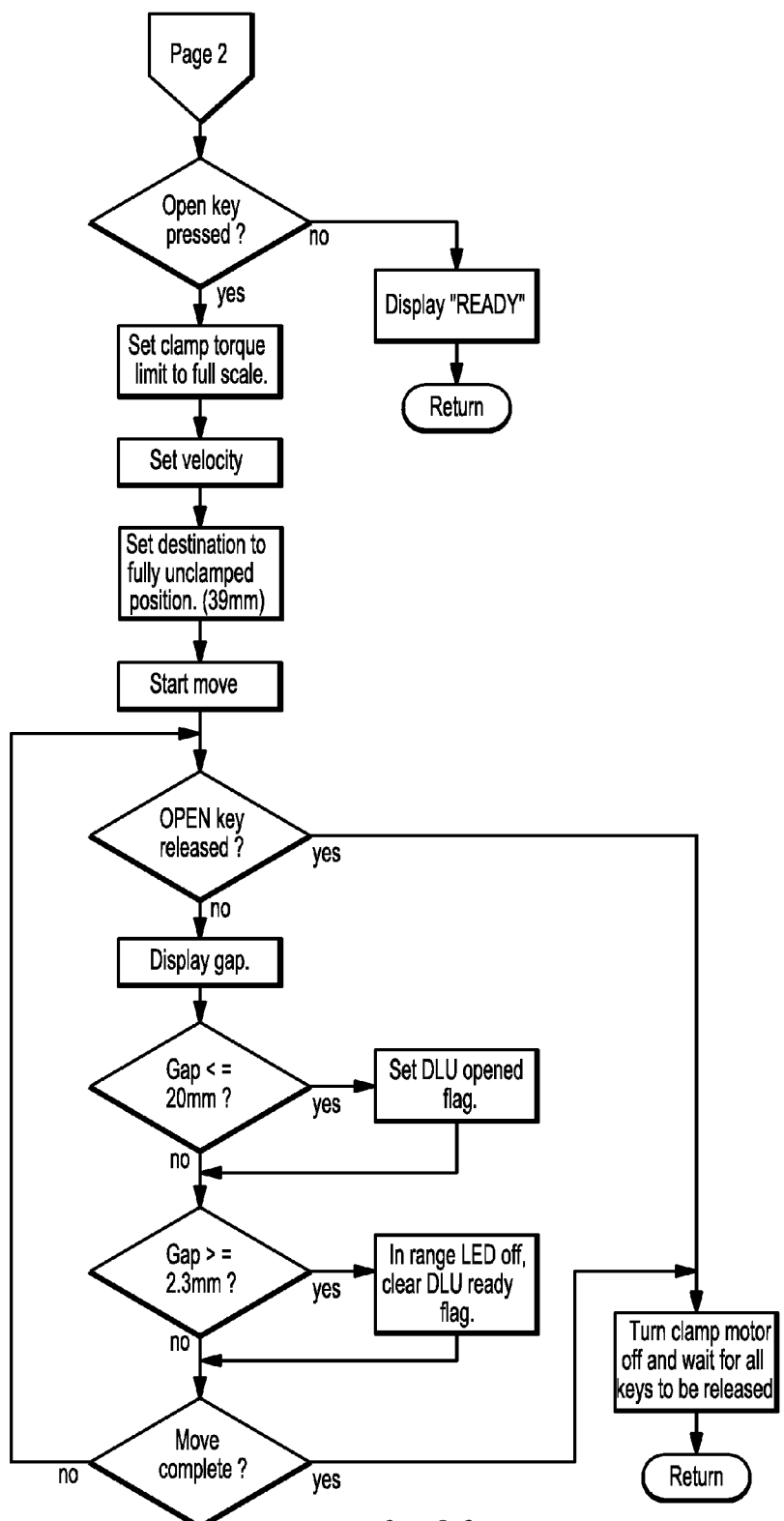

FIGS. 17a to 17d illustrate a flowchart of a second example embodiment of a main operating program for operating the electro-mechanical surgical device illustrated in FIG. 1. FIGS. 18a and 18b illustrate a flowchart of a self-test operating program for the electro-mechanical surgical device illustrated in FIG. 1. FIGS. 19a to 19e illustrate a flowchart for a field test operating program for the electro-mechanical surgical device illustrated in FIG. 1. FIGS. 20a to 20c illustrate a flowchart for a main operating program for operating the circular surgical stapler attachment, such as that illustrated in FIGS. 9a to 9c. FIGS. 21a to 21d illustrate a flowchart of a second example embodiment of a fire routine for a circular surgical stapler attachment, such as that illustrated in FIGS. 9a to 9c. FIGS. 22a and 22b illustrate a flowchart of a second example embodiment of a clamp routine for a circular surgical stapler attachment, such as that illustrated in FIGS. 9a to 9c. FIGS. 23a and 23b illustrate a flowchart of a second example embodiment of an unclamp routine for a circular surgical stapler attachment, such as that illustrated in FIGS. 9a to 9c. The operating programs illustrated in FIGS. 17a to 23b are readily understood by those skilled in the art, and a further description thereof is not included herein.

It should be understood that the operation of the several motors and switch elements as described above with respect to the circular surgical stapler attachment 250, 2250 may be specific to the circular surgical stapler attachment 250, 2250. The motor(s) and/or switch(es) may perform other functions when other surgical instruments or attachments are attached to flexible shaft 20.

It should be appreciated that the surgical instrument or attachment, such as, for example, the circular surgical stapler attachment 250 illustrated in FIG. 9a or the circular surgical stapler attachment 2250 illustrated in FIG. 9b, may be configured to be attached to the flexible shaft 20 either extracorporally or intracorporally. Intracorporal attachment of the surgical instrument or attachment may result in, for example, reduced trauma and improved recovery time. For example, conventional linear cutter devices and linear stapler devices have been used to perform functional end-to-end anastomosis procedures along the intestinal tract. Due to the length, small diameter, flexibility and steerability of the flexible shaft 20, the flexible shaft 20, without any surgical instrument or attachment attached thereto, may be entered into the body, such as, for example, into to gastrointestinal tract via the mouth or the rectum with minimal trauma. It should be appreciated that the flexible shaft 20 may be entered into the body via, for example, a natural orifice, an incision, a cannula, etc. The flexible shaft 20 may then be further inserted into the body and steered, as more fully set forth above, so that the distal end 24 of the flexible shaft 20 is delivered to the treatment site, such as, for example, along the intestinal tract. Then, after the distal end 24 of the flexible shaft 20 has been delivered to the treatment side, the surgical instrument or attachment is attached to the flexible shaft 20 via the second coupling 26 in situ. The surgical instrument or attachment may be inserted into the body for attachment to the flexible shaft 20 via a natural orifice, an incision, a cannula, etc. It should be appreciated that the flexible shaft 20 may be entered into the body via a first orifice and that the surgical instrument or attachment may be entered into the body via a second orifice, the first orifice being the same as or different than the second orifice.

With the surgical instrument or attachment so attached to the flexible shaft 20, an end-to-end anastomosis procedure, for example, may be performed and the flexible shaft 20 with the surgical instrument or attachment attached thereto may thereafter be withdrawn from the body. It should be appreciated that the surgical instrument or attachment may be shaped and configured to minimize trauma during withdrawal thereof. Furthermore, it should be appreciated that the flexible shaft 20 may be caused to become limp prior to withdrawal from the body as more fully described above.

Figure 24A:
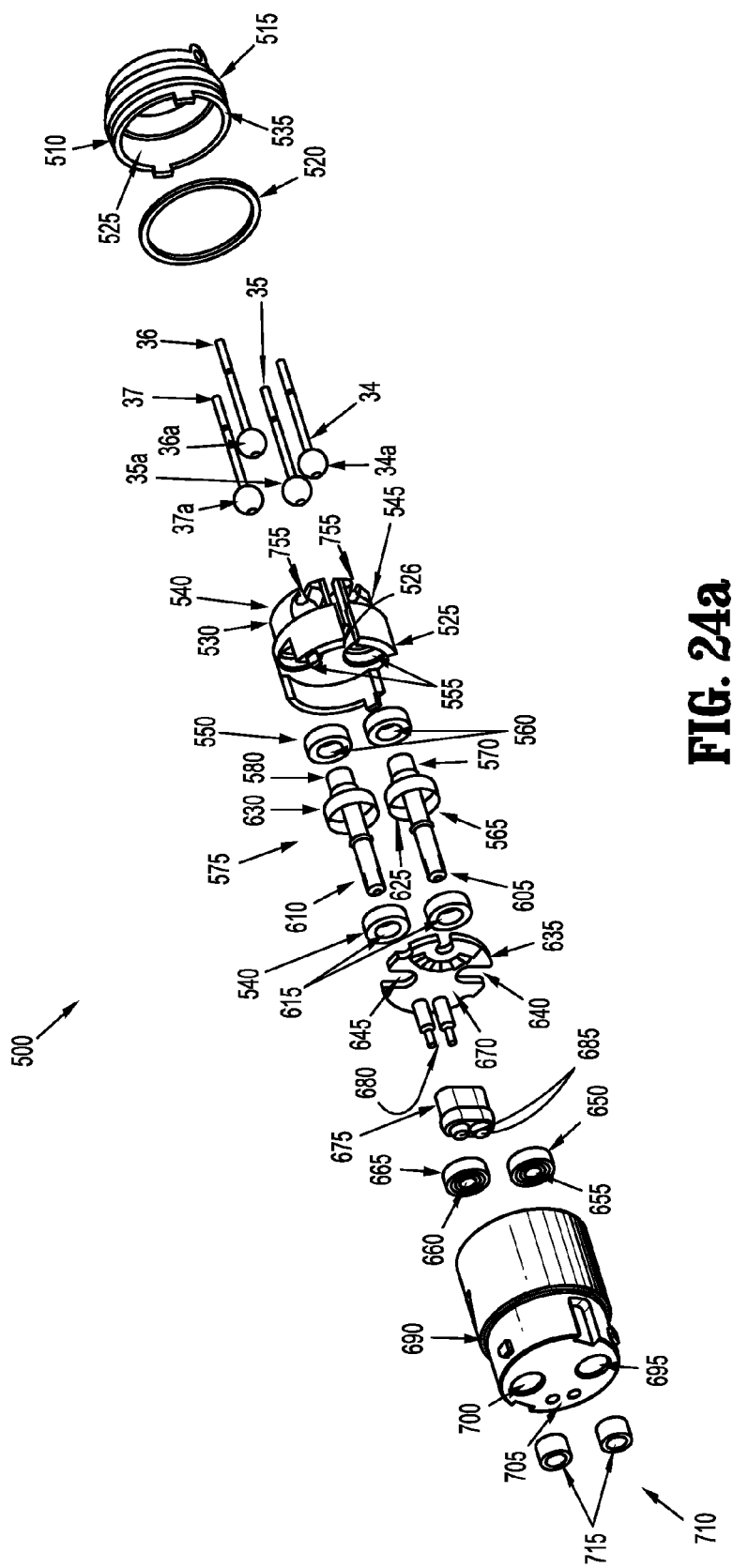
FIG. 24a is an exploded view of an example detachable second coupling.

FIG. 24a shows another example embodiment of second coupling 26 of the flexible shaft 20, this example embodiment of the second coupling being referred to herein as second coupling 500. In accordance with this example embodiment, the second coupling 500 is configured to detachably couple at a proximal side to a distal end of the flexible shaft 20, and is also configured to be disassembled, for, e.g., service, cleaning, refurbishing, repairing, diagnostic purposes, testing purposes, upgrading, etc. Moreover, it will be appreciated that in accordance with this example embodiment, a surgical instrument or attachment may include a coupling that mates with a distal side of the second coupling 26.

Referring now to FIG. 24a, the second coupling 500 includes a distal cover or tip 690 and a link 510 which may be rigidly attached to the distal end 24 of flexible shaft 20. Link 510 includes an annular groove 515 for receiving an O-ring for producing a fluid-tight and air tight seal between the link 510 and the distal cover or tip 690.

The second coupling 500 also includes an insert 535. A proximal end 530 of insert 525 includes slotted cut-outs or cups 755. The cups 755 are configured to receive and hold distal ends of steering cables 34, 35, 36 and 37 (a portion of which is shown in this figure). The insert 525 also includes recesses 555 for receiving bearings 550 and a slot 526.

In this example embodiment, the steering cables 34, 35, 36, and 37 include spherical distal ends 34a, 35a, 36a, and 37a, respectively, for releaseably and tensionally engaging in respective cups 755 of insert 525. During assembly, steering cables 34, 35, 36, and 37, which extend from the distal end 24 of the flexible shaft 20, are passed through a bore 525 of the link 510. Steering the spherical distal ends 34a, 35a, 36a and 37a of cables 34, 35, 36, and 37 tensionally engage the proximal end 530 of an insert 525, urging the proximal end 530 of the insert 525 into the bore 525 of the link 510, lip 535 of the link 510 firmly engaging a proximal face 545 of a distal end 540 of the insert 525.

Bearings 550 are received by recesses 555 of insert 525, e.g., by press fit, friction fit, interference fit, etc. Each bearing 550 includes a bore 560.

The second coupling 500 also includes a first shaft engagement member 565, and a second shaft engagement member 575. A proximal end 570 of the first shaft engagement member 565 and a proximal end 580 of the second shaft engagement member 575 are received in a respective one of the bores 560, e.g., by press fit, frictional fit, interference fit, etc. Each of the first shaft engagement member 565 and the second shaft engagement member 575 includes a respective annular cup member 625, 630.

In this example embodiment, annular magnets 590 are provided. These magnets 590 may be used in conjunction with a Hall sensor or Hall-effect device, as described above. A distal end 605 of the first shaft engagement member 565 and a distal end 610 of the second shaft engagement member 575 extends through a respective bore 615 of the magnets 590. Each of the magnets 590 is non-rotatably connected to the first shaft engagement member 565 and the second shaft engagement member 575 at first cup member 625 of the first shaft engagement member 565 and second cup member 630 of the second shaft engagement member 575, respectively, so as to rotate with the first shaft member 565 and the second shaft member 575.

A printed circuit board ("PCB") 635 is disposed adjacent to magnets 590. PCB 635 has a first slot 640 and a second slot 645 through which the distal end 605 of the first shaft engagement member 565 and the distal end 610 of the second shaft engagement member 575 received. PCB 635 also includes contact pins 680 configured for electrically and logically connection to a surgical instrument or attachment.

In accordance with this example embodiment, PCB 635 is connected to a distal end of a flexible data cable which extends through slot 526 of insert 525, and through bore 525 of link 510. A proximal end of the flexible data cable is configured to connected to the data transfer cable 38 arranged in the flexible shaft 20. This flexible data cable allows data transfer between the data transfer cable 38 (and, accordingly, controller 122), PCB 635 and the surgical instrument or attachment.

A contact pin seal 675 is provided adjacent to PCB 635. Contact pin seal 675 includes bores 685. Contact pin seal 675 receives and seals contact pins 680 of the PCB 635, such that the contact pins 680 extend partially through bores 685.

Bearings 660 and 665 are also provided adjacent to a distal side 670 of PCB 635. The distal end 605 of the first shaft engagement member 565 and the distal end 610 of the second shaft engagement member 575 are each received by a first bore 655 of the first distal ball bearing 650 and a second bore 660 of the second distal ball bearing 665, e.g., by press fit, frictional fit, interference fit, etc.

Second coupling 500 further includes a distal cover or tip 690 provided to cover the arrangement. The distal tip 690 includes a first bore 695, a second bore 700, and two contact pin bores 705. Seals 710 are provided in the first bore 695 and the second bore 700. The distal end 605 of the first shaft engagement member 565 and the distal end 610 of the second shaft engagement member 575 are each received by a first bore 695 and a second bore 700 of a distal tip 690, respectively, and extend therethrough to couple to a surgical instrument or attachment. The distal ends 605 and 610 also pass through the seals 710. The contact pins 680 of the PCB 635 extend partially through the contact pin bores 705 of the distal tip 690 to connect to the surgical instrument or attachment.

Figure 24B:
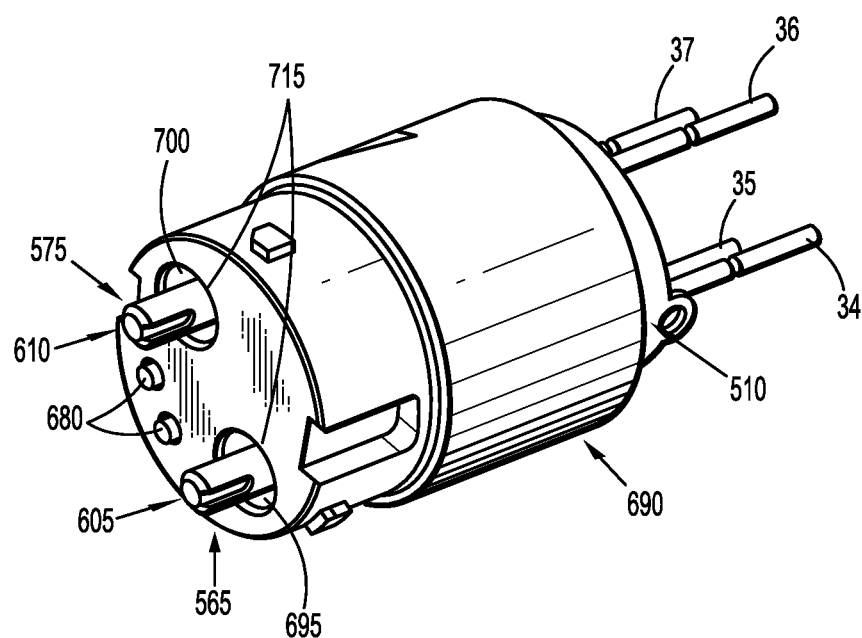

The distal tip 690 is rigidly and firmly attached to the link 510 by a locking mechanism. FIG. 24b illustrates the second coupling 500 in its assembled state.

The locking mechanism for securing the distal tip 690 to the link 510 may include any suitably selected locking mechanism for firmly securing mechanical elements, such as, for example, screws, bolts, rivets, clamps, clips, fasteners, adhesives, epoxies, sealants, a weld, a brazing, a soldered connection, an ultrasonic weld, etc. The locking mechanism may also be removable to allow for disassembly of detachable second coupling 500, so that the flexible shaft may be, for example, cleaned, sterilized, autoclaved, maintained, repaired, parts replaced, refurbished, etc.

Figure 25:
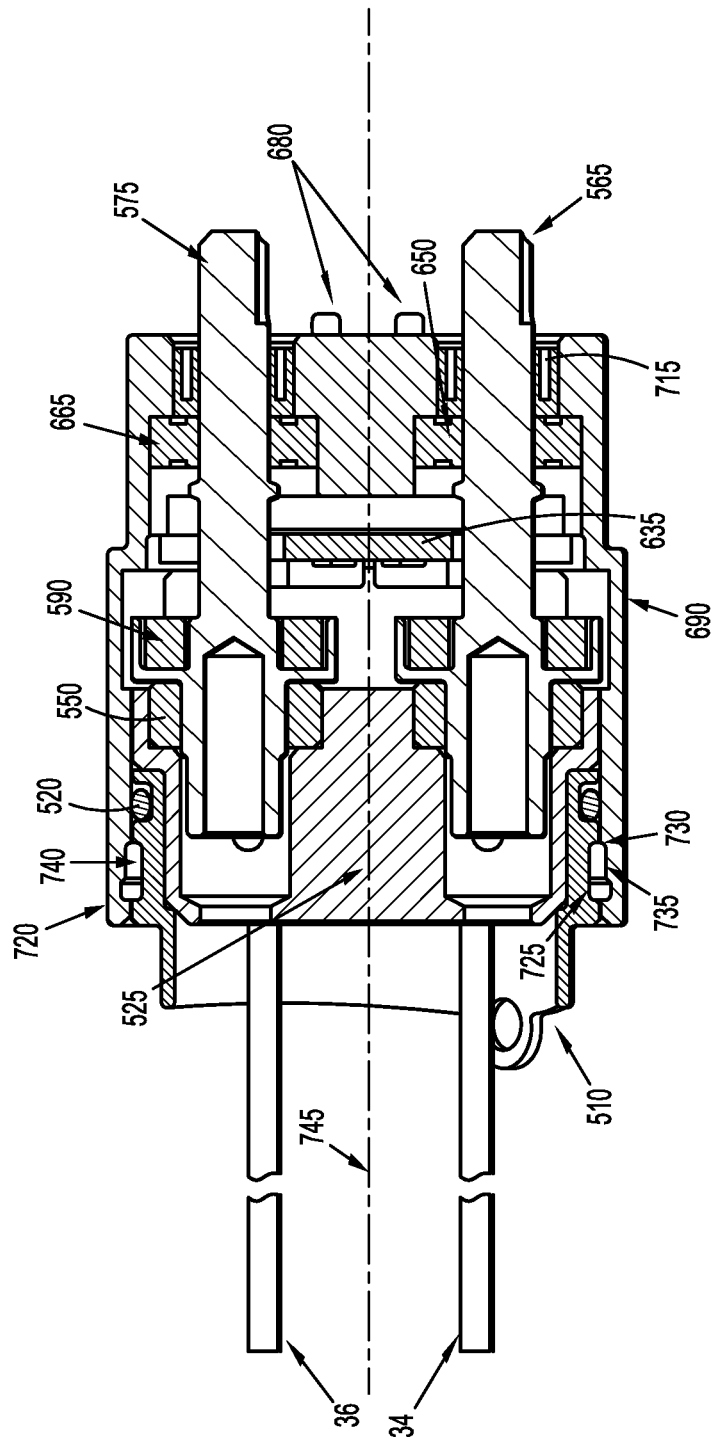
FIG. 25 is a sectional view of a fully assembled example detachable second coupling including a flexible strip locking mechanism.

Referring now to FIG. 25, there is seen a sectional view of an example detachable second coupling 500 fully assembled, including a flexible strip locking mechanism 720 for securing the distal tip 690 to the link 510. The link 510 includes a first annular recess 725 and the distal tip 690 includes a second annular recess 730. When the detachable second coupling 500 is fully assembled, the first annular recess 725 of the link 510 and the second annular recess 730 of the distal tip 690 are situated adjacent to one another, forming an annular cavity 735. A annular strip 740 substantially fills the cavity 735 and prevents movement of the distal tip 690 relative to the link 510, e.g., along longitudinal axis 745, thereby firmly securing the distal tip 690 to the link 510. The annular strip 740 may be flexible and may be formed of, e.g., metal, e.g., stainless steel.

Figure 26A:
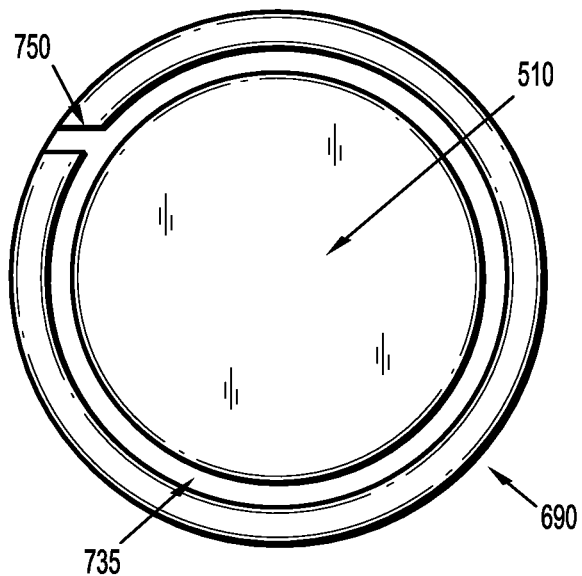
FIGS. 26a to 26d illustrates an operational sequence for locking and unlocking the fully assembled example detachable second coupling illustrated in FIG. 25.
Figure 26B:
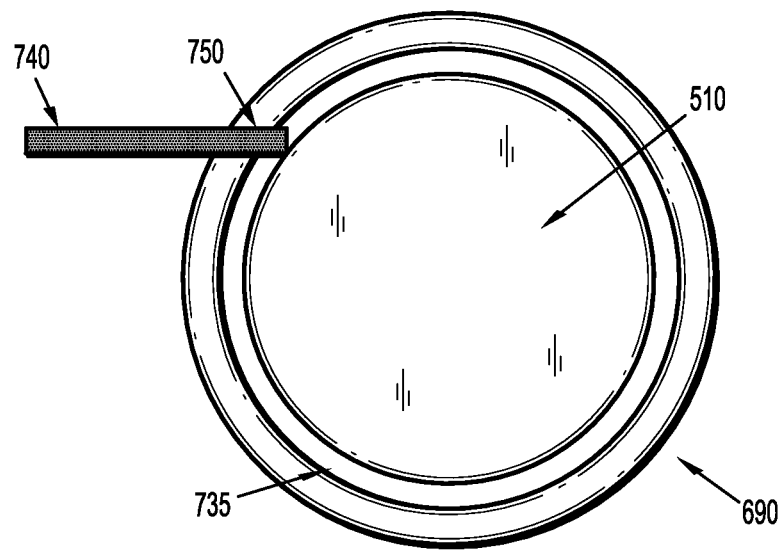
Figure 26C:
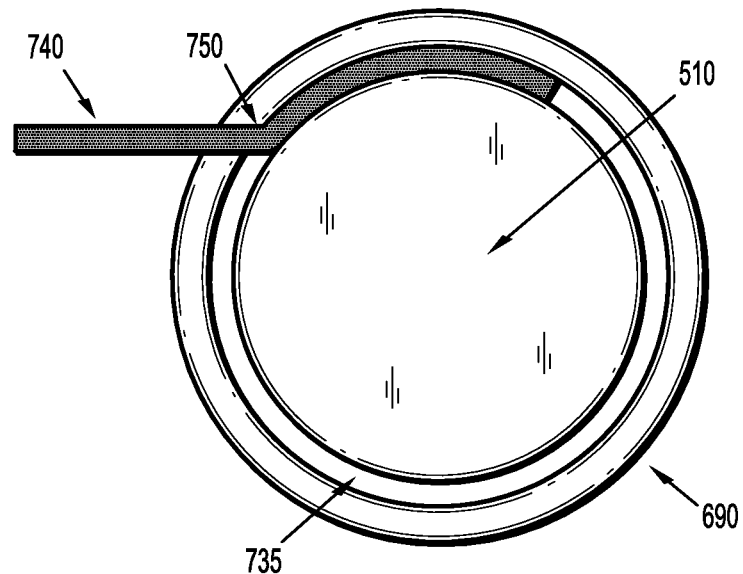
Figure 26D:
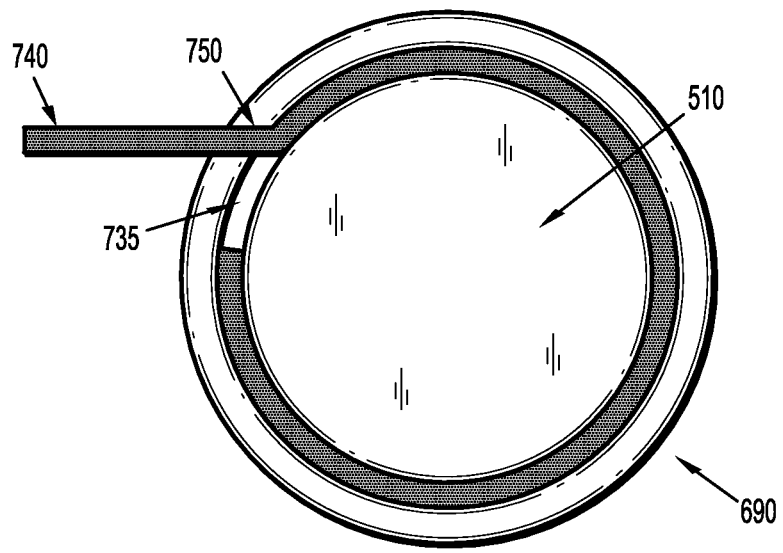

Referring now to FIGS. 26a to 26d, there is seen a sequence of assembling and/or disassembling the detachable second coupling 500 illustrated in FIG. 25. FIG. 26a shows a sectional view of a detachable second coupling 500 fully assembled, before insertion of the flexible annular strip 740. As is seen from FIG. 26a, the distal tip 690 includes a tangential slit 750 leading from the outer surface of the distal tip 690 to the annular sealing cavity 735. As illustrated in FIG. 26b the flexible annular strip 740 is inserted through the tangential slit 750 and into the annular cavity 735. An insertion pressure exerted on the annular strip 740 causes it to be flexibly guided into at least a portion of the annular cavity 735, as illustrated in FIGS. 26c and 26d. However, it should be appreciated that the flexible annular strip 740 may occupy substantially all of the annular cavity 735 after insertion. As described above, the flexible annular strip 740 prevents movement of the distal tip 690 relative to the link 510, thereby firmly securing the distal tip 690 to the link 510.

To disassemble detachable second coupling 500, the flexible annular strip 740 may be removed from the annular cavity 735, for example, by manually pulling the flexible annular strip 740 from the annular cavity 735 via the tangential slit 750. Removal of the annular slit allows movement of the distal tip 690 relative to the link 510, thereby permitting disassembly of the detachable second coupling 500.

Figure 27:
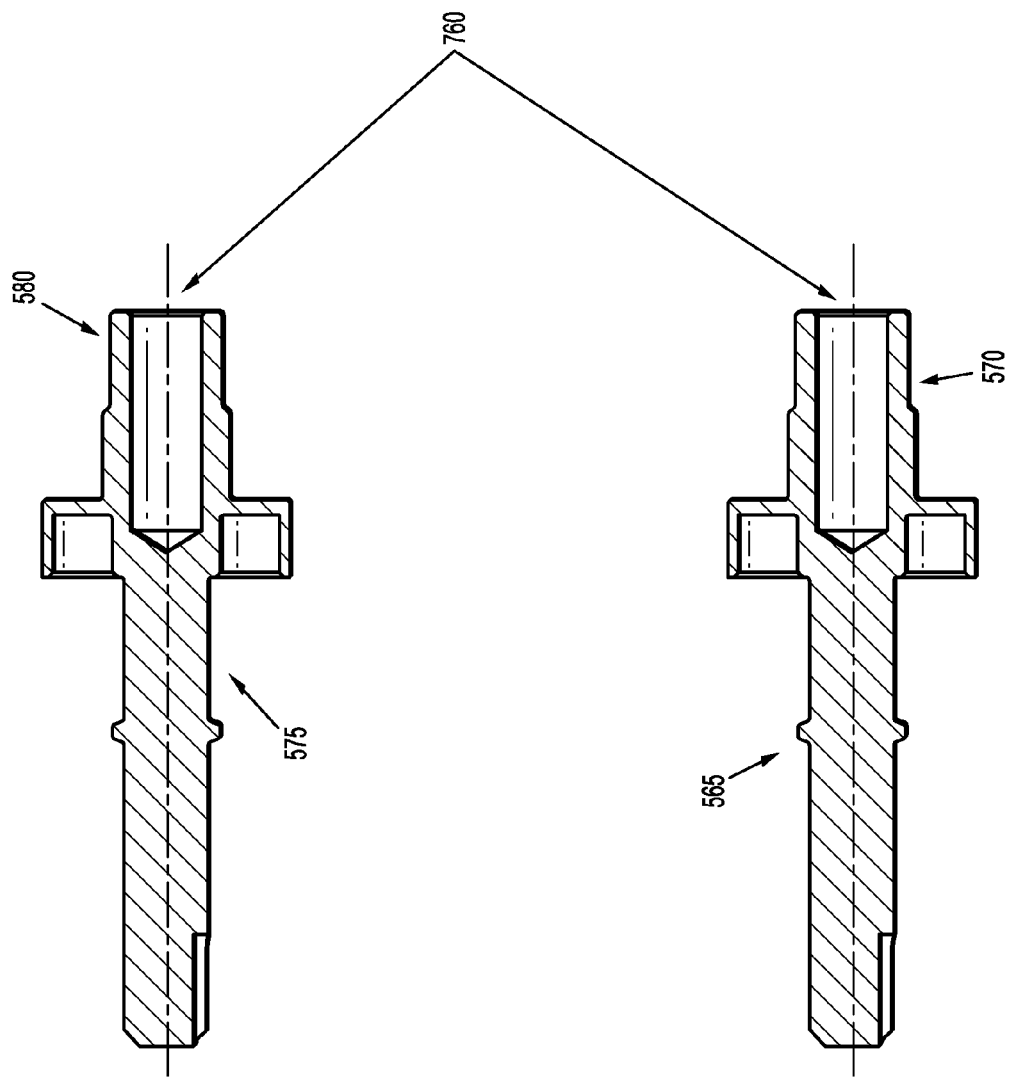
FIG. 27 illustrates example drive shaft members of a detachable second coupling.

Referring now to FIG. 27, there is seen a sectional view of an example shaft engagement member 565, 575. As shown, first shaft engagement member 565 and second shaft engagement member 575 each include a proximal bore 760. When the second coupling is assembled and connected to the flexible shaft 20, the first drive shaft 30 of the flexible shaft 20 and the second drive shaft 32 of the flexible shaft 20 extend from the distal end 24 of the flexible shaft 20 through the bore 525 of the link 510, where they releaseably and non-rotatably connect to the proximal end 570 of the first shaft engagement member 565 and the proximal end 580 of the second shaft engagement member 575, respectively, for example, by being rigidly inserted into a respective proximal bore 760. Each of the first drive shaft 30 and the second drive shaft 32 may include a rigid end piece adapted by size and configuration to frictionally and non-rotatably engage a respective bore 760. It should be appreciated that in this embodiment, the first shaft engagement member 565 and the second shaft engagement member 575 may be removable from first drive shaft 30 and second drive shaft 32, respectively, to allow the detachable second coupling 500 to be disassembled, so that flexible shaft 20 may be, for example, cleaned, sterilized, autoclaved, repaired, replaced, refurbished, upgraded, maintained, etc.

Figure 29:
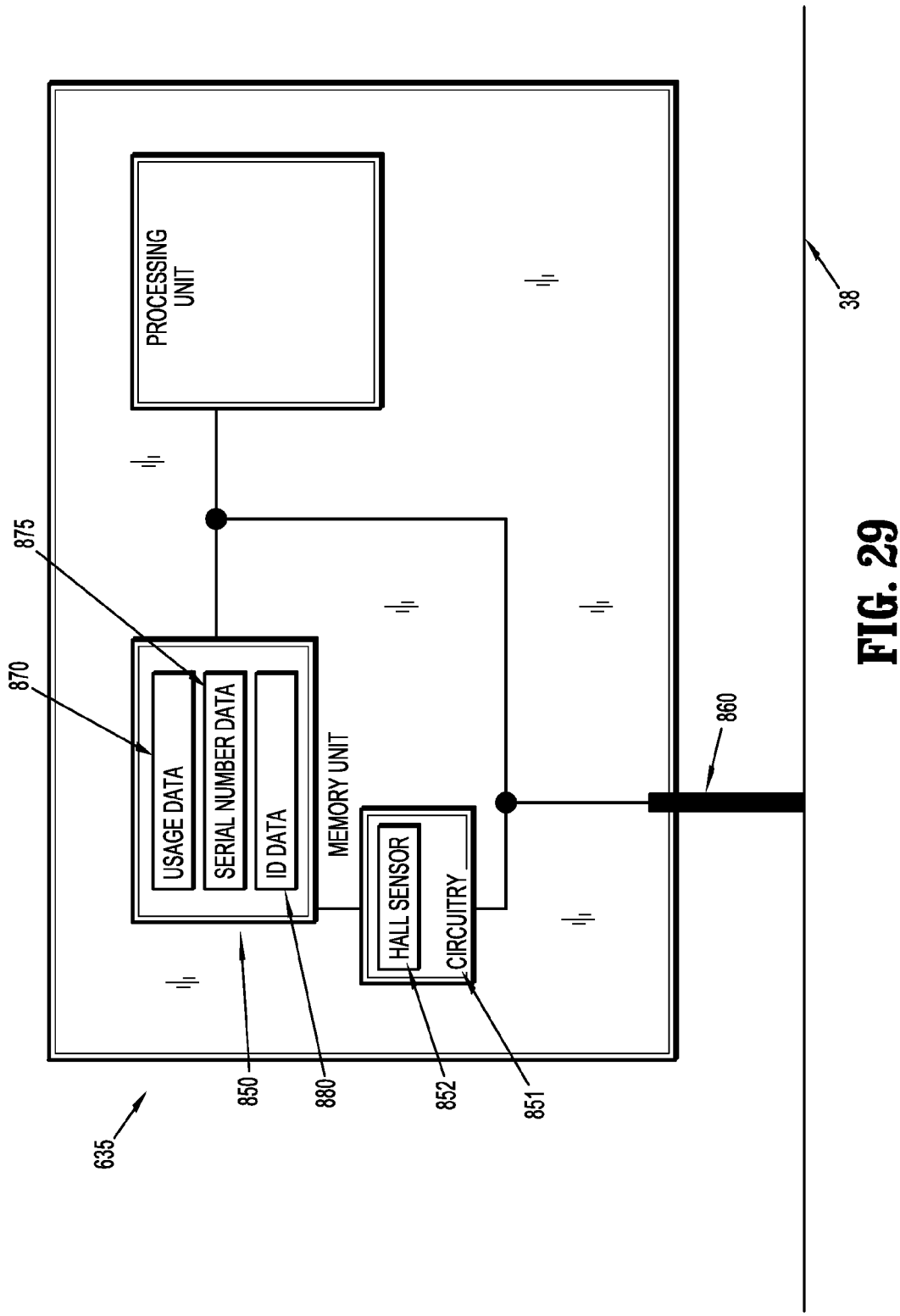
FIG. 29 illustrates an example PCB board for use in a flexible shaft.

FIG. 29 illustrates an example PCB 635 for use within the example second coupling 500. As seen in FIG. 29, PCB 635 includes a memory unit 850, an optional processing unit 855, circuitry 851 (including, for example, Hall-effect devices or Hall sensors 852), and a set of data leads 860 for electrical and logical connection to the data transfer cable 38 of the flexible drive shaft 20. Alternatively, it should be appreciated that the memory unit 850 and/or circuitry 851 need not be located on PCB 635 and may be located anywhere within or on the flexible shaft 20, such as, for example, inside or on the flexible shaft 20, inside or on first coupling 22, and/or inside or on second coupling 500 in a different location. The memory unit 850 may be in the form of, for example, an EEPROM, EPROM, etc. and may be configured, for example, to store usage data 870 of the flexible drive shaft 20, such as, for example, the number of times a rotatable drive shaft 30, 32 is rotated, the number of times a rotatable drive shaft 30, 32 is used, the number of times a rotatable drive shaft 30, 32, the number of times the flexible shaft 20 has been used, the number of rotations of the rotatable drive shaft 30, 32, the number of times the flexible shaft 20 has been connected and/or disconnected from the remote power console 12 and/or a surgical instrument or attachment attachable to the flexible shaft 20, a date, e.g., of initial use, connection, rotation, etc. and/or any other data, etc. The memory unit 850 may also store serial number data 875 and/or identification (ID) data 880 of the flexible shaft 20 indicating, for example, the type of flexible shaft 20 and/or a particular flexible shaft 20, etc. Optional processing unit 855 may be electrical and logical connection to the memory unit 850 and may be configured to, for example, pre-process one or more of the usage data 870, the ID data 880, and the serial number data 870 before being stored in the memory unit 850. The angular position of the drive shafts 30, 32, the direction of rotation of the drive shaft 30, 32, and/or the number of rotations of the drive shaft 30, 32 (e.g., using magnets 590), etc., may be determined and/or determinable in accordance with signals from the Hall sensors 852.

It should be appreciated that a particular flexible shaft 20 may be designed and configured to be used a single time, multiple times, a predetermined number of times, etc. Accordingly, the usage data 870 may be used to determine whether the flexible shaft 20 has been used and/or whether the number of uses has exceeded a maximum number of permitted uses. As more fully described above, an attempt to use a flexible shaft 20 after the maximum number of permitted uses has been reached may cause an ERROR condition.

Figure 28A:
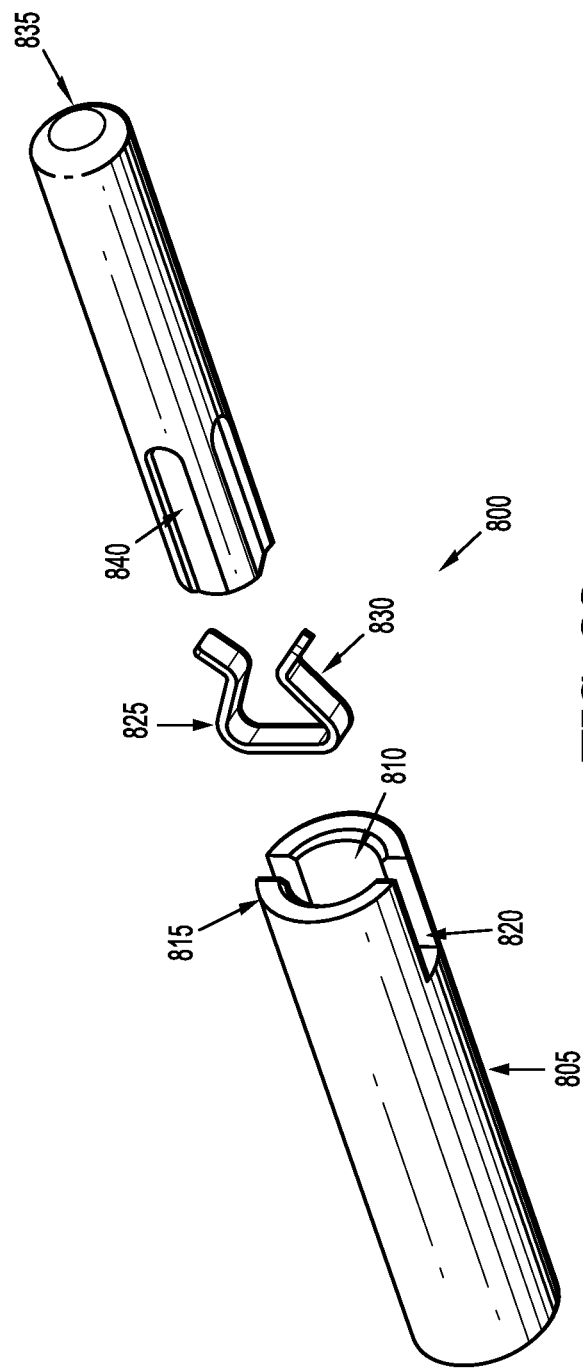
FIG. 28a illustrates an exploded view of an example connection mechanism for connecting a second coupling to a surgical attachment.
Figure 28B:
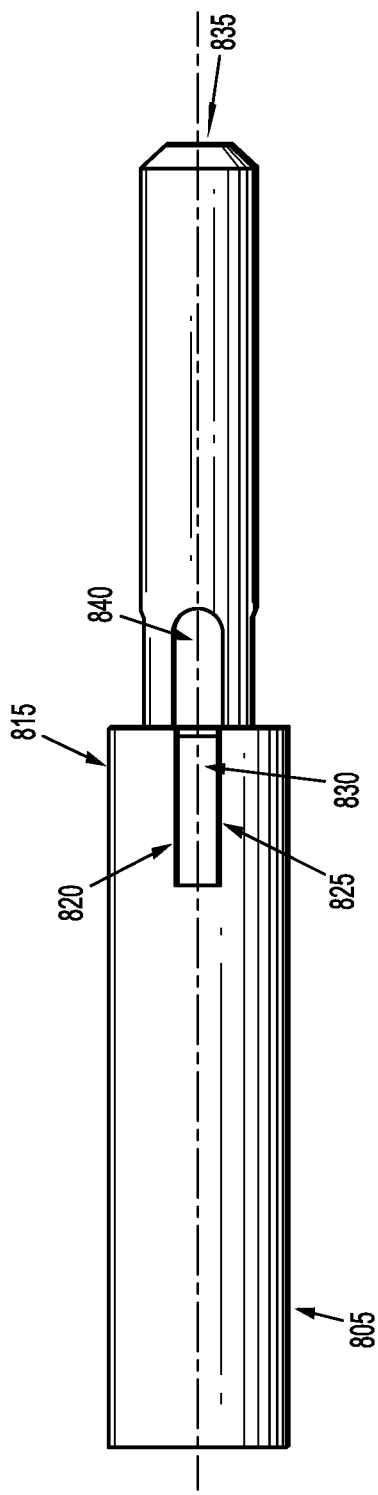
FIG. 28b illustrates an assembled view of an example connection mechanism for connecting a second coupling to a surgical attachment.
Figure 28C:
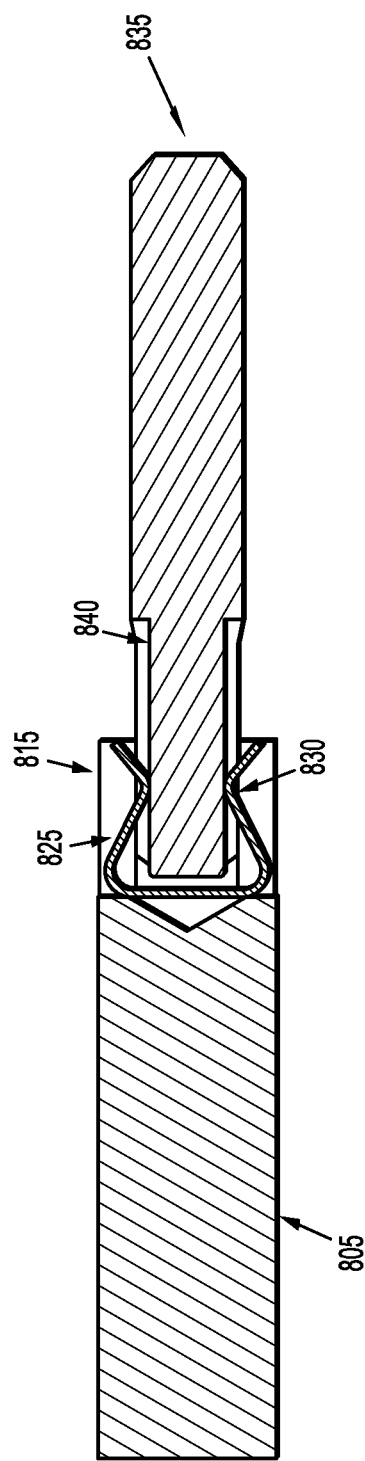
FIG. 28c illustrates an sectional view of an example connection mechanism for connecting a second coupling to a surgical attachment.

Referring now to FIGS. 28a, 28b and 28c, there is seen an example connection mechanism 800 configured to connect a surgical instrument or attachment (e.g., surgical stapler attachment 250) to the second coupling 500 of the flexible shaft 20. Other connection mechanisms are, of course, possible. In this example embodiment, assume, for example, that each of the distal ends 605, 610 of shaft engagement members 565, 575 is represented by engagement shaft 835. Assume also, for example, that a proximal end of a surgical instrument or attachment includes a coupling (e.g, coupling 260) having a first connector (e.g., for driving drive shaft 262) and a second connector (e.g., for driving drive shaft 266) configured as an engagement member 805.

The engagement shaft 835 includes a number of grooves 840. The engagement member 805 has a bore 810 and two longitudinal slits 820. A clip 825 having flanges 830 is inserted in the bore 810 of the engagement member 805. It should be appreciated that engagement member 805 may include any number of longitudinal slits 820 and that there may be a corresponding number of flanges 830 of clip 825 received by the longitudinal slits 820. Engagement shaft 835 is inserted in the bore 810 of the engagement member 805, with at least one of the flanges of the 830 engaged, e.g., frictionally, with a grooves 840 of the engagement shaft 835. In this manner, the engagement shaft 835 and the engagement member 805 may be releasably and non-rotatably coupled.

Although in this example embodiment, FIGS. 28a, 28b, and 28c illustrate a respective engagement member 805 as part of each of the coupling of the surgical instrument or attachment, and the engagement shaft 835 as part of first and second shaft engagement members 565, 575, it should be appreciated that in another example embodiment, the first and second shaft engagement member 565, 575 may include an engagement member 805 and the coupling of the surgical instrument or attachment may include engagement shafts 835.

Figure 31:
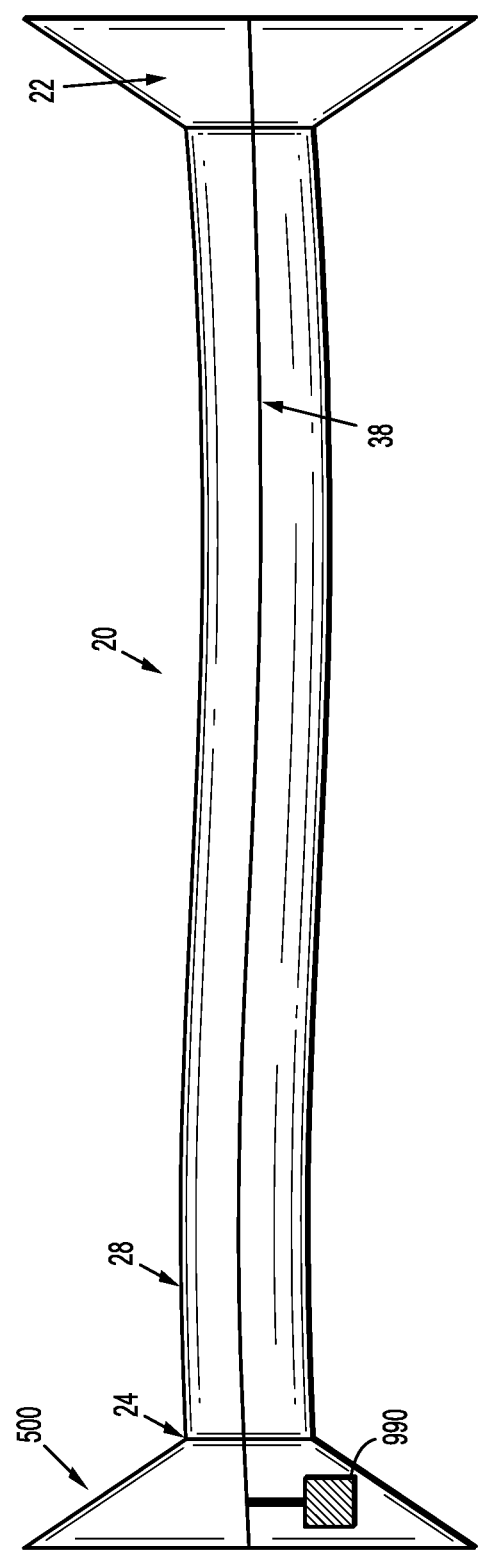
FIG. 31 illustrates an example flexible shaft including a moisture sensor for detecting moisture.

Referring now to FIG. 31, there is seen an example flexible shaft 20 including a moisture sensor 990 configured to detect moisture within the flexible shaft 20. FIG. 31 shows moisture sensor 990 disposed within the second coupling 500 (e.g., mounted on PCB 635). Moisture sensor 990 is coupled to the data transfer cable 38 to communicate an indication of the presence of moisture (e.g., sensed moisture data is communicated) to the remote power console 12. The presence of moisture within the flexible shaft 20 may cause corrosion of the components of the flexible shaft 20, such as, for example, the rotatable drive shafts 30, 32, electronic or electrical components arranged in the flexible shaft 20, etc. In accordance with and/or based on the sensed moisture data, the remote power console 12 may communicate the presence of moisture to a user, such as, for example, by audible or visual signal.

Figure 32:
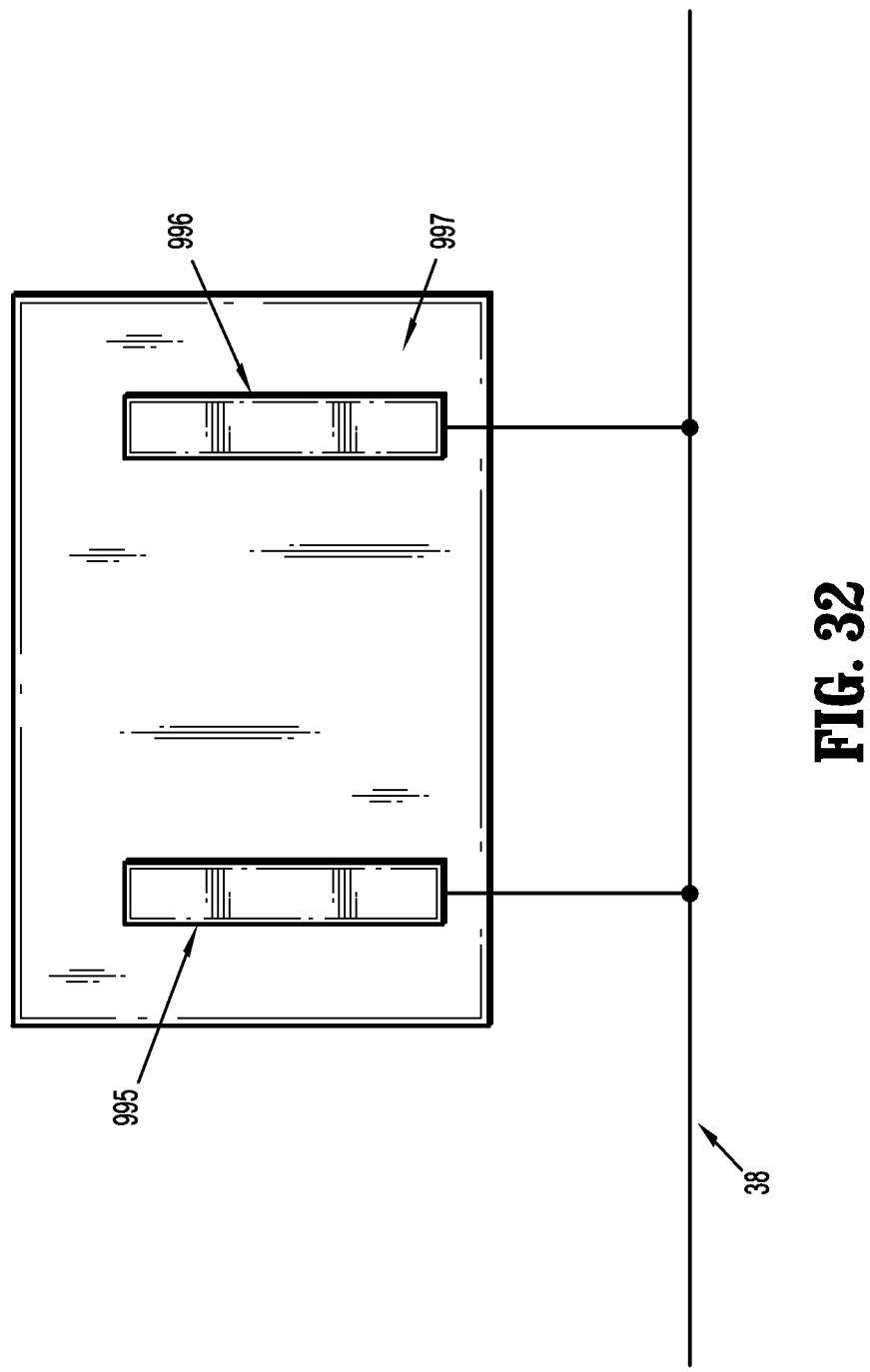
FIG. 32 illustrates an example moisture sensor.

Referring now to FIG. 32, there is seen an example moisture sensor 990 including a first printed lead 995 and a second printed lead 996, each of which is printed on board element 997 and connected to the data transfer cable 38. The presence of moisture may change the electrical conductivity between the printed leads 995, 996, e.g., the electrical resistance between the printed leads 995, 996 may vary in accordance with the amount of moisture present.

It will be appreciated that a moisture sensor 900 may additionally or alternatively be disposed within the elongated sheath of the flexible shaft 20, and coupled to, e.g., data transfer cable 38.

Figure 30A:
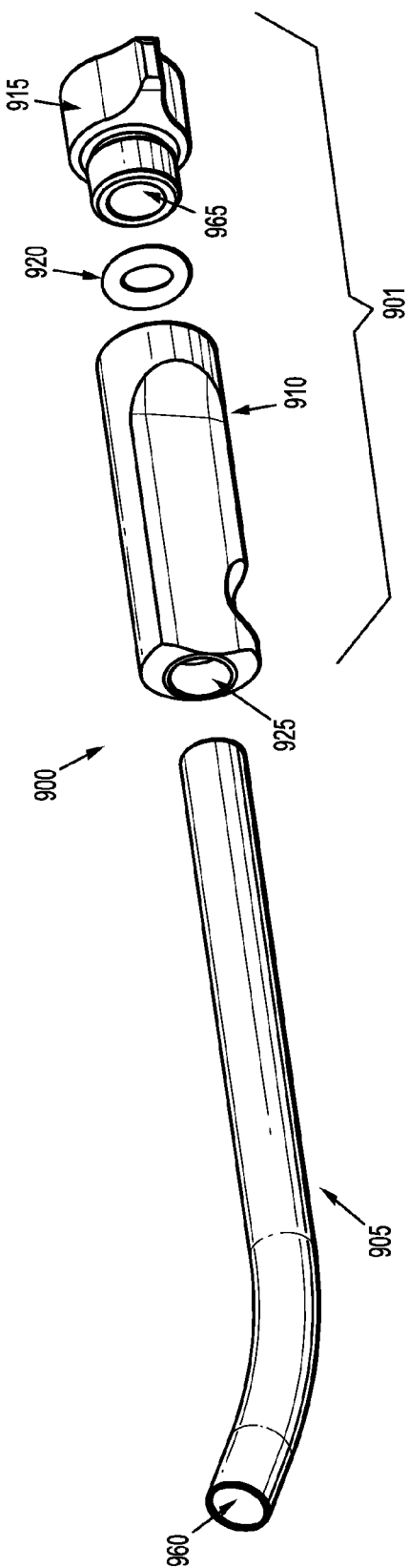
FIG. 30a illustrates an exploded view of a rigid sleeve.
Figure 30B:
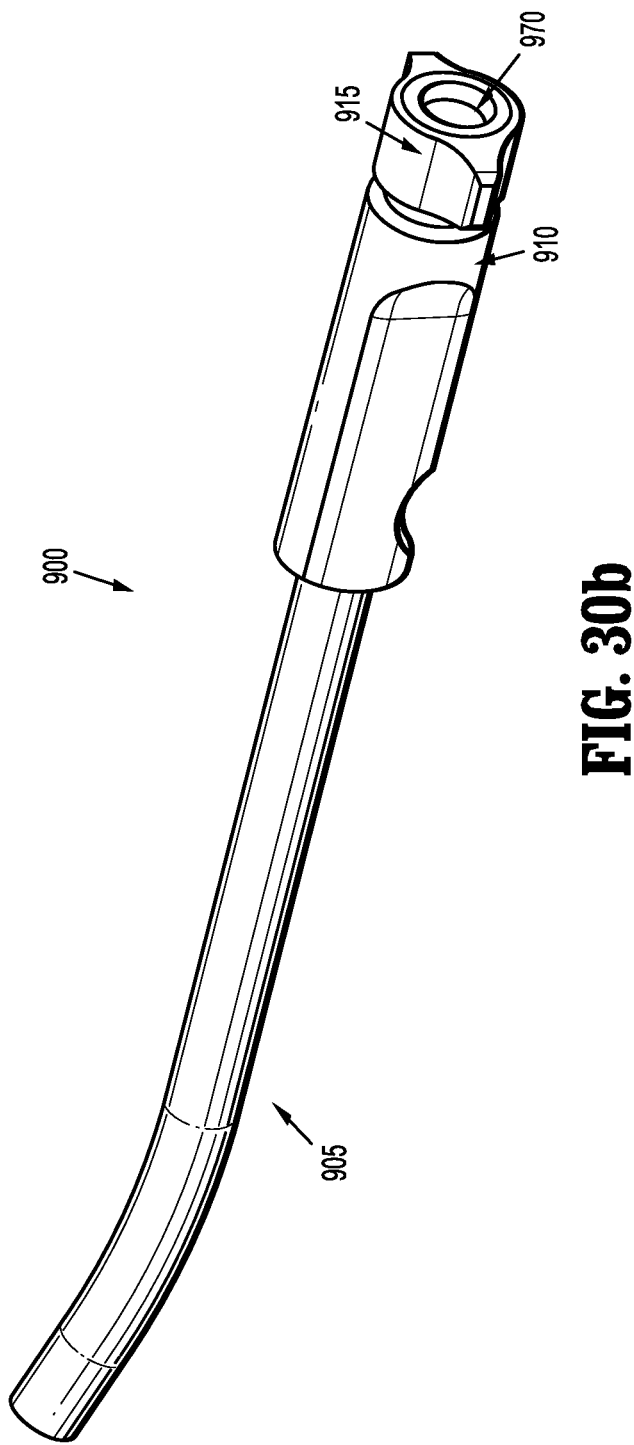
FIG. 30b illustrates an assembled view of a rigid sleeve.
Figure 30C:
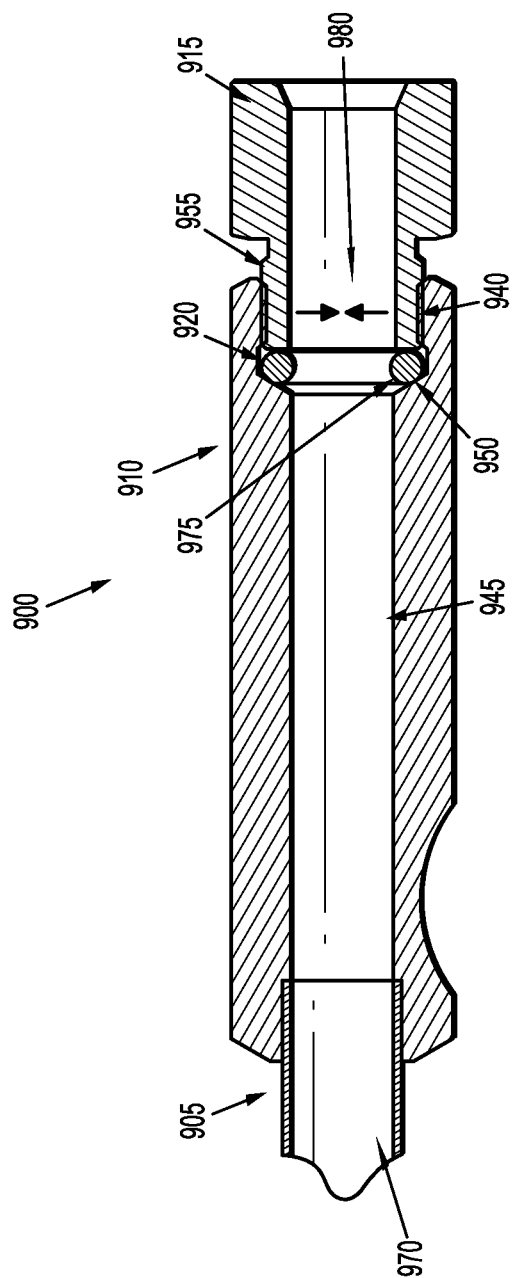
FIG. 30c illustrates a sectional view of a rigid sleeve.

In some cases, the user of the surgical device 10 may desire to make a portion of the flexible shaft 20 rigid (relative to the flexibility of flexible shaft 20). Accordingly, referring now to FIGS. 30a, 30b, and 30c, there is seen an example shape-retaining sleeve 900 for making rigid or maintaining a desired shape of at least a portion of the flexible shaft 20. FIG. 30a illustrates an exploded view of the shape-retaining sleeve 900, FIG. 30b illustrates an assembled view of the shape-retaining sleeve 900, and FIG. 30c illustrates a sectional view of the shape-retaining sleeve 900. The shape-retaining sleeve 900 includes an elongated sleeve or shaft member 905 having a bore 960 extending therethrough, and a positioner or securing device 901 including housing member 910 having a bore 925 extending therethrough, a securing knob 915 having a bore 965 extending therethrough, and an O-ring 920. It should be appreciated that the sleeve member 905 may be constructed from a rigid non-bendable material or, alternatively, may be constructed from a material capable of being deformed into different configurations or shapes, but generally retaining its shape once deformed.

In the example embodiment illustrated in FIGS. 30a to 30c, the sleeve member 905 is rigidly received within at least a portion of the bore 925 of the housing member 910. As illustrated in FIG. 30c, bore 925 may have a proximal portion 940 having a larger diameter than a distal portion 945. A distal end 955 of the securing knob 915 is rigidly received within the proximal portion 940 of the bore 925. Helical threads may be provided on the inside surface of the proximal portion 940 of the bore 925 and the outer surface of the distal end 955 of the securing knob 915 to permit the securing knob to be screwed into place. Alternatively, for example, the securing knob 915 may frictionally and slidably engage within the proximal portion 940 of the bore 925. The O-ring 920 is received within the proximal portion 940 of the bore 925 and urged against an interface 950 between the proximal and distal portions 940, 945 of the bore 925 by the distal end 955 of the securing knob 915. Compression of the O-ring at the interface 950 urges at least a portion of an inner annular surface 975 of the O-ring 920 inwardly in a radial direction indicated by arrows 980, thereby frictionally engaging and securing a flexible shaft 20 inserted in the sleeve member 905 through the O-ring 920. When fully assembled, the bores 960, 925, 965 are disposed adjacent to one another, forming a continuous channel 970 for receiving at least a portion of the flexible shaft 20.

At least a portion of the flexible shaft 20 may be inserted through the continuous channel 970 for maintaining rigid at least the portion of the flexible shaft 20 in a predefined or predefinable shape, in accordance with the predefined or predefinable shape of the sleeve member 905. The distal end 24 of flexible shaft 20 extends through the continuous channel 970 and beyond at least a portion of a distal end 985 of the sleeve 900, the second coupling 26 detachably securable to the distal end 24 of flexible shaft 20. As described above, the receipt of the securing knob 915 by bore 925 causes the inner annular surface 975 of O-ring 920 to frictionally and securely engage the flexible shaft 20, thereby holding it firmly in place. It will be appreciated that the sleeve 900 may be retained or secured in a selected longitudinal position along the flexible shaft 20 via the securing device 901. The sleeve 900 generally retains the flexible shaft 20 in a predetermined or predeterminable shape.

It should be appreciated that the securing knob 915 may frictionally secure the flexible shaft 20 by other arrangements other than the O-ring 920, such as, for example, by threaded engagement, compressive engagement, clamping, gluing, pasting, etc. It should also be appreciated that use of the shape-retaining sleeve is optional, i.e., the flexible shaft may be usable without the shape-retaining sleeve being employed.

The several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby and that its scope is to be determined by that of the appended claims.

What is claimed is:

1. A coupling, comprising:
    a distal cover;
    a link having a proximal end and a distal end, the proximal end being configured for attachment to a shaft of an electro-mechanical surgical device and the distal end being configured to be selectively detachably connected to the distal cover to form a fluid-tight and air-tight seal therebetween;

a flexible strip locking mechanism for detachably coupling the distal cover to the distal end of the link, wherein the distal cover defines a first annular recess and the link defines a second annular recess such that upon connecting the distal cover and the link, the first annular recess and the second annular recess together form an annular cavity having the flexible strip locking mechanism removably disposed therein;

a rotatable shaft engagement member configured to engage a rotatable drive shaft, at least a portion of the rotatable shaft engagement member being disposed in the distal cover; and a moisture sensor disposed in the distal cover configured to sense moisture in the distal cover.

2. The coupling according to claim 1, further comprising: a memory unit disposed in the distal cover.

3. The coupling according to claim 2, wherein the memory unit stores data including at least one of serial number data, identification data or usage data.

4. The coupling according to claim 2, further comprising: a data transfer cable electrically connected to the memory unit.

5. The coupling according to claim 1, wherein the coupling is configured to detachably couple to a surgical instrument.

6. The coupling according to claim 1, wherein the distal cover defins a tangential slit extending from an outer surface of a distal tip thereof to the annular cavity, the tangential slit configured for receiving the flexible strip locking mechanism.

7. The coupling according to claim 6, wherein the flexible strip locking mechanism takes on an annular shape upon being inserted into the annular cavity.

* * * * *